(12) United States Patent
Bradley et al.

(10) Patent No.: US 10,507,247 B2
(45) Date of Patent: Dec. 17, 2019

(54) OPTICAL PROBES FOR MATRIX METALLOPROTEINASES

(71) Applicant: The University Court of the University of Edinburgh, Edinburgh, Midlothian (GB)

(72) Inventors: Mark Bradley, Midlothian (GB); Sunay Vijaykumar Chankeshwara, Midlothian (GB); Alicia Megia-Fernandez, Midlothian (GB)

(73) Assignee: The University of the University of Edinburgh, Edinburgh, Midlothian (GB)

( * ) Notice: Subject to any disclaimer, the term of this patent is extended or adjusted under 35 U.S.C. 154(b) by 0 days.

(21) Appl. No.: 15/560,100

(22) PCT Filed: Mar. 18, 2016

(86) PCT No.: PCT/GB2016/050765
§ 371 (c)(1),
(2) Date: Sep. 20, 2017

(87) PCT Pub. No.: WO2016/151299
PCT Pub. Date: Sep. 29, 2016

(65) Prior Publication Data
US 2018/0085466 A1 Mar. 29, 2018

(30) Foreign Application Priority Data
Mar. 20, 2015 (GB) .................................. 1504778.0

(51) Int. Cl.
| | | |
|---|---|---|
| *A61B 10/00* | (2006.01) |
| *A61B 5/00* | (2006.01) |
| *A61B 8/00* | (2006.01) |
| *A61K 47/54* | (2017.01) |
| *A61K 49/00* | (2006.01) |
| *C12Q 1/37* | (2006.01) |
| *G01N 33/58* | (2006.01) |
| *G01N 33/574* | (2006.01) |

(52) U.S. Cl.
CPC ........ *A61K 47/556* (2017.08); *A61K 49/0041* (2013.01); *A61K 49/0056* (2013.01); *C12Q 1/37* (2013.01); *G01N 33/582* (2013.01); *G01N 33/574* (2013.01); *G01N 2333/96486* (2013.01); *G01N 2800/085* (2013.01); *G01N 2800/102* (2013.01); *G01N 2800/7052* (2013.01)

(58) Field of Classification Search
CPC ...... A61K 47/00; A61K 47/556; A61K 49/00; A61K 49/0056; A61K 49/0041; G01N 33/582; G01N 2800/7052; G01N 2800/102; G01N 2800/085; G01N 2333/96486; G01N 33/574; C12Q 1/37
USPC .......... 424/1.11, 1.49, 1.65, 1.69, 1.81, 1.85, 424/1.89, 9.1, 9.2, 9.6; 514/1, 1.1
See application file for complete search history.

(56) References Cited

U.S. PATENT DOCUMENTS 9,549,997 B2 * 1/2017 Walton ............... A61K 49/0041

FOREIGN PATENT DOCUMENTS

| | | |
|---|---|---|
| WO | 9725437 | 7/1997 |
| WO | 03095475 | 11/2003 |
| WO | WO 2009/092062 A2 | 7/2009 |
| WO | 2010021822 | 2/2010 |
| WO | 2012063088 | 5/2012 |
| WO | WO 2012/123916 A2 | 9/2012 |
| WO | WO 2012/136958 A2 | 10/2012 |
| WO | WO-2012136958 A2 * | 10/2012 ......... A61K 49/0041 |

OTHER PUBLICATIONS

International Search Report and the Written Opinion of the International Searching Authority corresponding to International Patent Application No. PCT/GB2016/050765 (12 pages) (dated Jun. 10, 2016).
Deng et al. "Substrate Specificity of Human Collagenase 3 Assessed Using a Phage-displayed Peptide Library" The Journal of Biological Chemistry, 275(40):31422-31427 (2000).
Rasmussen et al. "Use of a Multiple-Enzyme/Multiple-Reagent Assay System to Quantify Activity Levels in Samples Containing Mixtures of Matrix Metalloproteinases" Biochemistry, 43(11):2987-2995 (2004).
Search Report under Section 17(6) corresponding to GB application No. GB1504778.0 (2 pages) (dated Apr. 21, 2016).

* cited by examiner

*Primary Examiner* — D. L. Jones
(74) *Attorney, Agent, or Firm* — Myers Bigel, P.A.

(57) ABSTRACT

An optical probe is presented comprising at least one fluorophore connected to at least one quencher by an enzyme cleavable peptide sequence; the or each fluorophore being substantially fluorescently quenched by the at least one quencher when connected to the enzyme cleavable peptide sequence; the or each fluorophore is separated from the at least one quencher when the enzyme cleavable peptide sequence of the at least one probe element is cleaved; and the enzyme cleavable peptide sequence is selectively cleavable by one or more matrix metalloproteinase (MMP). Methods of use of the optical probe are also presented.

30 Claims, 25 Drawing Sheets
Specification includes a Sequence Listing.

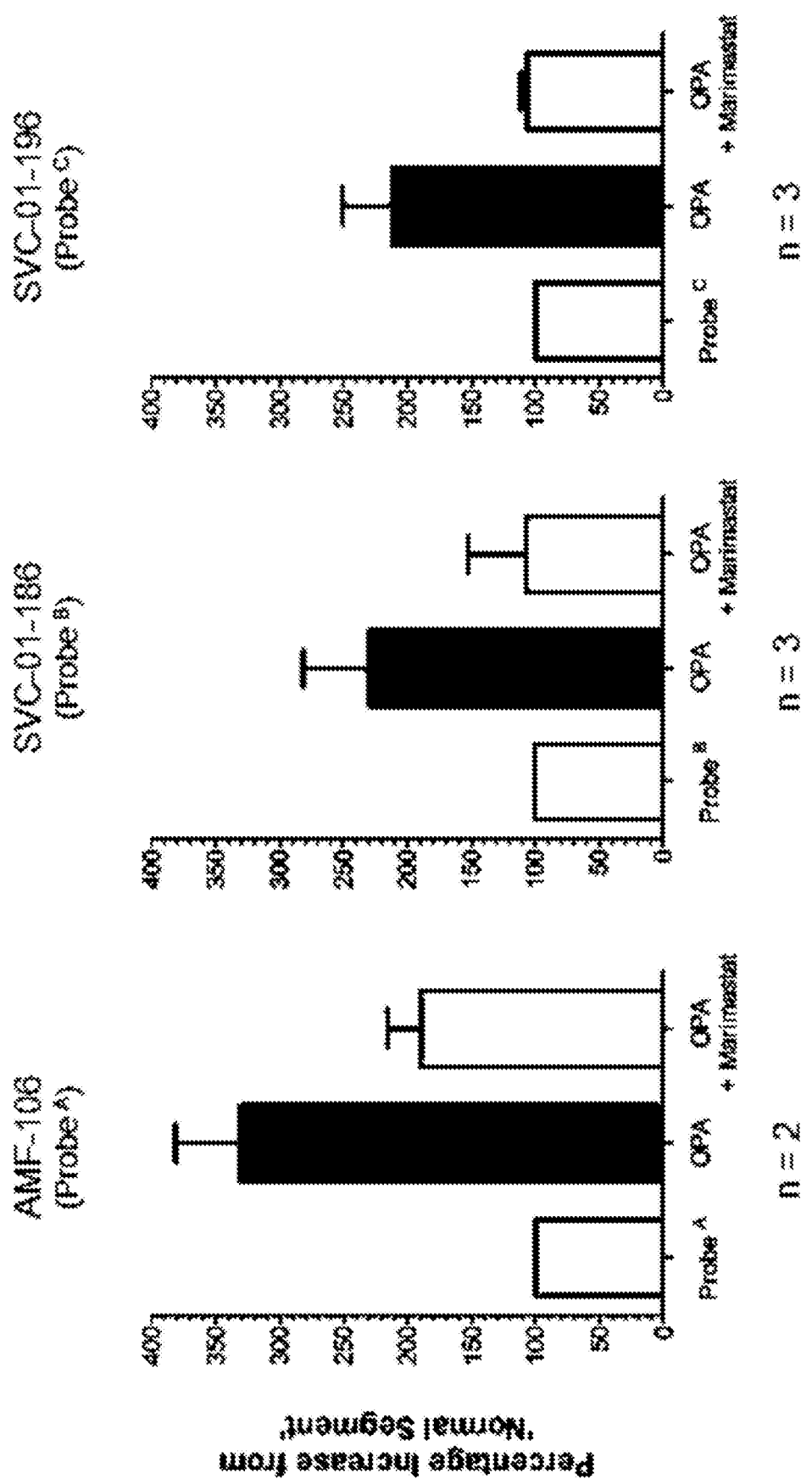
Fig. 11cont.

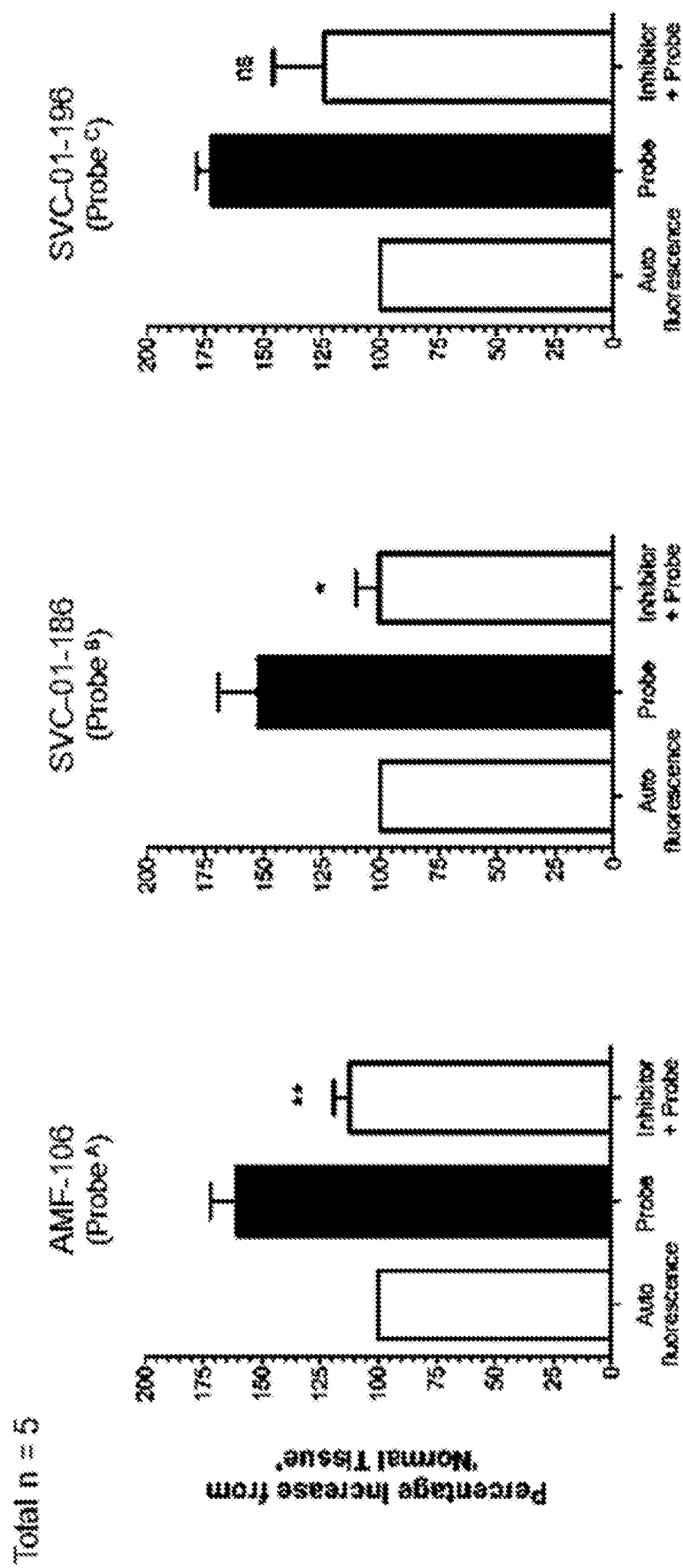
Fig. 12cont.

SEQUENCE LISTING

```
<160> NUMBER OF SEQ ID NOS: 16

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Gly Pro Lys Gly Leu Lys Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Gly Pro Lys Gly Ile Lys Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: X = Nle
<220> FEATURE:
<221> NAME/KEY: MISC_FEATURE
<222> LOCATION: (5)..(5)
<223> OTHER INFORMATION: X = Nle

<400> SEQUENCE: 3

Gly Pro Lys Gly Xaa Lys Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X = bAla

<400> SEQUENCE: 4
```

```
Pro Phe Gly Met Lys Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X = bAla

<400> SEQUENCE: 5

Pro Phe Gly Leu Lys Xaa
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X = bAla

<400> SEQUENCE: 6

Pro Phe Gly Ile Lys Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X = Nle
<220> FEATURE:
<221> NAME/KEY: MISC_FEATURE
<222> LOCATION: (6)..(6)
<223> OTHER INFORMATION: X = bAla

<400> SEQUENCE: 7

Pro Phe Gly Xaa Lys Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 8

Pro Xaa Gly Met Phe Gly
1               5

<210> SEQ ID NO 9
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X = 3-cyclohexylalanine

<400> SEQUENCE: 9

Pro Xaa Gly Met Trp Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X = 3-cyclohexylalanine
<220> FEATURE:
<221> NAME/KEY: MISC_FEATURE
<222> LOCATION: (5)..(5)
<223> OTHER INFORMATION: X = 4-methoxyphenyl alanine

<400> SEQUENCE: 10

Pro Xaa Gly Met Xaa Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X = 3-cyclohexylalanine

<400> SEQUENCE: 11

Pro Xaa Gly Met Tyr Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X = 3-cyclohexylalanine
<220> FEATURE:
<221> NAME/KEY: MISC_FEATURE
<222> LOCATION: (6)..(6)
<223> OTHER INFORMATION: X = bAla

<400> SEQUENCE: 12

Pro Xaa Gly Met Lys Xaa Gly
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (2)..(2)
<223> OTHER INFORMATION: X = 3-cyclohexylalanine

<400> SEQUENCE: 13

Pro Xaa Gly Met His Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X = 3-cyclohexylalanine

<400> SEQUENCE: 14

Pro Xaa Gly Met Lys Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide

<400> SEQUENCE: 15

Gly Pro Lys Gly Leu Lys Gly Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X = Nle
<220> FEATURE:
<221> NAME/KEY: MISC_FEATURE
<222> LOCATION: (6)..(6)
<223> OTHER INFORMATION: X = bAla

<400> SEQUENCE: 16

Pro Phe Gly Xaa Lys Xaa Lys
1               5
```

US 10,507,247 B2

OPTICAL PROBES FOR MATRIX METALLOPROTEINASES

STATEMENT OF PRIORITY

This application is a 35 U.S.C. § 371 national phase application of International Application Serial No. PCT/GB2016/050765, filed Mar. 18, 2016, which claims priority to GB Application No. 1504778.0, filed Mar. 20, 2015, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 9052-345_ST25.txt, 4,425 bytes in size, generated on Sep. 20, 2017 and filed via EFS-Web, is provided in lieu of a paper copy. This Sequence Listing is hereby incorporated by reference into the specification for its disclosure.

FIELD OF THE INVENTION

The invention relates to the field of optical probes, more specifically to optical probes that may be used for the detection of, inter alia, cancer, fibrosis and arthritis.

BACKGROUND OF THE INVENTION

Fibroproliferative diseases of the lung and other organs constitute a heavy burden of morbidity and untimely deaths. Fibrosis results in permanent loss of the tissue's ability to function optimally. In the lung, gas exchange ability is impaired by the formation of scar tissue. Often, Idiopathic Pulmonary Fibrosis (IPF) is diagnosed late (on CT scans/lung biopsy) and has a high mortality with a median survival time from diagnosis of 3 years. It is currently impossible to identify patients with Adult Respiratory Distress Syndrome (ARDS) and other inflammatory lung diseases that are developing secondary fibrosis. Moreover there are no effective therapies for fibrosis despite it being a highly active cellular process which should be accessible to intervention. Part of the problem is the time required to establish drug effectiveness in vivo and the poor utility of existing biomarkers. Thus, there is an urgent need to develop diagnostic methodologies that will permit the more effective and rapid determination of both disease activity and efficacy of emerging anti-fibrotic drugs.

Molecular imaging offers a viable approach to interrogate non-invasively living samples in real time with spatial resolution when combining the technical instrumentation with optical imaging probes. Optical probes are typically developed for each specific target for effective diagnostic imaging (Biochemistry 2010, 49, 1364-1376). Activatable optical probes can provide functional details of molecular events, and provide advantages such as providing information at the molecular level. Furthermore, they can be used with a small portable system, provide information quickly, and can be microdosed (<100 µg), thereby reducing the risk of side effects.

fCFM (fibre-Confocal Fluorescence Microscopy) has been used for studying in vivo the alveolar structure of the human lung during bronchoscopy [Eur. Resp. J 2009, 33, 974-985. Proc. Am. Thorac. Soc. 2009, 4, 444-449]. Its use in combination with optical probes for specific enzymes can provide valuable information.

Matrix metalloproteinases (MMPs) are extracellular zinc-dependent endopeptidases capable of degrading the extracellular matrix. MMPs have long been of interest as pharmaceutical targets and play an important role in the tissue remodelling associated with various physiological or pathological processes such as morphogenesis, angiogenesis, tissue repair, cirrhosis, arthritis, and metastasis (Cancer Metastasis Rev. 2008, 27, 679-690). They can also be considered as biomarkers overexpressed in fibrotic lung [Eur. Respir. J. 2011, 38 (6) 1461-1467; Am. J. Respir. Crit. Care Med 2000, 162(5) 1949-1956, Eur. Respir. J. 2009, 33, 77-84] making them ideal for molecular targeting with labelled peptides and could serve as a useful tool for early diagnosis of diseases via optical imaging. Over-expression and knockout studies in mice show a critical role of proteinases (MMP-2/9) in lung fibrosis, and their expression has been consistently shown to be elevated in the lung lavage fluid of fibrotic subjects compared both to levels in healthy lung and levels in patients with other lung diseases [Cell Biol. Toxicol. 2002, 18(1), 51-61].

Many proteinase probes exploit the FRET (Forster Resonance Energy Transfer, also known as Fluorescence Resonance Energy Transfer) phenomenon to detect enzymatic activity [Biotechnol. J. 2014, 9, 266-281, Chem. Comm., 2008, 4250-4260], where the protease substrate is located between a fluorophore/quencher pair. Alternatively, the "self-quenching" effect in multi-branched systems previously described for the detection of AspN Endoproteinase [Angew. Chem. 2002, 41, 17, 3233-3236] and more recently HNE [Org. Biomol. Chem., 2013, 11, 4414-4418] has been applied as well for cathepsin S [J. Med Chem. 2006, 49, 4715-4720].

Several matrix metalloproteinase probes have been described over the years based on potent MMP inhibitors and activatable fluorescent probes. To date, design and development of labelled substrates for these enzymes have largely focused on sensing tumour-related activity [review Cancer biotherapy and Radiopharmaceuticals, 21, 5, 2006, 409-416], as well as for osteoarthritis or atherosclerosis [Chem. BioChem. 2012, 13, 2002-2020; Contrast Media Mol. Imaging 2014, 9, 187-210]. Despite many efforts, most of the probes known in the art are limited in usefulness in vivo at least, due to poor specificity and in vivo stability.

Accordingly, it is an object of the present invention to provide improved optical probes that are capable of specifically detecting MMP, or types of MMP, that are preferably stable in vivo.

STATEMENTS OF THE INVENTION

According to a first aspect of the invention, there is provided an optical probe comprising at least one fluorophore connected to at least one quencher by an enzyme cleavable peptide sequence; the or each fluorophore being substantially fluorescently quenched by the at least one quencher when connected to the enzyme cleavable peptide sequence; the or each fluorophore is separated from the at least one quencher when the enzyme cleavable peptide sequence of the at least one probe element is cleaved; wherein the enzyme cleavable peptide sequence comprises one of SEQ ID NO.1 to SEQ ID NO.14 (Table 1) and is selectively cleavable by one or more matrix metalloproteinase (MMP).

TABLE 1

| SEQ ID NO. | Sequence |
|---|---|
| 1 | G-P-K-G-L-K-G |
| 2 | G-P-K-G-I-K-G |
| 3 | G-P-K-G-Nle-K-G |
| 4 | P-F-G-M-K-βA |
| 5 | P-F-G-L-K-βA |
| 6 | P-F-G-I-K-βA |
| 7 | P-F-G-Nle-K-βA |
| 8 | P-Cha-G-M-F-G |
| 9 | P-Cha-G-M-W-G |
| 10 | P-Cha-G-M-Y(Me)-G |
| 11 | P-Cha-G-M-Y-G |
| 12 | P-Cha-G-M-K-βA-G |
| 13 | P-Cha-G-M-H-G |
| 14 | P-Cha-G-M-K-G |

(wherein Nle = norleucine; Ch = 3-cyclohexylalanine; βA = β-alanine; Y(Me) = 4-methoxyphenyl alanine)

SEQ ID NO.1 corresponds to a known peptide sequence. However, such a sequence is not known in the type of optical probes described herein.

In one embodiment, there is provided an optical probe as described herein wherein the enzyme cleavable peptide sequence comprises one of SEQ ID NO.2 to SEQ ID NO.14 (Table 1).

By the term "substantially fluorescently quenched" we refer to the fluorescence of the quenched fluorophore being less than 30% of the fluorescence of the unquenched fluorophore, preferably less than 20%, and more preferably, less than 10%.

As a result of cleavage of the enzyme cleavable peptide sequence by MMP, the at least one fluorophore of the probe is separated from the quencher and therefore the fluorescence of the at least one fluorophore is no longer quenched by the quencher. Accordingly, upon excitation of the probe with an appropriate wavelength of light, the at least one fluorophore of the probe fluoresces.

Therefore, fluorescence of the optical probe of the invention is indicative of the presence of MMP. Typically, fluorescence of the optical probe of the invention is indicative of the presence of active and functional MMP.

Preferably, the enzyme cleavable peptide sequence is selectively cleavable by MMP-2 and/or MMP-9 and/or MMP-13. For example, the enzyme cleavable peptide sequence may be selectively cleavable by MMP-2. The enzyme cleavable peptide sequence may be selectively cleavable by MMP-9. The enzyme cleavable peptide sequence may be selectively cleavable by MMP-13.

More preferably, the enzyme cleavable peptide sequence is selectively cleavable by MMP-9 and/or MMP-13. The enzyme cleavable peptide sequence may be selectively cleavable by MMP-9 and/or MMP-13 only. For example, in one embodiment, the enzyme cleavable peptide sequence is cleavable by MMP-9 and MMP-13.

In preferred embodiments of the invention, the enzyme cleavable peptide sequence is cleaved by one or more of MMP-2, MMP-9 and MMP-13 to produce an increase in fluorescence of the probe that is at least five times greater than the background fluorescence. More preferably, the enzyme cleavable peptide sequence is cleaved by one or more of MMP-2, MMP-9 and MMP-13 to produce an increase in fluorescence that is at least eight times greater than the background fluorescence.

Preferably, the enzyme cleavable peptide sequence is not cleaved by MMPs other than MMP-2, MMP-9 and MMP-13. The enzyme cleavable peptide sequence may be a substrate for MMP-2, MMP-9 and MMP-13, but not other MMPs. For example, the enzyme cleavable peptide sequence may not be cleaved by MMP-1, MMP-3, MMP-7, MMP-8, and MMP-11.

MMPs are enzymes which play an important role in tissue remodelling and as such are associated with various pathological processes. Accordingly, an optical probe that detects the activity of MMPs may be used to detect those pathological processes. Examples of pathologies include fibrosis, arthritis, particularly osteoarthritis, cancer, atherosclerosis and cirrhosis. Indeed MMPs are upregulated in any inflammatory disease and as such these probes may be useful in their diagnosis.

MMP, in particular MMP-9 and MMP-13, has been shown to be overexpressed in fibrotic tissue. Therefore, an optical probe, the fluorescence of which is indicative of the presence of MMP-9 and/or MMP-13 by their selective cleavage of the enzyme cleavable peptide sequence comprising SEQ ID NOs.1 to 14, typically SEQ ID NOs.2 to 14, allows the presence of fibrotic tissue to be detected.

Fibrotic tissue may occur in many tissue types, such as heart, lung, liver, connective tissue, skin, intestine, or joints. Accordingly, the detection of MMP-9 or MMP-13 in those tissue types may be indicative of the presence of fibrotic tissue. For example, the detection of MMP-9 and/or MMP-13 in the lung of a subject may be indicative of active fibroproliferation within fibrotic areas of the lung.

MMP has been shown to be associated with arthritis. For example, MMP-13 has been shown to be overexpressed in osteoarthritis. Therefore, the provision of an optical probe, the fluorescence of which is indicative of the presence of MMP, may allow the presence of arthritis to be detected. For example, the detection of MMP-13 in or around a joint of a subject may be indicative of osteoarthritis in that joint.

In a further example, the detection of MMPs in tissue may be indicative of a cancer. In one embodiment, the detection of MMPs in tissue may allow benign neoplasm to be differentiated from malignant neoplasm. In another embodiment, the detection of MMPs in tissue may allow the boundary between cancerous tissue and normal tissue to be determined. For example, MMP may be detected at the boundary between cancerous tissue and normal tissue, or MMP may be detected in cancerous tissue and not in normal tissue. Accordingly, the probe of the invention may detect the presence of a tumour, and/or determine whether that tumour is benign or malignant.

Cancers highly express MMP9. The combination of an abnormal area of tissue and the molecular signature of MMP activity would alert the clinician that this could be cancer. Also, the margins of tumours highly express MMPs, such that the probes described herein would help surgeons identify the margins of tumours, for instance when they are to be removed.

Typically, optical probes known in the art have poor selectivity for MMP-2, MMP-9 and MMP-13, and are only capable of detecting the presence of MMPs generally.

The inventors have surprisingly found that the probes of the present invention are highly selective for MMP-2, MMP-9 and MMP-13, or are substrates for only MMP-2, MMP-9 and MMP-13, and allow these MMPs to be detected in vitro and in vivo in the presence of other, similar enzymes. Therefore, the probes of the invention allow diseases that overexpress MMP-2, MMP-9 and MMP-13, such as fibroproliferation, such as fibrosis, cirrhosis, arthritis and cancer, to be detected accurately, even in the presence of other similar enzymes. This is particularly beneficial where other MMPs are expressed in normal tissue.

The enzyme cleavable peptide sequence may comprise one of SEQ ID NO.3, SEQ ID NO.4, SEQ ID NO.5 and SEQ ID NO.7 to SEQ ID NO.14. Preferably, the enzyme cleavable peptide sequence comprises one of SEQ ID NO.3, SEQ ID NO.4, SEQ ID NO.5 and SEQ ID NO.7 to SEQ ID NO.14. More preferably, the enzyme cleavable peptide sequence comprises one of SEQ ID NO.3, SEQ ID NO.5 and SEQ ID NO.7. Still more preferably, the enzyme cleavable peptide sequence comprises one of SEQ ID NO.5 and SEQ ID NO.7 or comprises SEQ ID NO.7. The inventors have found that enzyme cleavable sequences comprising these sequences show greater selectivity for MMP-9 and MMP-13, or MMP-2, MMP-9 and MMP-13, and/or have been shown to be more resistant to non-specific cleavage by other proteinases than those known in the art.

Preferably, the enzyme cleavable peptide sequence comprises SEQ ID NO.7. The inventors have found that probes comprising SEQ ID NO.7 are both specific to MMP-2, MMP-9 and MMP-13, and are also highly resistant to non-specific cleavage by other proteinases such as plasmin, thrombin and factor Xa. Accordingly, probes of the invention comprising SEQ ID NO.7 allow the selective detection of the activity of MMP-2, MMP-9 and MMP-13 in the presence of other proteinases, such as in tissue or tissue samples, for example.

The probe may comprise one or more additional amino acids either side of the enzyme cleavable peptide sequence. This can be illustrated schematically as x-sequence-y, x-sequence-, or -sequence-y, where x and y represent one to ten amino acids, preferably 1 to five amino acids, or more preferably 1 to 2 amino acids.

Typically, the fluorescence of a first fluorophore may be suppressed, or "quenched", by a neighbouring moiety. The neighbouring moiety, or "quencher", may also be a fluorophore. Where the first fluorophore and the neighbouring second fluorophore are of the same type (i.e. they are the same chemical entity with the same excitation and emission spectra), the first and second fluorophores may quench the fluorescence of each other, and "self-quench". For example, carboxy fluorescein, Cy5, and 7-nitrobenz-2-oxa-1,3-diazole (NBD) may self-quench.

If the first fluorophore and the neighbouring second fluorophore are of different types (i.e. they are different chemical entities and have different excitation and emission spectra), then if the emission spectra of the first fluorophore and the excitation spectra of the second fluorophore overlap so that energy may be transferred from one to the other via Fluorescence (or Forster) Resonance Energy Transfer (FRET). In other words, they may form a "FRET pair", and the second fluorophore may quench the fluorescence of the first fluorophore. The second fluorophore absorbs the fluorescence of the first fluorophore and fluoresces itself at a different wavelength. Accordingly, the second fluorophore may be a "fluorescent quencher". For example, FRET pairs that comprise two fluorophores include (fluorophore/quencher) Cy3/Cy5, and carboxy fluorescein/seminaphthorhodamine carboxylate derivatives.

The neighbouring moiety may be a chemical entity that does not fluoresce. The neighbouring moiety may still quench the fluorescence of the first fluorophore, but instead of fluorescing itself, the neighbouring moiety disperses the energy it received from the fluorophore as heat to its surroundings, and is a "dark quencher". For example, FRET pairs that comprise a dark quencher include (fluorophore/quencher) fluorescein/dimethylaminoazobenzenesulfonic acid (DABSYL), carboxy fluoresceinlBHQ-1, carboxy fluorescein/methyl red, NBD/methyl red, carboxy naphthofluorescein/QSY21, carboxy naphthofluorescein/BHQ-3, seminaphthorhodamine carboxylate derivatives/BHQ-3, seminaphthorhodamine carboxylate derivatives/QSY21, Cy3/QSY21, Cy5/QSY21, and Cy5/BHQ-3.

The at least one quencher and the at least one fluorophore may quench. A probe comprising a quencher and at least one fluorophore that quench is substantially dark and does not produce fluorescence before the enzyme cleavable peptide sequence is cleaved. For instance, the at least one quencher may be the same type of fluorophore as the at least one fluorophore, and the at least one quencher and the at least one fluorophore may self-quench.

In embodiments where the at least one fluorophore and the at least one quencher self-quench, (i.e. the at least one fluorophore and the at least one quencher are the same type of fluorophore), the fluorophore may be selected from fluorescein, or a derivative thereof, seminaphthorhodamine carboxylate or a derivative thereof, a cyanine fluorophore, such as Cy2, Cy3, Cy5, Cy5.5 or Cy7, rhodamine or derivative thereof, a fluorescent protein, such as green fluorescent protein (GFP), yellow fluorescent protein (YFP), or cyan fluorescent protein (CFP), or 7-nitrobenz-2-oxa-1,3-diazole (NBD).

In another embodiment, the at least one quencher is a different type of fluorophore than the at least one fluorophore, and is a fluorescent quencher. Accordingly, before the enzyme cleavable peptide sequence is cleaved a probe comprising at least one fluorescent quencher, fluoresces at the wavelength of light emitted by the fluorescent quencher and does not fluoresce at the wavelength of light emitted by the at least one fluorophore.

In a further embodiment, the at least one quencher may be a dark quencher. Accordingly, a probe comprising a dark quencher is substantially dark and does not produce fluorescence before the enzyme cleavable peptide sequence is cleaved.

In embodiments where the at least one fluorophore and the at least one quencher are different chemical entities, the at least one fluorophore may be any fluorophore that may form a FRET pair with a suitable quencher. Accordingly, the fluorophore and the quencher are chosen as a pair to ensure that they have appropriate excitation and emission spectra for the transfer of energy from the fluorophore to the quencher (i.e. they form a FRET pair). For example, typical fluorophore/quencher pairs include Cy3/Cy5, Cy3/QSY21, Cy5/QSY21, Cy5/BHQ-3, carboxy fluorescein/tetramethylrhodamine, fluorescein/methyl red, carboxy fluorescein/BHQ-1, NBD/methyl red, carboxy naphthofluorescein/QSY21, carboxy naphthofluorescein/BHQ-3, seminaphthorhodamine carboxylate derivatives/BHQ-3, seminaphthorhodamine carboxylate derivatives/QSY21, cyan fluorescent protein (CFP)/yellow fluorescent protein (YFP), carboxy fluorescein/methyl red, etc. Further examples of FRET pairs may be readily identified by the skilled person.

Preferably, the at least one fluorophore and the at least one quencher are chosen from Cy5/QSY21, carboxy fluorescein/methyl red, carboxy fluorescein/BHQ-1 and Cy5/BHQ-3.

Typically, the probes of the invention are operable to be used to detect MMP in a target zone. The target zone may be a portion of tissue within a subject, and the method may be carried out in vivo. The portion of tissue may be a portion of the heart, lung, liver, connective tissue, skin, intestine, or joints of a subject. The probes of the invention may be used in the circulatory system, the nervous system, the digestive system or the reproductive system For example, the target area may be a portion of the lung of a subject.

The target zone may be a portion of a cell culture, a tissue sample such as a biopsy sample, or a liquid sample such as a bodily fluid sample.

Accordingly, the probes of the invention may be used in vivo, ex vivo or in vitro.

The probes of the invention may be delivered to a target zone by any means known in the art. For example, the probes of the invention may be delivered by endoscope, spray, injection, topically, or ingestion. For example, where the probes are to be delivered to a portion of the lung, the probes may be delivered to the target zone using a bronchoscope.

Illumination light of a suitable wavelength to excite fluorophores of the probe may be delivered to the target zone by any conventional means known in the art. Typically, in embodiments where the probe is to be used within the body of a subject, the light is delivered by means of an optical fibre or similar. The fluorescence from the probes in the target zone may be collected by an optical fibre or similar. The fluorescence from the probes in the target zone may be collected by the same optical fibre that delivered the illumination light. For example, to both deliver the probe to the target zone, to deliver light to the target area, and to detect fluorescence from the target zone. The collected fluorescence is typically delivered to a recording device, such as a charge-coupled device (CCD) or similar. Alternatively, the fluorescence from the probes in the target zone may be directly collected by a recording device, such as a CCD or similar. Alternatively, individual instruments may be used to deliver the probe to the target area, to deliver light to the target zone and to detect fluorescence from the target area.

For example, fluorescence may be detected from the tissue of a target area using fibered confocal fluorescence microscopy (fCFM).

Fluorescence from the probes may be imaged indirectly. For example, the fluorescence may be converted into acoustic waves by using photoacoustic imaging. Photoacoustic imaging may allow high resolution images of the target area to be generated.

Preferably, the subject is a human subject. However, the subject may be a non-human animal such as equine, ovine, bovine, canine, feline or rodent, for example.

The at least one fluorophore may be connected to the enzyme cleavable peptide sequence by a spacer. The at least one quencher may be connected to the enzyme cleavable peptide sequence by a spacer. The spacer may be a saturated or unsaturated hydrocarbon chain, an ether, a polymer, a polyethylglycol (PEG), a poly glycol, a poly ether or similar. The spacer may be a peptide. In embodiments where the spacer is a peptide, the peptide may be 1-10 amino acids in length, 1-20 amino acids in length, or 1-30 amino acids in length. The spacer may be a mixture of amino acids and a saturated or unsaturated hydrocarbon chain, an ether, a polymer, a PEG, a poly glycol, a poly ether or similar. For example, the spacer may comprise 6-aminohexanoic acid (Ahx), or PEG, or an alternating chain of PEG and amino acids.

In embodiments where the spacer comprises polar or hydrophilic groups, such as PEG, or poly ether for example, the linker may increase the solubility of the probe in aqueous media. Therefore, the provision of a probe comprising at least one spacer comprising a polar or hydrophilic group may allow the probe to be more readily soluble in biologically acceptable media for direct application to a target area without the requirement for additional surfactants, for example.

The probe may comprise at least one reporter fluorophore that is not substantially fluorescently quenched. Preferably, the at least one reporter fluorophore fluoresces at a wavelength that is different to the wavelength of light at which the at least one fluorophore fluoresces. Accordingly, the at least one reporter fluorophore fluoresces before and after the enzyme cleavable peptide sequence is cleaved, and therefore, the at least one reporter fluorophore fluoresces when illuminated with a suitable wavelength of light. Accordingly, the presence or location of the probe in a target zone may be monitored with and without the presence of MMP and used as a reference.

In some embodiments, the probe of the present invention may be depicted as:

$$F\text{-}A\text{-}Seq\text{-}B\text{-}Q \tag{1}$$

where F=at least one fluorophore

A, B=a spacer, which may be individually present or absent

Seq=a peptide sequence comprising the enzyme cleavable peptide sequence

Q=at least one quencher

It is convenient to define the unit of at least one fluorophore connected to an enzyme cleavable peptide sequence as a "probe element". In other words, a probe element may comprise at least one fluorophore connected to an enzyme cleavable peptide sequence.

Accordingly, the probe element may be depicted as:

$$(F\text{-}A\text{-}Seq)\text{-} \tag{2}$$

In one embodiment of the invention, the probe comprises a single probe element and a quencher.

Preferably, the probe comprises a plurality of probe elements, and each of the plurality of probe elements comprises at least one fluorophore connected to an enzyme cleavable peptide sequence.

Optical probes known in the art are often unstable in vivo or in other cases, such as tissue lysates, tissue samples or samples of bodily fluids, due to processes such as non-specific cleavage of the probe by enzymes. Such non-specific cleavage may produce fluorescence of the probe and be mistaken as indicative of the presence of MMP in a target area. Alternatively, non-specific cleavage may break the probe down and prevent the probe from being observed at all.

Surprisingly, the provision of an optical probe comprising a plurality of probe elements in combination with determined sequences improves the stability of the probe in vivo. Without wishing to be bound by theory, the inventors suggest that the provision of a plurality of probe elements may shield each probe element from unspecific cleavage, thereby increasing the structural resilience of the probe.

In addition, the provision of a probe comprising a plurality of probe elements provides an increased number of fluorophores per probe, thereby providing an increase in fluorescence per probe. Furthermore, this increase in fluorescence per probe may provide a greater signal-to-noise ratio that may allow lower concentrations of MMP to be detected, or lower concentrations of the probe to be used.

The probe may comprise a core and the plurality of probe elements may be connected to the core. Each probe element within the plurality of probe elements may be independently connected directly to the core. Each probe element within the plurality of probe elements may be independently connected indirectly to the core via a linker. The linker may be a saturated or unsaturated hydrocarbon chain, an ether, a polymer, a polyethylglycol (PEG), a poly glycol, a poly ether or similar. The linker may comprise one or more amino acids. For example, the linker may be selected from the list: [-(lysine)-(PEG$_2$)-]$_{1-2}$, [-(PEG-k)-]$_{1-3}$, and [-(PEG-k)$_{0-2}$-NH—(CH$_2$)$_3$—O—CH$_2$—].

By the term "core" we refer to a common moiety that joins the plurality of probe elements to form a single unit. Accordingly, the core could be a single atom, or comprise a functional group, a saturated or unsaturated hydrocarbon chain or a polyglycol (linear, branched, or cyclical), a peptide sequence, a heterocycle or a polymer. The core is typically chosen to have the correct valency for the number of probe elements that are required to be connected to the core. For example, in embodiments with three probe elements, the core is chosen to have a valency of three or more, such that the three probe elements may be connected to the core.

The core may comprise a plurality of connectors that may bind to each of the plurality of probe elements, thereby connecting each probe element within the plurality of probe elements to the core.

Accordingly, some embodiments of the invention may be depicted as:

$$[\text{F-A-Seq-B-Q-L}]_n\text{-C} \qquad (3)$$

$$\text{or } [\text{Q-A-Seq-B-F-L}]_n\text{-C} \qquad (4)$$

where F=at least one fluorophore
A, B=a spacer, which may be individually present or absent
Seq=a peptide sequence comprising the enzyme cleavable peptide sequence
Q=at least one quencher
L=a linker, which may be present or absent
n=2-6
and C=core In embodiments where the linker comprises polar or hydrophilic groups, such as PEG, or poly ether for example, the linker may increase the solubility of the probe in aqueous media. Therefore, the provision of a probe comprising at least one linker comprising a polar or hydrophilic group may allow the probe to be more readily soluble in biologically acceptable media for direct application to a target area without the requirement for additional surfactants, for example.

Preferably, the linker comprises at least one D-amino acid. More preferably, the linker comprises at least one D-lysine residue. The provision of a linker comprising a D-amino acid, such as a D-lysine residue, has surprisingly been found to increase the stability and longevity of the probes in the presence of enzymes such as plasmin, thrombin and factor Xa. Accordingly, the provision of at least one D-lysine residue, for example, in the linker may prevent nonspecific cleavage of the linker by enzymes present in vivo.

Where several probe elements are provided in a single probe, the at least one fluorophore of each probe element within the plurality of probe elements may self-quench, such that the at least one fluorophore of a first probe element substantially fluorescently quenches the at least one fluorophore of a second probe element. Accordingly, the at least one fluorophore of the first probe element acts as the quencher for the at least one fluorophore of the second probe element and vice versa, and an additional quenching moiety may not be required. Therefore, the probe may be simpler and cheaper to manufacture.

The core may comprise the or each at least one quencher. In other words, each probe element within the plurality of probe elements may not comprise a quencher and the at least one fluorophore of each probe element within the plurality of probe elements may be quenched by the quencher of the core. Therefore, the probe may contain fewer quenchers or quenching moieties than probes where each probe element within the plurality of probe elements comprises at least one quencher. Therefore, the probe may be more readily synthesised with fewer components, and the probe may be made at a reduced cost.

Each probe element within the plurality of probe elements may comprise at least one quencher connected to at least one fluorophore by an enzyme cleavable peptide sequence. Accordingly, the at least one fluorophore may be separated from the at least one quencher when the enzyme cleavable peptide sequence is cleaved by MMP. The at least one fluorophore of each probe element within the plurality of probe elements may be the same. The at least one quencher of each of the plurality of probe elements may be the same.

Alternatively, the at least one quencher and the at least one fluorophore of each probe element within the plurality of probe elements may be different. This may be useful when a first fluorophore fluorescing at a first wavelength is used to detect enzyme activity while a second fluorophore fluorescing at a second wavelength different to that of the first wavelength acts as a reference. Such a dual element probe would be used in multi-wavelength detection, which monitors for fluorescence at both the first and second wavelengths.

In some embodiments, each probe element within the plurality of probe elements may comprise at least two quenchers. For example, each probe element within the plurality of probe elements may comprise one fluorophore and two quenchers, or each probe element may comprise two fluorophores and two quenchers. The provision of probe elements comprising at least two quenchers may quench the fluorescence of the at least one fluorophore of the probe elements more completely than probe elements comprising a single quencher, thereby providing a greater signal-to noise ratio, and providing a greater change in fluorescence when the enzyme cleavable peptide sequence is cleaved.

In embodiments where the probe comprises a plurality of probe elements connected directly or indirectly to a core, the at least one quencher of each probe element within the plurality of probe elements may be at the proximal end of the probe element to the core, and the at least one fluorophore of each probe element within the plurality of probe elements may be at the distal end of the probe element to the core. Accordingly, when the enzyme cleavable peptide sequence is cleaved, the fluorophores are separated from the quenchers and the core, the quenchers remaining connected to the core.

Alternatively, the at least one quencher of each probe element within the plurality of probe elements may be at the distal end of the probe element to the core and the at least one fluorophore of each probe element within the plurality of probe elements may be at the proximal end of the probe element to the core. Accordingly, when the enzyme cleavable peptide sequence is cleaved, the quenchers may be separated from the fluorophores and the core, the fluorophores remaining connected to the core. For example, the fluorophores connected to the core may not self-quench and the quenchers may be required to quench the fluorescence of the fluorophores.

One or more of the plurality of probe elements may comprise at least two fluorophores. The provision of one or more of the plurality of probe elements comprising at least two fluorophores may provide a higher signal to noise ratio for the probe, and may provide a greater fluorescent signal when the enzyme cleavable peptide sequences of the plurality of probe elements are cleaved. Accordingly, where the probes of the invention are applied to a target area, a higher contrast between a target area without MMPs present and a target area where MMPs are present may be obtained.

The probe may comprise at least two probe elements, at least three probe elements, at least four probe elements or at least five probe elements. In one embodiment, when the probe comprises at least two probe elements, the enzyme cleavable peptide sequence is SEQ ID NO. 1.

Preferably, the probe comprises three probe elements. The more probe elements, the greater the enhancement of the fluorescence upon cleavage of the enzyme cleavable peptide sequence.

The probe may comprise a polymerisable moiety such that the probe may polymerise. Accordingly, the probe may be a polymerisable probe. The polymerisable moiety is preferably an ethylenically unsaturated moiety. The polymerisable moiety is preferably located such that the polymerisable moiety does not hinder the fluorescent quenching of the at least one fluorophore by the at least one quencher.

In one embodiment of the invention, the polymerisable probe may be polymerised in the presence of a solvent to form a gel. For example, the polymerisable probe may be polymerised in an aqueous media and form a hydrogel, where the polymerised probe forms a polymer network expanded by water. The gel may comprise an additional component. The additional component may adjust one or more properties of the gel. For example, where the additional component is a porogen (for example a sugar), the gel may become more porous, and therefore, media may more readily disperse throughout the gel.

Accordingly, a gel comprising a polymerisable probe and a porogen may increase the surface area of the gel and thereby allow a greater concentration of MMP to penetrate the gel and cleave the enzyme cleavable peptide sequence of the polymerised probe.

The polymerisable probe may be polymerised with one or more additional monomers to form a polymer composition. The one or more additional monomers may include styrene, methyl methacrylate, ethylene glycol diacrylate, acrylamide etc. The one or more additional polymers may provide desirable properties to the polymer composition, such as structural strength, flexibility, porosity etc.

The polymerisable probe may be polymerised with one or more initiators, usually tetramethylethylenediamine (TEMED) and ammonium persulfate, TEMED and potassium persulfate, or TEMED and riboflavin.

The one or more additional polymers may act as a support to the polymerisable probe.

According to a second aspect of the invention, there is provided a method of detecting MMP activity in a target zone, the method comprising the steps:
 a. applying a probe according to the first aspect to the target zone;
 b. illuminating the target zone with an appropriate wavelength of light to excite fluorophores of the probe; and
 c. determining the fluorescence intensity of probe,
wherein significant fluorescence of the or each fluorophore of the probe is indicative of the presence of MMP in the target zone.

The detection of the presence of MMP in the target zone may be used in the diagnosis of conditions such as fibrosis, cirrhosis, cancer and arthritis.

By the term "significant fluorescence" we refer to the fluorescence of a fluorophore that results from sufficient separation of that fluorophore from the quencher of a probe to prevent the quencher quenching the fluorescence of the fluorophore, that is above the background or, where present, autofluorescence in the target area. The autofluorescence of the indigenous cells or tissue within the target area may have a shorter fluorescent lifetime than the fluorophore of the first probe. The autofluorescence of the indigenous cells or tissue within the target area may reduce over time at a faster rate than that of the fluorophore of the probe. Accordingly, fluorescence observed in the target area that decays more slowly over time may be indicative of the probe, and fluorescence observed in the target area that reduces more quickly over time may be indicative of autofluorescence.

Therefore, the method may comprise the step of determining the fluorescence intensity of the target zone over a period of time, determining the rate of decay of fluorescence during the period of time, and determining the fluorescence intensity of that fluorescence with a slower rate of decay, wherein the fluorescence with a slower rate of decay corresponds to the fluorescence of the probe.

Preferably, the MMP is MMP-2, and/or MMP-9 and/or MMP-13. Preferably, the MMP is MMP-9 and/or MMP-13.

Methods of determining the activity of MMP using optical probes known in the art cannot differentiate between the various different types of MMP, such as MMP-2, MMP-9 and MMP-13 over MMP-1, MMP-3 and MMP-8, for example. Only some types of MMP have been shown to be overexpressed in some diseases, such as fibrosis, cancer and arthritis. For example, MMP-2, MMP-9 and MMP-13 have been shown to be overexpressed in fibrotic tissue. Therefore, the provision of a method to specifically detect MMP-2, MMP-9 and MMP-13, for example, allows the specific and reliable detection of diseases that overexpress MMP-2, MMP-9 and MMP-13 in the presence of other related enzymes.

The at least one fluorophore of the probe may be selected dependent on the location of the target zone. For example, if the target zone is directly observable, such as on the skin or within the lung of a subject, the at least one fluorophore may be selected to fluoresce in the visible region of the spectrum. If the target area is to be observed through the skin or tissue, the at least one fluorophore may be selected to fluoresce in the infrared region of the spectrum, such that the fluorescence of the probe is not significantly absorbed by the skin or tissue and therefore be observable through the skin of tissue. For example, the at least one fluorophore may be selected to fluoresce in the near infrared (fluorescence wavelength of between 600 nm to 950 nm). Infrared imaging techniques are well known to the skilled person in the art.

The target zone may be a portion of tissue within a subject, and the method may be carried out in vivo. The portion of tissue may be a portion of the heart, lung, liver, connective tissue, skin, intestine, or joints of a subject, for example. For example, the target zone may be a portion of the lung of a subject. In addition, the method of the invention may be carried out in the circulatory system, the nervous system, the digestive system or the reproductive system.

The target zone may be a portion of a cell culture, a tissue sample such as a biopsy sample, or a liquid sample such as a bodily fluid sample.

The target zone may be a target area. The target zone may be a target volume.

Accordingly, the method of the invention may be carried out in vivo, ex vivo or in vitro.

The probes of the invention may be delivered to a target zone by any means known in the art. For example, the probes of the invention may be delivered by endoscope, spray, injection, topically, or ingestion. For example, where the probes are to be delivered to a portion of the lung, the probes may be delivered to the target zone using an endoscope, such as a bronchoscope.

Illumination of a suitable wavelength to excite fluorophores of the probe may be delivered to the target zone by any conventional means known in the art. Typically, in embodiments where the probe is to be used within the body of a subject, the light is delivered by means of an optical fibre or similar. The fluorescence from the probes in the target zone may be collected by an optical fibre or similar. The fluorescence from the probes in the target zone may be collected by the same optical fibre that delivered the illumination light. The collected fluorescence is typically delivered to a recording device, such as a charge-coupled device (CCD) or similar. Alternatively, the fluorescence from the probes in the target zone may be directly collected by a recording device, such as a CCD or similar. For example to both deliver the probe to the target zone, to deliver light to the target area, and to detect fluorescence from the target zone. Alternatively, individual instruments may be used to deliver the probe to the target area, to deliver light to the target zone and to detect fluorescence from the target area.

For example, fluorescence may be detected from the tissue of a target area using fiber confocal fluorescence microscopy (fCFM).

The fluorophore may also be an optoacoustic fluorophore. Optoacoustic fluorophores generate ultrasound when excited by intense illumination, such as by a laser tuned to the absorption range of the fluorophore. The generated ultrasound can then be detected. Probes comprising optoacoustic fluorophores can be illuminated and detected by multispectral optoacoustic tomography (MSOT). MSOT illuminates the target zone with light pulses at multiple wavelengths and detects the acoustic waves generated by the thermoelastic expansion of the environment surrounding the optoacoustic fluorophore in response to the pulses.

Preferably, the subject is a human subject. However, the subject may be a non-human animal such as equine, ovine, bovine, canine, feline or rodent, for example.

In embodiments where the target zone is a portion of the lung of a subject, the presence of MMP in the target area may be indicative of fibrosis within the target zone.

Optical probes known in the art for detecting MMPs typically have poor stability in vivo or in samples where other proteinases are present, such as tissue lysates or samples of bodily fluids, for example, and therefore are not able to provide reliable detection of MMP. For example, optical probes have been observed to rapidly breakdown in the lung of a subject, preventing any meaningful detection of MMP in the lung. Accordingly, the provision of a method of detection of MMP in a target area using a probe that is sufficiently stable in vivo to allow reliable data to be obtained allows in situ detection of MMP, and therefore, allows detection of diseases that result in the overexpression of MMP in the locality of the diseased areas. Therefore, invasive procedures may be avoided.

In embodiments where the target zone is in a joint of a subject, the presence of MMP in the target zone may be indicative of arthritis in the target area. For example, the presence of MMP in the target zone may be indicative of osteoarthritis or rheumatoid arthritis.

The presence of MMP in the target zone may be indicative of a malignant neoplasm in the target area. A low level of MMP in the target zone may be indicative of a benign neoplasm in the target zone. Accordingly, the method of the present aspect may be a method of determining the nature of neoplasm or tumour, and may allow the nature of the neoplasm or tumour to be determined visually without requiring an invasive procedure such as a biopsy or similar.

The presence of MMP in the target zone may be indicative of the boundary between cancerous tissue and normal tissue. It is not presently possible to determine with any precision the extent of a tumour visually, and therefore, where tumours are to be removed by surgery, the visible tumour and surrounding tissue is removed in an attempt to ensure that the entire tumour is removed. This may result in more tissue being removed than is necessary, or that part of the tumour is not removed. Accordingly, the method of the present aspect may allow the detection of a tumour in a target zone, and may allow the boundary of the tumour to be determined, thereby allowing the minimum amount of tissue to be removed by surgery, thereby minimising the trauma to the subject whilst maximising the likelihood that the entire tumour has been removed.

The invention extends in a third aspect to a method of assessing a portion of tissue; the method comprising the steps:

a. applying a probe according to the first aspect to the portion of tissue;
b. illuminating the portion of tissue with an appropriate wavelength of light to excite fluorophores of the probe; and
c. determining the fluorescence intensity of probe, wherein significant fluorescence of the probe is indicative of the presence of MMP in the portion of tissue, and the presence of MMP in the portion of tissue is indicative of a disease in which MMP is expressed or overexpressed.

Significant fluorescence of the probe may be indicative of the presence of active MMP in the portion of tissue. The presence of MMP in the portion of tissue may be indicative of a disease in which MMP is activated.

Preferably, the MMP is MMP-2, and/or MMP-9 and/or MMP-13. Preferably, the MMP is MMP-9 and/or MMP-13.

The portion of tissue may be a part of a tissue sample that has been removed from a subject via biopsy or similar, for example, and the method may be carried out in vitro. The portion of tissue may be part of the subject and the method may be carried out in vivo. For example, the portion of tissue may be part of the lung, heart, liver, skin, connective tissue, or joints.

The disease may be fibrosis and the portion of tissue may comprise fibrotic tissue. The disease may be a cancer and the portion of tissue may comprise a tumour or neoplasm. The disease may be arthritis.

The determination of the presence of MMP in the portion of tissue may allow a clinician to determine whether the subject has active fibroproliferation. The determination of the activity of MMP in the portion of tissue may allow a clinician to determine whether the subject has active fibroproliferation. Accordingly, the method may be a method of determining whether a subject has fibrosis, or clinically active fibrosis. The determination of the presence of MMP in the portion of tissue may allow a clinician to determine whether the subject has cancer. Accordingly, the method may be a method determining whether a subject has cancer. The determination of the presence of MMP in the portion of tissue may allow a clinician to determine whether the subject has arthritis. Accordingly, the method may be a method determining whether a subject has arthritis. The determination of the presence of MMP in the portion of tissue may allow a clinician to determine whether the subject has cirrhosis. Accordingly, the method may be a method determining whether a subject has cirrhosis.

Preferred and optional features of the first and second aspects are preferred and optional features of the second aspect.

In some embodiments, portions of tissue may be known to comprise a neoplasm or tumour. Lack of a significant fluorescence of the probe may be indicative of a benign neoplasm. A significant fluorescence of the probe may be indicative of a malignant neoplasm.

The location of fluorescent probes may be indicative of the boundary between cancerous tissue and normal tissue, and therefore, the method of the invention may allow the extent of the cancerous tissue to be determined. Accordingly, an appropriate portion of tissue for surgical removal may be determined, and may thereby allow the minimum tissue to be removed whilst maximising the chance that all cancerous tissue is removed.

According to a fourth aspect of the invention, there is provided a kit of parts comprising the probe according to the first aspect in a suitable diluent or buffer.

Embodiments of the present invention will now be described, by way of non-limiting example, with reference to the accompanying drawings.

SPECIFIC DESCRIPTION OF EMBODIMENTS OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Enzyme Cleavable Peptide Sequence Optimization as MMP-2/9 Substrate

Generating molecular probe sequences to optimally measure the MMP-2/9 activity: The initial activatable probes contain a fluorophore and a quencher bonded to an amino acid sequence that is cleavable by the target enzyme (acting as an enzyme cleavable peptide sequence). In the inactive state, the emission from the fluorophore moiety is absorbed by the quencher by fluorescence resonance energy transfer (FRET), but in the presence of the target enzyme, the amino acid sequence is cleaved, separating the fluorophore from the quencher, and thereby causing a remarkable increase in fluorescence.

Initial substrate G-P-K-G-L-K-G (SEQ ID NO.1) was selected according to Proteomics studies [Mol. and Cell. Proteomics 2010, 9, 894-911].

Figure 1:
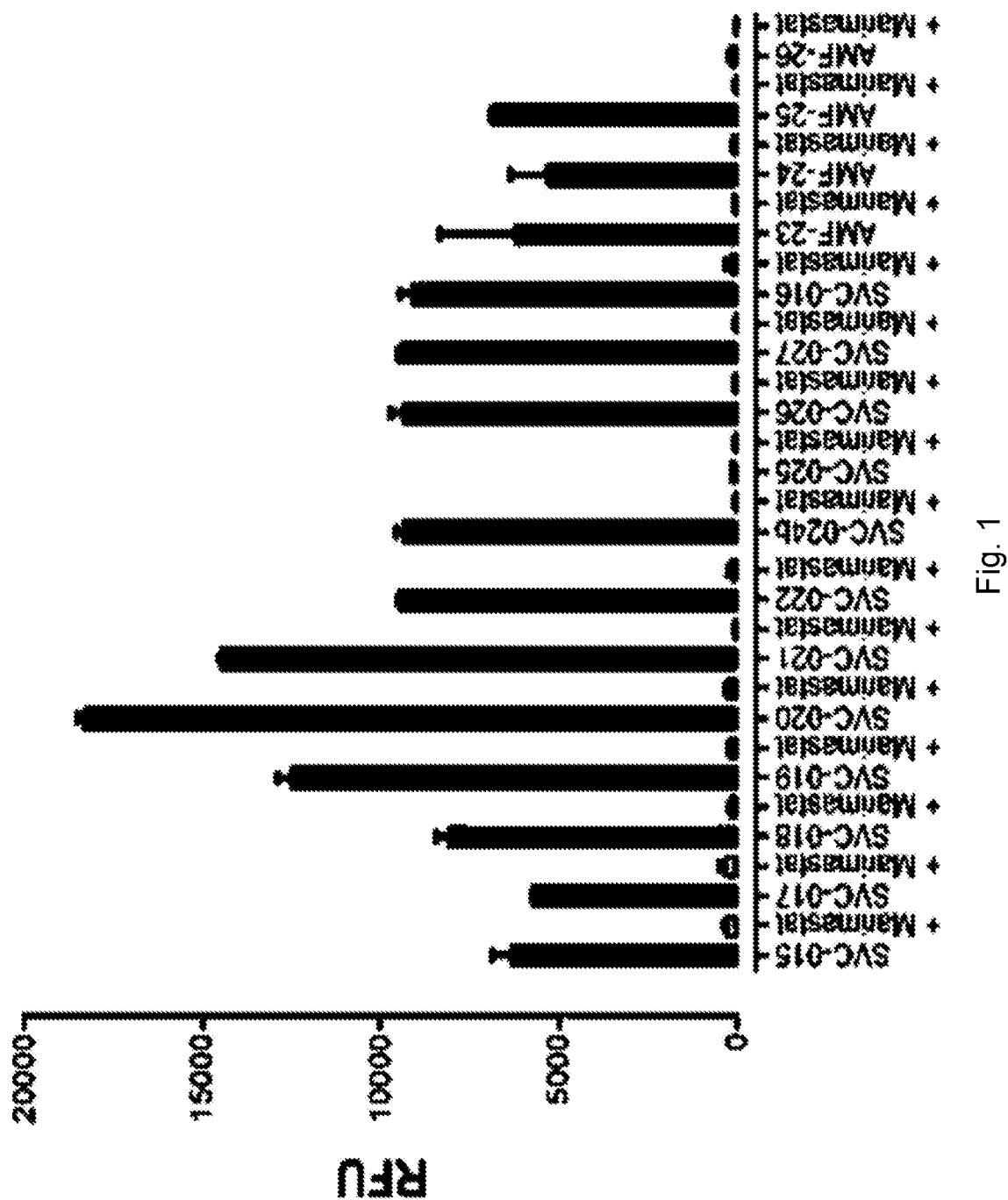
FIG. 1. Probe fluorescence (ex 485 nm/em 528 nm) was measured for all FRET monomers (10 µM) with MMP-9 (30 nM) in the absence or presence of Marimastat (20 µM).

A library of probes (listed in Table 2 below) containing FAM (Carboxyfluorescein) as the fluorophore (donor) and MethylRed (MR) as the quencher (acceptor) and a variety of peptide sequences was synthesized by manual standard solid-phase Fmoc peptide chemistry (described below). The specificity for MMP of the probes was evaluated by measuring the fluorescence of the probes in the presence of MMP-9 and in absence or presence of the MMP suppressor Marimastat, and the results are shown in FIG. 1.

TABLE 2

| Probe Structures | Code |
|---|---|
| FAM-PEG$_2$-G-P-K-G-L-K-G-K(MR)-NH$_2$ | SVC-01-024/ SVC-024b, c |
| FAM-PEG$_2$-G-P-K-G-DL-K-G-K(MR)-NH$_2$ | SVC-01-025/ SVC-025, b |
| FAM-PEG$_2$-G-P-K-G-I-K-G-K(MR)-NH$_2$ | SVC-01-026/ SVC-026 |

TABLE 2-continued

| Probe Structures | Code |
|---|---|
| FAM-PEG$_2$-G-P-K-G-Nle-K-G-K(MR)-NH$_2$ | SVC-01-027/ SVC-027 |
| FAM-PEG$_2$-P-Cha-G-M-F-G-K(MR)-NH$_2$ | SVC-01-015/ SVC-015 |
| FAM-PEG$_2$-P-F-G-M-K-βA-K(MR)-NH$_2$ | SVC-01-016/ SVC-016/ SVC-069 |
| FAM-PEG$_2$-P-F-G-L-K-βA-K(MR)-NH$_2$ | AMF-23 |
| FAM-PEG$_2$-P-F-G-I-K-βA-K(MR)-NH$_2$ | AMF-24 |
| FAM-PEG$_2$-P-F-G-Nle-K-βA-K(MR)-NH$_2$ | AMF-25 |
| FAM-PEG$_2$-P-F-G-DM-K-βA-K(MR)-NH$_2$ | AMF-26 |
| FAM-PEG$_2$-P-Cha-G-M-W-G-K(MR)-NH$_2$ | SVC-01-017/ SVC-017 |
| FAM-PEG$_2$-P-Cha-G-M-Y(Me)-G-K(MR)-NH$_2$ | SVC-01-018/ SVC-018 |
| FAM-PEG$_2$-P-Cha-G-M-Y-G-K(MR)-NH$_2$ | SVC-01-019/ SVC-019 |
| FAM-PEG$_2$-P-Cha-G-M-K-βA-K(MR)-NH$_2$ | SVC-01-020/ SVC-020 |
| FAM-PEG$_2$-P-Cha-G-M-H-G-K(MR)-NH$_2$ | SVC-01-021/ SVC-021 |
| FAM-PEG$_2$-P-Cha-G-M-K-G-K(MR)-NH$_2$ | SVC-01-022/ SVC-022 |

Figure 2:
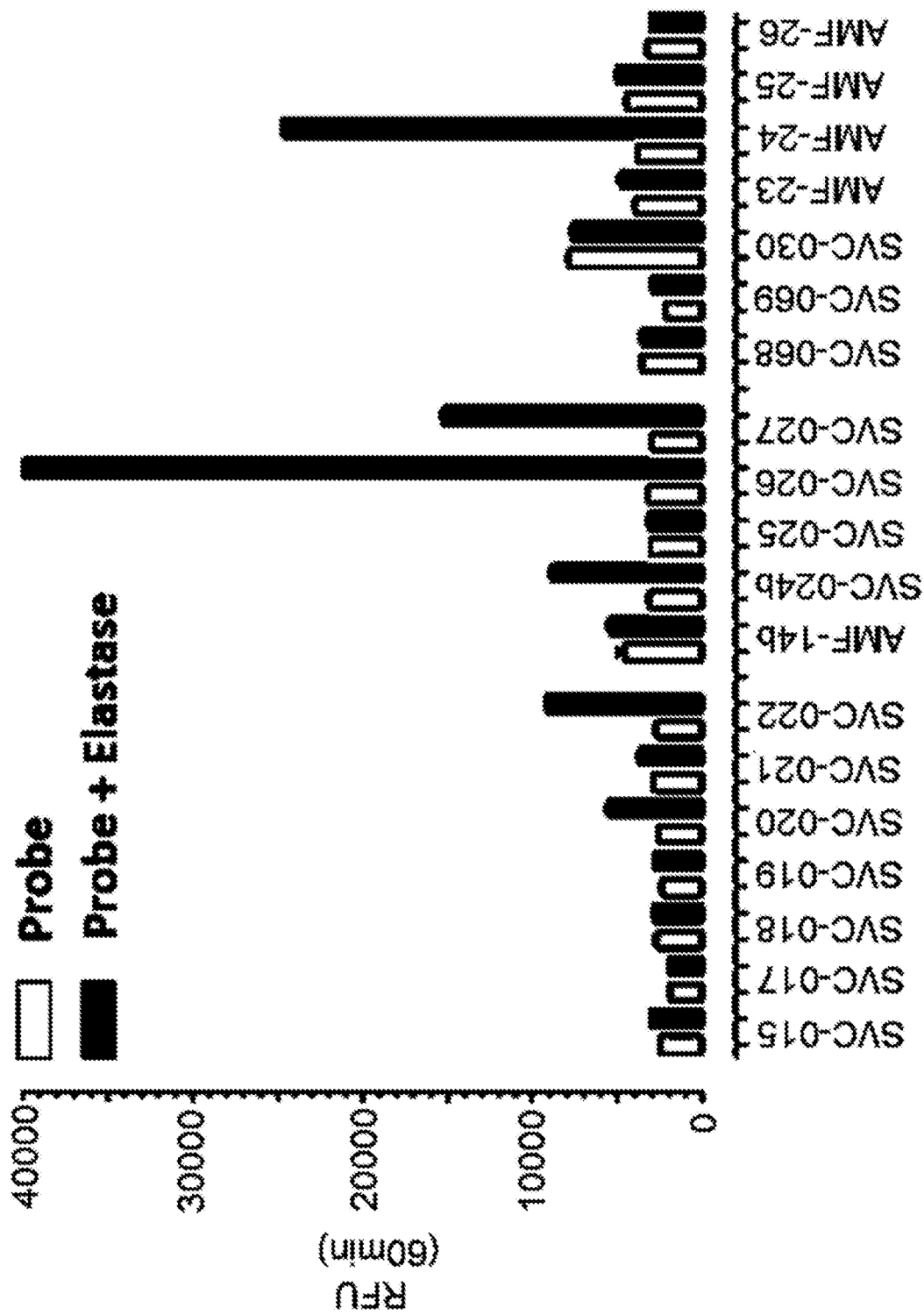
FIG. 2. Probe fluorescence (ex 485 nm/em 528 nm) was measured after 5 min for all FRET monomers (10 µM) in the absence and presence of Elastase (30 nM).

The selectivity of the probes, together with further probes AMF-14b, SVC-030 (both defined in Table 6 below) and SVC-068 (defined in Table 4 below), to detect MMP over elastase, another proteinase relevant in lung disease, was tested and the results for all probes are shown in FIG. 2.

Figure 3A:
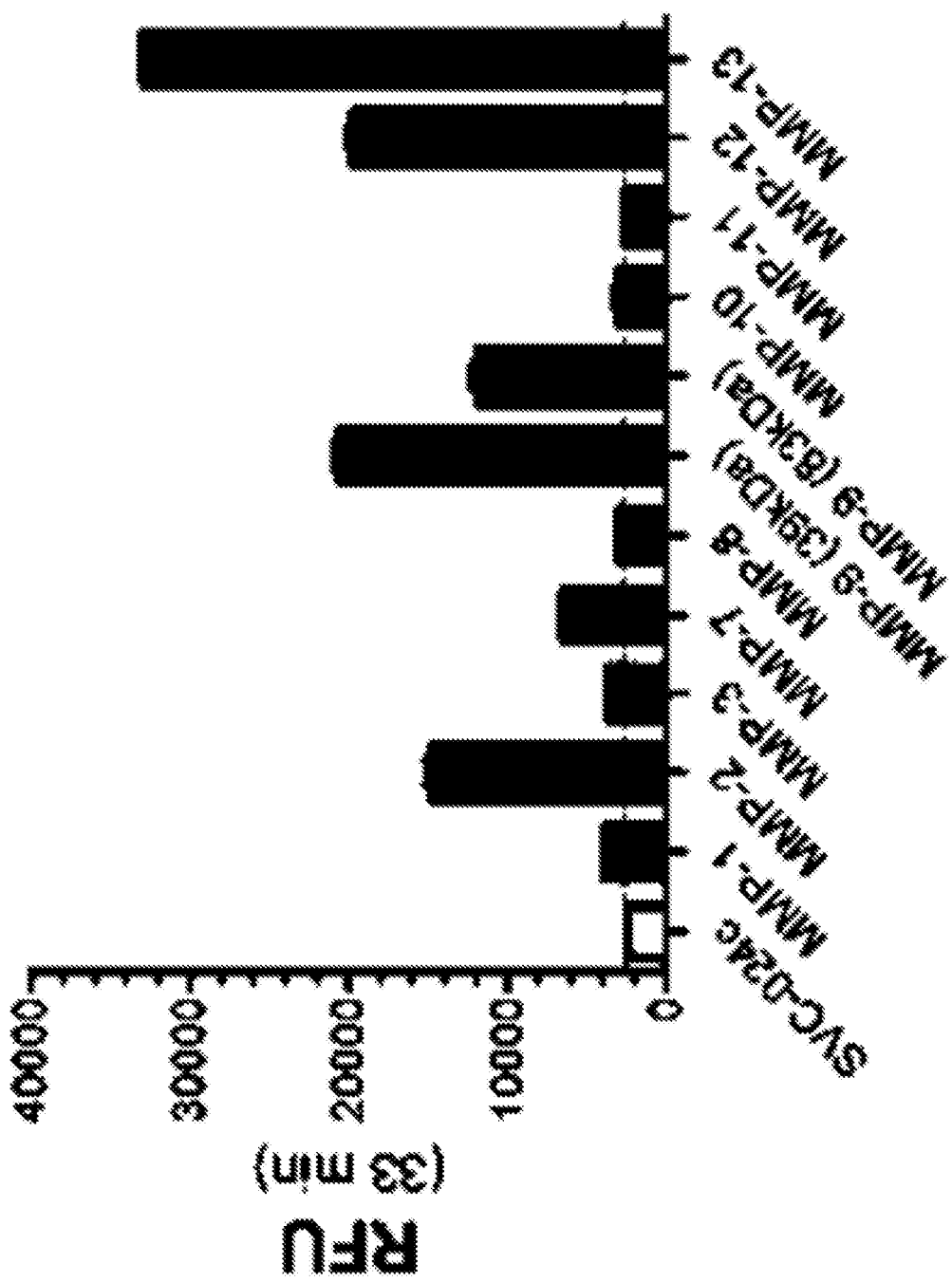
FIG. 3. Probe fluorescence (ex 485 nm/em 528 nm) was measured for FRET monomers (10 µM) with MMPs (30 nM); (A) Probe SVC-24: FAM-PEG$_2$-G-P-K-G-L-K-G-K (MR)-NH$_2$; (B) Probe SVC-25 (Control): FAM-PEG$_2$-G-P-K-G-(D)L-K-G-K(MR)-NH$_2$ (Red dotted line represents background fluorescence for each probe).
Figure 3B:
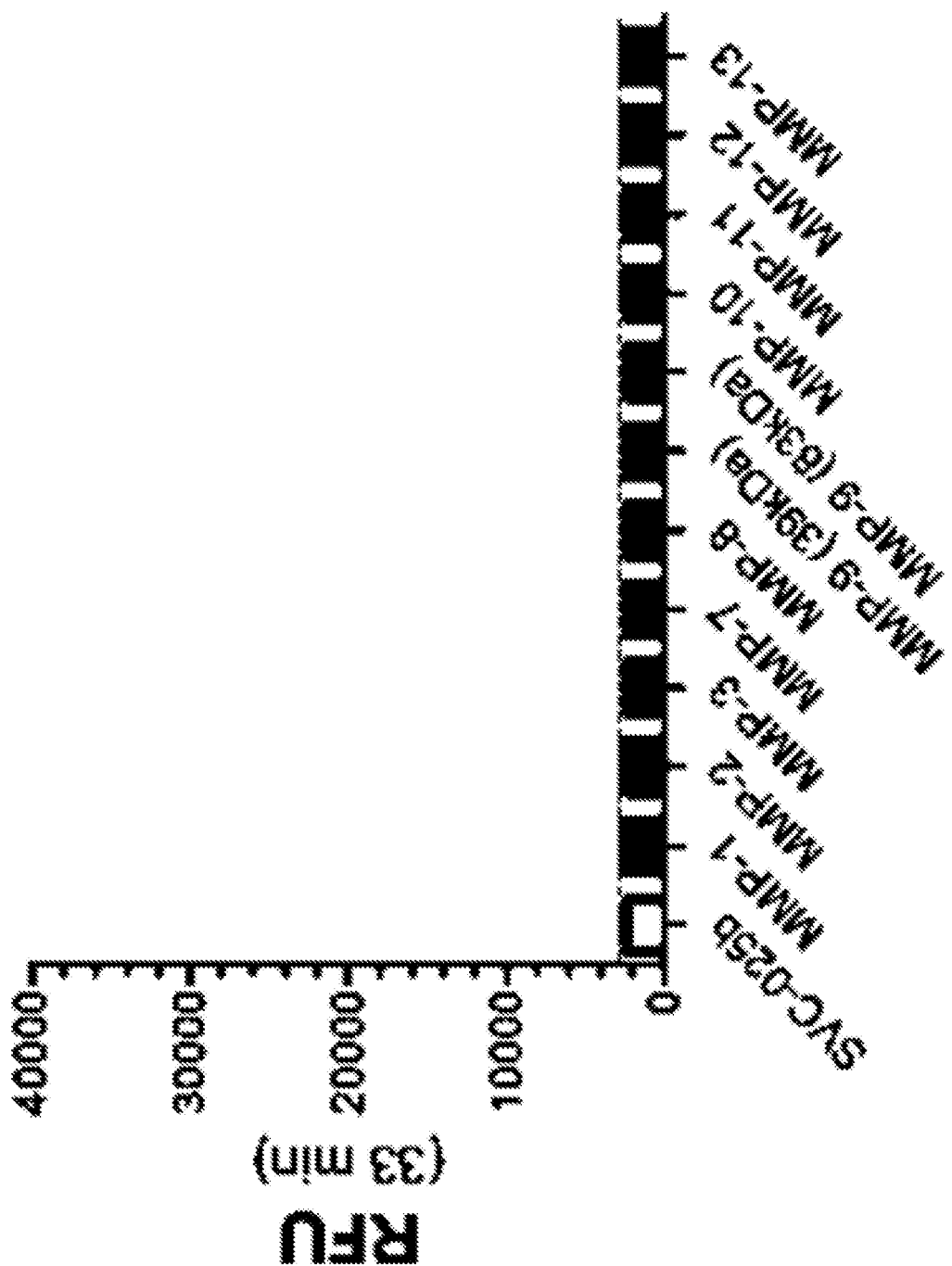

Enzyme specificity of the lead probes with exogenous enzymes was tested using a multiwell plate fluorimeter at excitation/emission 485/528 nm (Table 3). Recombinant human catalytic domain MMPs-1, -2, -3, -7, -8, -9, -10, -11, -12, -13 were used at 30 nM. Cleavage site for each sequence is indicated in italics. For probe SVC-24, results are shown in FIG. 3A as SVC-24c. For probe SVC-025, results are shown in FIG. 3B as SVC-25b.

TABLE 3

| | | Inflammatory mediators | | | | | | |
|---|---|---|---|---|---|---|---|---|
| Probe code | Probe sequence | MMP-9 (39.0 kDa) | MMP-2 (20.3 kDa) | MMP-12 (20.3 kDa) | MMP-13 (20.4 kDa) | Neutrophil lysate | Neutrophil lysate | Thrombin |
| SVC-24/ SVC24b | -G-P-K-G-L-K-G- | 3.50 | 1.98 | 2.34 | 9.30 | 1.93 | 1.30 | 1.31 |
| SVC-26 | -G-P-K-G-Ile-K-G- | 4.22 | 2.10 | 1.54 | 9.33 | 13.49 | 11.97 | 1.37 |
| SVC-27 SVC-69/ | -G-P-K-G-Nle-K-G- | 4.53 | 2.70 | 1.46 | 11.75 | 3.06 | 1.97 | 1.48 |
| SVC-16 | -P-F-G-M-K-βA- | 5.21 | 3.11 | 1.88 | 13.57 | 1.07 | 1.06 | 0.99 |
| AMF-23 | -P-F-G-L-K-βA- | 2.50 | 1.87 | 3.03 | 6.41 | 0.99 | 0.10 | 0.89 |
| AMF-24 | -P-F-G-Ile-K-βA- | 2.29 | 1.59 | 1.65 | 5.05 | 3.29 | 2.25 | 0.96 |
| AMF-25 | -P-F-G-N/e-K-βA- | 2.02 | 1.88 | 1.53 | 5.27 | 0.96 | 0.99 | 0.96 |

TABLE 3-continued

Inflammatory mediators

| Probe code | Probe sequence | MMP-9 (39.0 kDa) | MMP-2 (20.3 kDa) | MMP-12 (20.3 kDa) | MMP-13 (20.4 kDa) | Neutrophil lysate | Neutrophil lysate | Thrombin |
|---|---|---|---|---|---|---|---|---|
| SVC-15 | -P-Cha-G-M-F-G- | 5.89 | 3.27 | 2.45 | 11.75 | 2.02 | 1.07 | 0.94 |
| SVC-17 | -P-Cha-G-M-W-G--P-Cha-G-M- | 5.07 | 2.59 | 2.59 | 6.5 | 0.84 | 1.04 | 1.05 |
| SVC-18 | Y(Me)-G- | 4.94 | 2.54 | 2.15 | 10.04 | 0.75 | 1.00 | 0.97 |
| SVC-19 | -P-Cha-G-M-Y-G- | 6.90 | 4.07 | 2.87 | 11.26 | 1.89 | 1.08 | 1.04 |
| SVC-20 | -P-Cha-G-M-K-βA-G- | 9.61 | 5.22 | 3.21 | 15.9 | 1.40 | 1.19 | 1.00 |
| SVC-21 | -P-Cha-G-M-H-G- | 7.53 | 4.01 | 3.05 | 12.93 | 1.27 | 1.08 | 0.97 |
| SVC-22 | -P-Cha-G-M-K-G- | 8.21 | 4.24 | 2.61 | 14.88 | 1.95 | 1.44 | 1.02 |

An increase in fluorescence was observed with MMP-9 and site specific cleavage, as revealed by MALDI, was confirmed for all the sequences. The other MMPs tested shared the same cleavage site. Control probes (containing the sequences -G-P-K-G-(D)L-K-G- and -P-F-G-(D)M-K-βA-) with D-amino acids in the cleavage site were tested and no increase in fluorescence was observed.

Specific inhibition of fluorescence signal using Marimastat was successful for all of the probes. In order to choose the best probes for our application, additional parameters were characterized and compared. The fluorescence increase in presence of other related enzymes (Thrombin, Elastase), macrophages, and bronchoalveolar lung lavage fluid (BALF) was also measured and used as a selection criteria. Despite the positive results for probes containing Methionine in the cleavage site, these probes were avoided due to potential stability problems caused by sulphide oxidation. The best probes were also evaluated in an ex vivo assay with human tissue homogenate confirming only specific cleavage and inhibition with Marimastat for -G-P-K-G-L-K-G-K(MR)- (SEQ ID NO.15) and -P-F-G-Nle-K-βA-K(MR)- (SEQ ID NO.16). In each case, the enzyme cleavable peptide sequence that is specifically cleaved by MMP is shown in bold. All assays were carried out using FRET monomers (i.e. they comprise one probe element) to overcome ineffectiveness of the final MMP probes due to poor specificity and in vivo stability, one of the main difficulties found when applying a probe in vivo.

Control probes are listed in Table 4 below containing FAM (Carboxyfluorescein) as the fluorophore (donor), MethylRed (MR) as the quencher (acceptor) and a variety of peptide sequences. The control probes were synthesized by manual standard solid-phase Fmoc peptide chemistry (described below). SVC-068 is an oxidised version of SVC-01-16, which contains methionine in the cleavable sequence. Oxidation of SVC-01-16 introduces a S=O group. It is apparent from a FIG. 2 that the oxidised cleavable sequence was not recognised by MMP.

TABLE 4

| Probe Structures | Code |
|---|---|
| FAM-PEG$_2$-P-F-G-M(S = O)-K-βA-K(MR)-NH$_2$ | SVC-01-68/ SVC-068 |

TABLE 4-continued

| Probe Structures | Code |
|---|---|
| FAM-PEG$_2$-G-p-k-G-L-k-G-K(MR)-NH$_2$ | AMF-73 |
| FAM-PEG$_2$-G-p-k-G-I-k-G-K(MR)-NH$_2$ | AMF-74 |
| FAM-PEG$_2$-G-G-G-G-G-K(MR)-NH$_2$ | ETA-12 |

Synthesising aqueous soluble molecular probes: The two selected sequences A and B were implemented in new probes flanked by ethylenglycol units and Lys residues to increase the solubility. Good results were achieved with alternate D-Lys and PEG units.

A number of structural modifications were carried out to improve the solubility of the probes, and to determine the optimal fluorophores and quenchers to be used.

Solubility:

Different linker/spacer composition consisting of hydrophilic/hydrophobic or charged groups: ethylenglycol units (PEG), L-Lysine, and alternative ethylenglycol units (PEG) and D-Lysine were generated. The linkers improve the aqueous solubility of the compounds. The presence of unnatural D-aminoacid improves the in vivo stability of the compounds making them resistant to proteolysis. Furthermore, this allowed greater understanding of the effect of linkers on structure and function of the probes.

Figure 13:
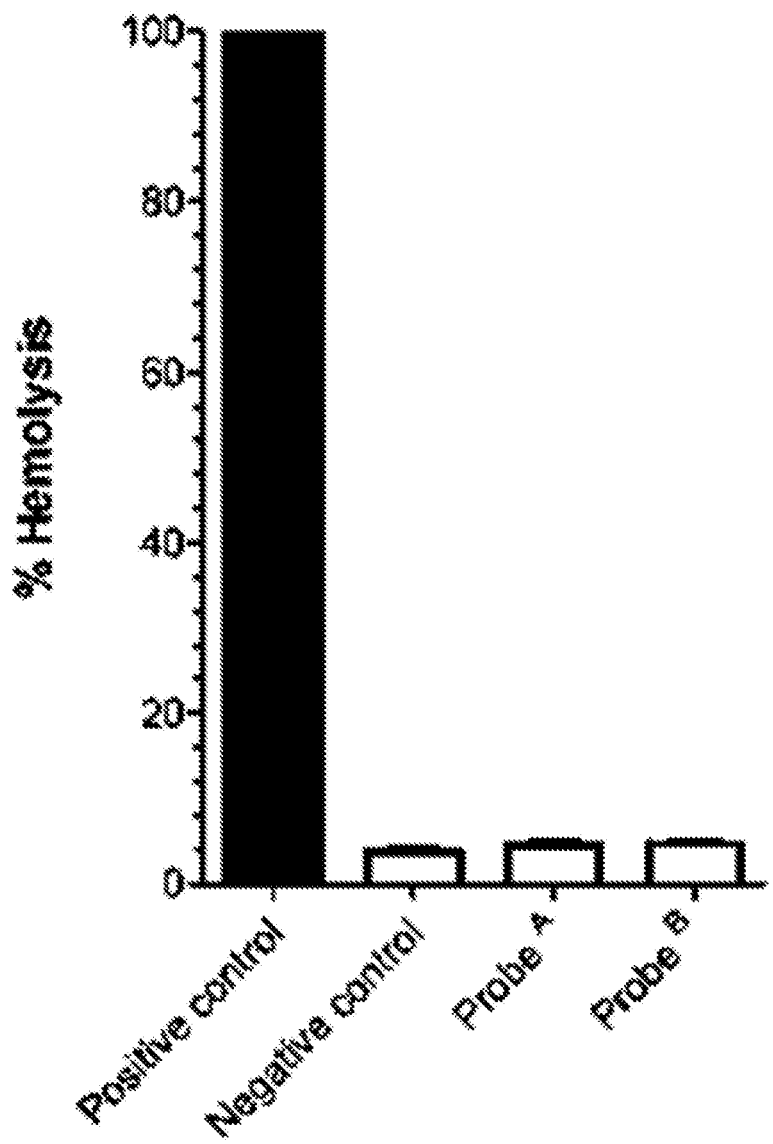
FIG. 13. Haemolytic assay of molecular probes A and B. The haemolytic activity of the molecular probes was evaluated in human red blood cells.
Figure 14:
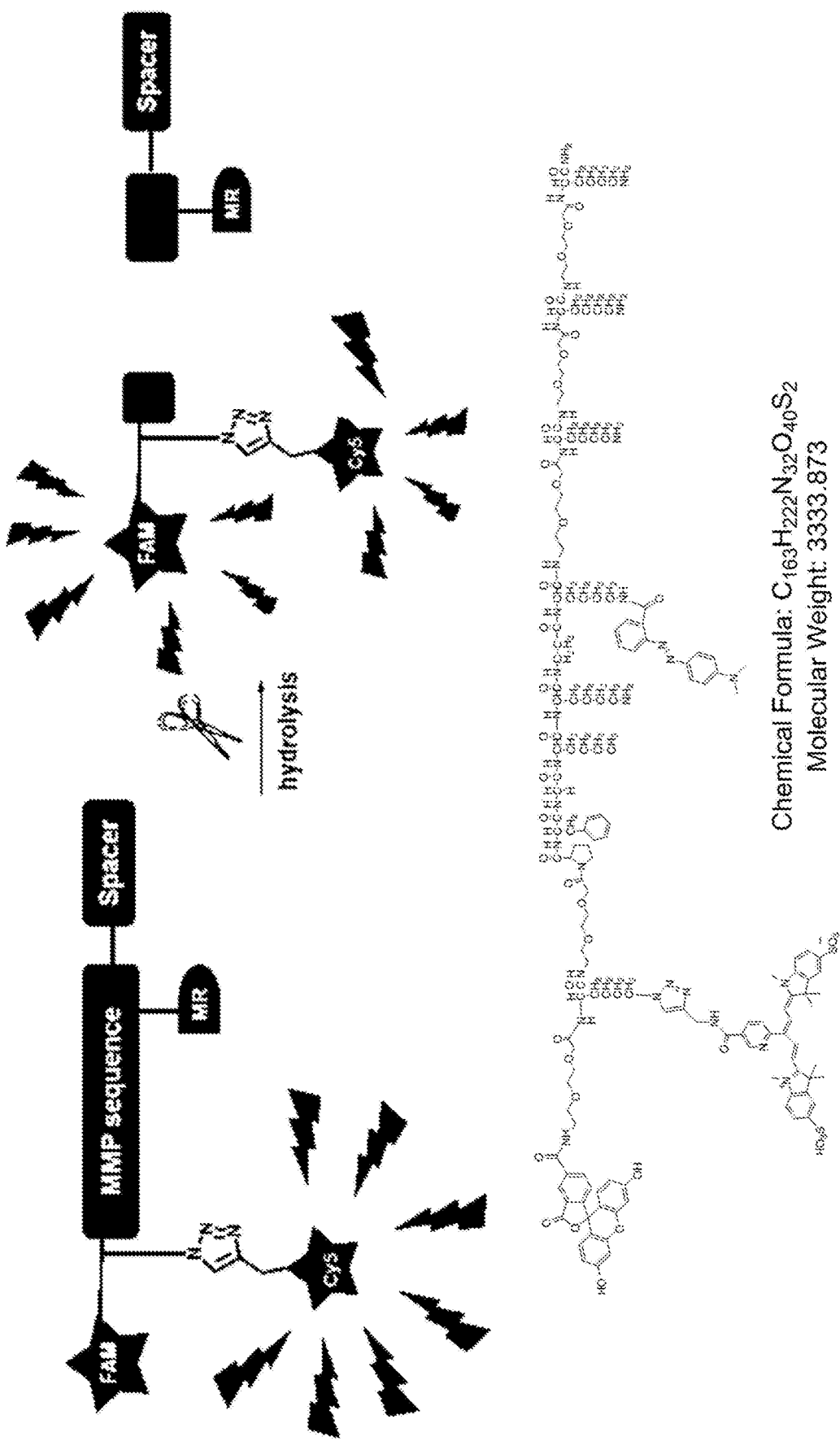
FIG. 14. An example of a probe according to one embodiment of the invention. The probe comprises one reporter fluorophore that is not substantially quenched plus a FRET pair.

Expansion of Fluorophore and FRET System:

Various fluorophores, including FAM, Cy5 and carboxy naphthofluorescein (NF), and quenchers (MR, BHQ-1/3 and QSY-21) labelled on optimised sequences to expand the scope of probe, not limited to, near infrared range (i.e. probes that emit radiation having a wavelength of ~0.75-1.4 µm) with the aim of producing a higher signal-to-noise ratio, which may enable lower levels of MMP detection at lower effective probe concentrations and to rule out the non-specific activation by introducing additional label which is aimed to be as a reference dye (for example, see FIG. 13). Example structures are shown in Table 5 below, where "-k-" represents "-(D)-Lysine-".

Probe SVC-01-180 in Table 5 below is a polymerisable probe containing an ethylenically unsaturated monomer moiety. This can be polymerised in the presence of water to form a hydrogel and is discussed in more detail below.

TABLE 5

| Probe Structures | Code |
|---|---|
| FAM-PEG$_2$-G-P-K-G-L-K-G-K(MR)-K-K-PEG$_2$-PEG$_2$-NH$_2$ | AMF-91 |
| FAM-PEG$_2$-P-F-G-Nle-K-βA-K(MR)-K-K-PEG$_2$-PEG$_2$-NH$_2$ | AMF-92 |
| FAM-PEG$_2$-G-P-K-G-(D)L-K-G-K(MR)-K-K-PEG$_2$-PEG$_2$-NH$_2$ | ODHS-1 |
| FAM-PEG$_2$-G-P-K-G-L-K-G-K(MR)-PEG$_2$-PEG$_2$-NH$_2$ | AMF-96 |
| FAM-PEG$_2$-P-F-G-Nle-K-βA-K(MR)-PEG$_2$-PEG$_2$-NH$_2$ | AMF-97 |
| MR-K(Ac)-PEG$_2$-GPKGLKG-K(FAM)-PEG$_2$-k-PEG$_2$-k-PEG$_2$-k-NH$_2$ | AMF-111 |
| QSY21-K(PEG-N$_3$)-PEG$_2$-GPKGLKG-K(Cy5)-PEG$_2$-k-PEG$_2$-k-PEG$_2$-k-NH$_2$ | AMF-140 |
| FAM-PEG$_2$-GPkGLkGK(MR)-PEG$_2$-k-PEG$_2$-k-NH$_2$ | SVC-01-181DD |
| FAM-PEG$_2$-GPkGLKGK(MR)-PEG$_2$-k-PEG$_2$-k-NH$_2$ | SVC-01-181DL |
| MR-PEG$_2$-P-F-G-Nle-K-βA-K(FAM)-PEG$_2$-k-PEG$_2$-k-PEG$_2$-k-NH$_2$ | AMF-154-01 |
| QSY21-PEG$_2$-P-F-G-Nle-K-βA-K(Cy5)-PEG$_2$-k-PEG$_2$-k-PEG$_2$-k-NH$_2$ | AMF-154-02 |
| QSY21-PEG$_2$-P-F-G-Nle-K-βA-K(naphthofluorescein)-(PEG$_2$-k)3-NH$_2$ | SVC-02-008 |
| QSY21-K(PEG-N$_3$)-PEG$_2$-P-F-G-Nle-K-βA-K(Cy5)-PEG$_2$-k-PEG$_2$-k-PEG$_2$-k-NH$_2$ | AMF-154-03 |
| QSY21-K(N$_3$)-PEG$_2$-P-F-G-Nle-K-βA-K(Cy5)-PEG$_2$-k-PEG$_2$-k-PEG$_2$-k-NH$_2$ | AMF-181 |
| QSY21-K(N$_3$)-PEG$_2$-P-F-G-(D)Nle-K-βA-K(Cy5)-PEG$_2$-k-PEG$_2$-k-PEG$_2$-k-NH$_2$ | AMF-199 |
| FAM-PEG$_2$-K(tzCy5)-PEG$_2$-P-F-G-Nle-K-βA-K(MR)-[PEG$_2$-k]$_3$-NH$_2$ | AMF-210 |
| Cy5-K-(DBCO)-PEG$_2$-G-P-K-G-L-K-G-K(BHQ-3)-PEG$_2$-k-PEG$_2$-k-PEG$_2$-k-NH$_2$ | SVC-01-161 |
| MR-K(Acryloyl)-PEG$_2$-G-P-K-G-L-K-G-K(FAM)-PEG$_2$-k-PEG$_2$-k-NH$_2$ | SVC-01-180 SVC-180 |

Variants consisting of D-amino acids at the recognition site sequence with or without blocking PEG units were also synthesised and assessed. The D-amino acid variants as well as the variants with PEG or acetyl blocking groups at the ends of the peptide sequence exhibited reduced activation by MMP in vitro.

A number of further structural modifications were carried out to improve the signal-to-noise ratio and to improve the structural stability of the probes in vivo, and the structures tested are shown in Table 6 below:

TABLE 6

| Probe Structures | Code |
|---|---|
| FAM-Ahx-G-P-K-G-L-K-G-3 probe elements | TWB-140 |
| FAM-Ahx-G-P-K-G-L-K-G-K(MR)-3 probe elements | AMF-14/AMF-14b |
| FAM-PEG$_2$-P-F-G-M-K-βA-K(MR)-NH-3 probe elements | SVC-01-030/ SVC-030 |
| FAM-PEG$_2$-G-P-K-G-L-K-G-K(MR)-PEG$_2$-k-PEG$_2$-k-3 probe elements | AMF-106 |
| FAM-PEG$_2$-PFGNleKβA-PEG$_2$-k-PEG$_2$-k-3 probe elements | SVC-01-188 |
| FAM-PEG$_2$-PFGNleKβA-K(MR)-PEG$_2$-k-PEG$_2$-k-3 probe elements | SVC-01-186/194 |
| FAM-K(FAM)-PEG$_2$-PFGNleKβA-PEG$_2$-k-PEG$_2$-k-3 probe elements | SVC-01-189 |
| FAM-PEG$_2$-PFGNleKβA-K[K(MR)$_2$]-PEG$_2$-k-PEG$_2$-k-3 probe elements | SVC-01-187/195 |
| FAM-K(FAM)-PEG$_2$-PFGNleKβA-K(FAM)-PEG$_2$-k-PEG$_2$-k-3 probe elements | SVC-01-196 |
| Ac-PEG$_2$-PFGNleKβA-K(FAM)-PEG$_2$-k-PEG$_2$-k-3 probe elements | SVC-01-197 |
| Ac-PEG$_2$-PFGNleKβA-K[K(FAM)$_2$]-PEG$_2$-k-PEG$_2$-k-3 probe elements | SVC-01-198 |

TABLE 6-continued

| Probe Structures | Code |
|---|---|
| FAM-K(FAM)-PEG$_2$-PFGNleKβA-K(MR)-PEG$_2$-k-PEG$_2$-k-3 probe elements | SVC-02-026 |
| FAM-K(FAM)-PEG$_2$-k-PEG$_2$-k-PFGNleKβA-PEG$_2$-3 probe elements | AMF-164 |
| FAM-PEG$_2$-k-PEG$_2$-k-K(FAM)-PFGNleKβA-PEG$_2$-3 probe elements | AMF-165 |
| NBD-PEG$_2$-PFGNleKβA-K(MR)-PEG$_2$-k-PEG$_2$-k-3 probe elements | SVC-02-030 |
| [FAM-PEG$_2$-PFGNleKβA]3 probe elements-Lys(MR)-PEG$_2$-k-PEG$_2$-K(Alkyne)-NH$_2$ | AMF-212 |

Figure 4:
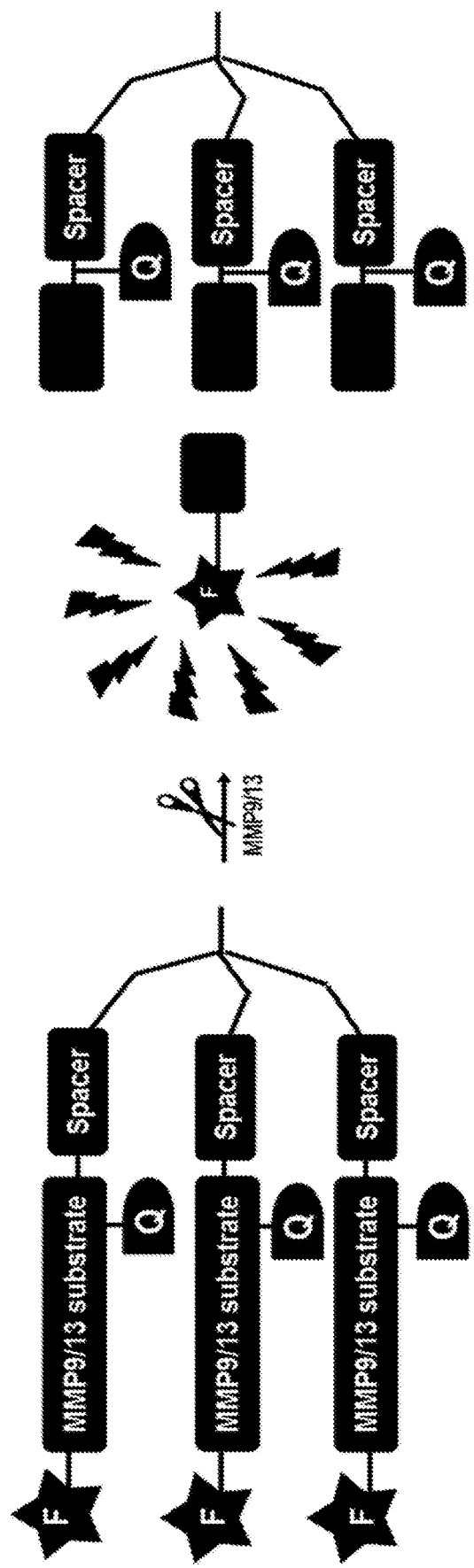
FIG. 4. An illustration of how probes according to an embodiment of the invention comprising three probe elements fluoresce in the presence of MMP-9 and MMP-13.
Figure 5:
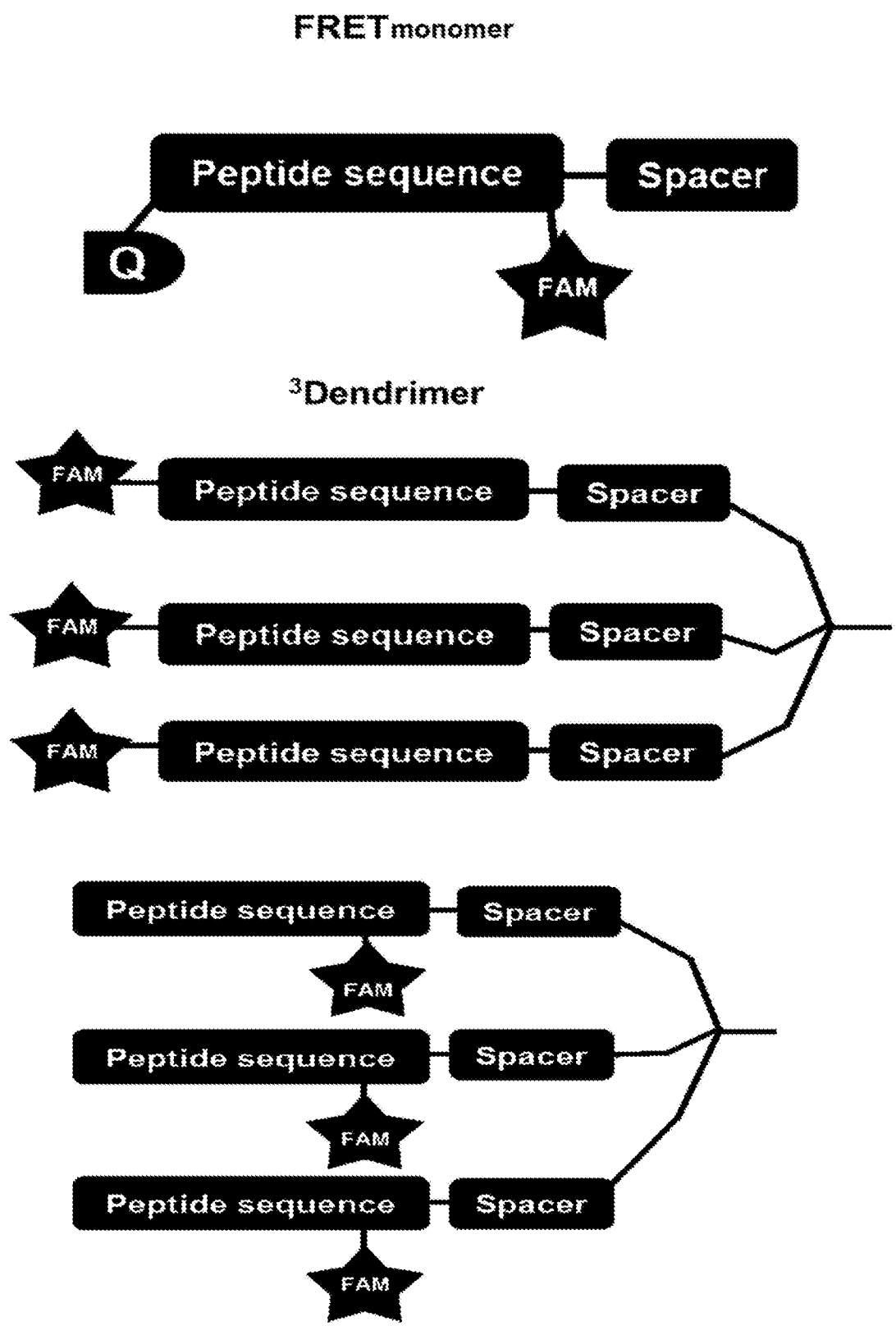
FIG. 5. Schematic illustrations of examples of probes according to embodiments of the invention.
Figure 5:
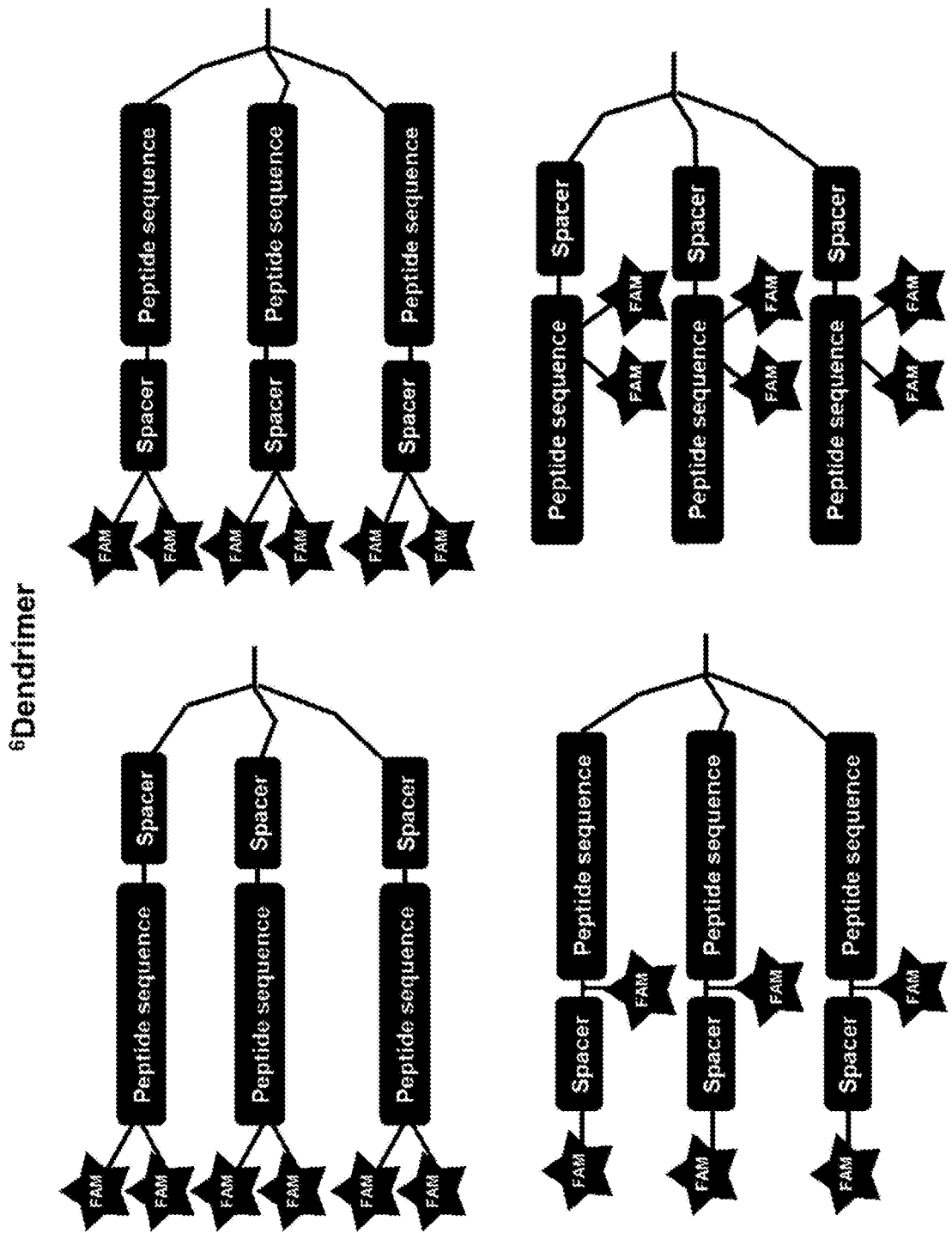
Figure 5:
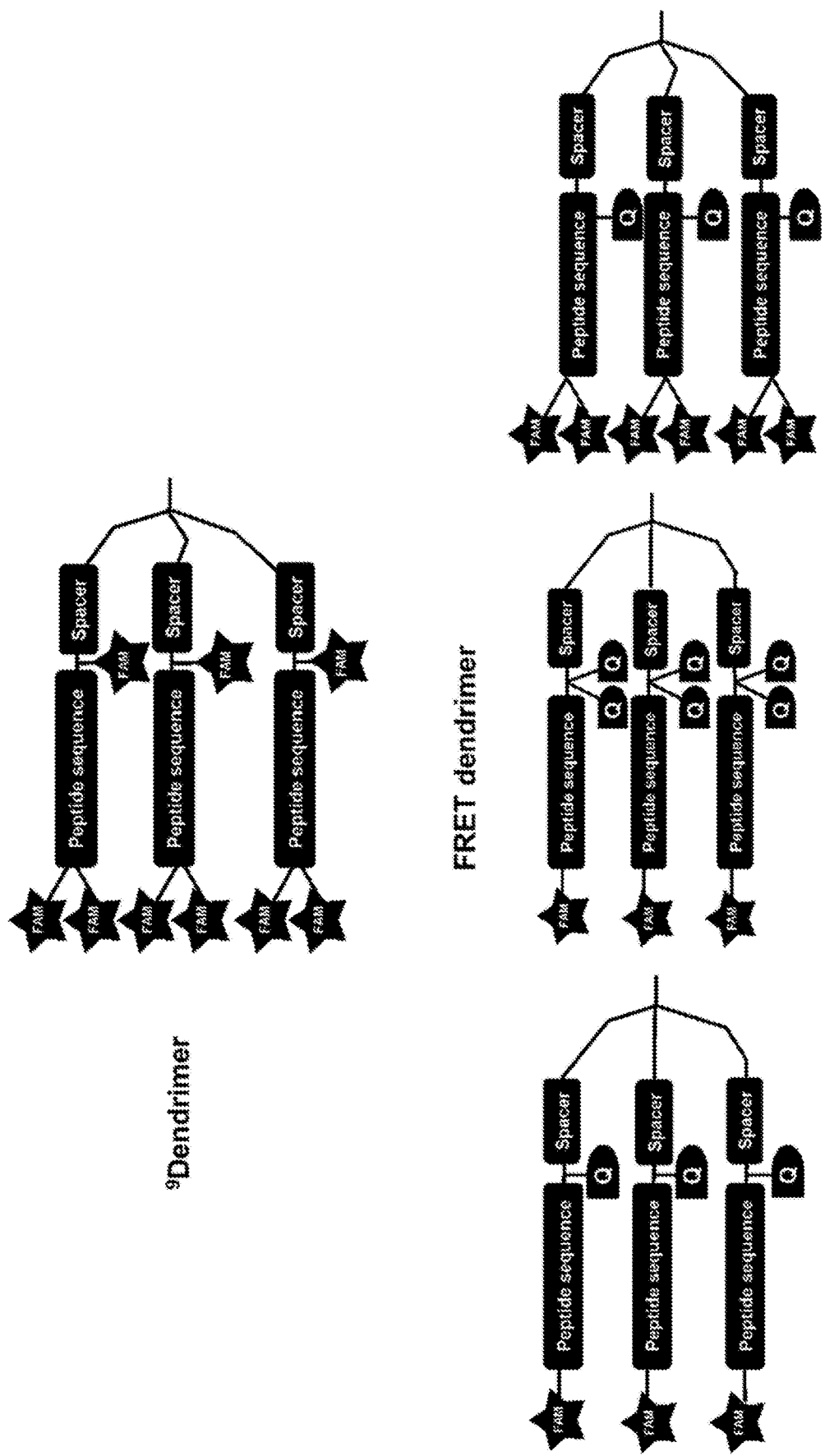
Figure 6:
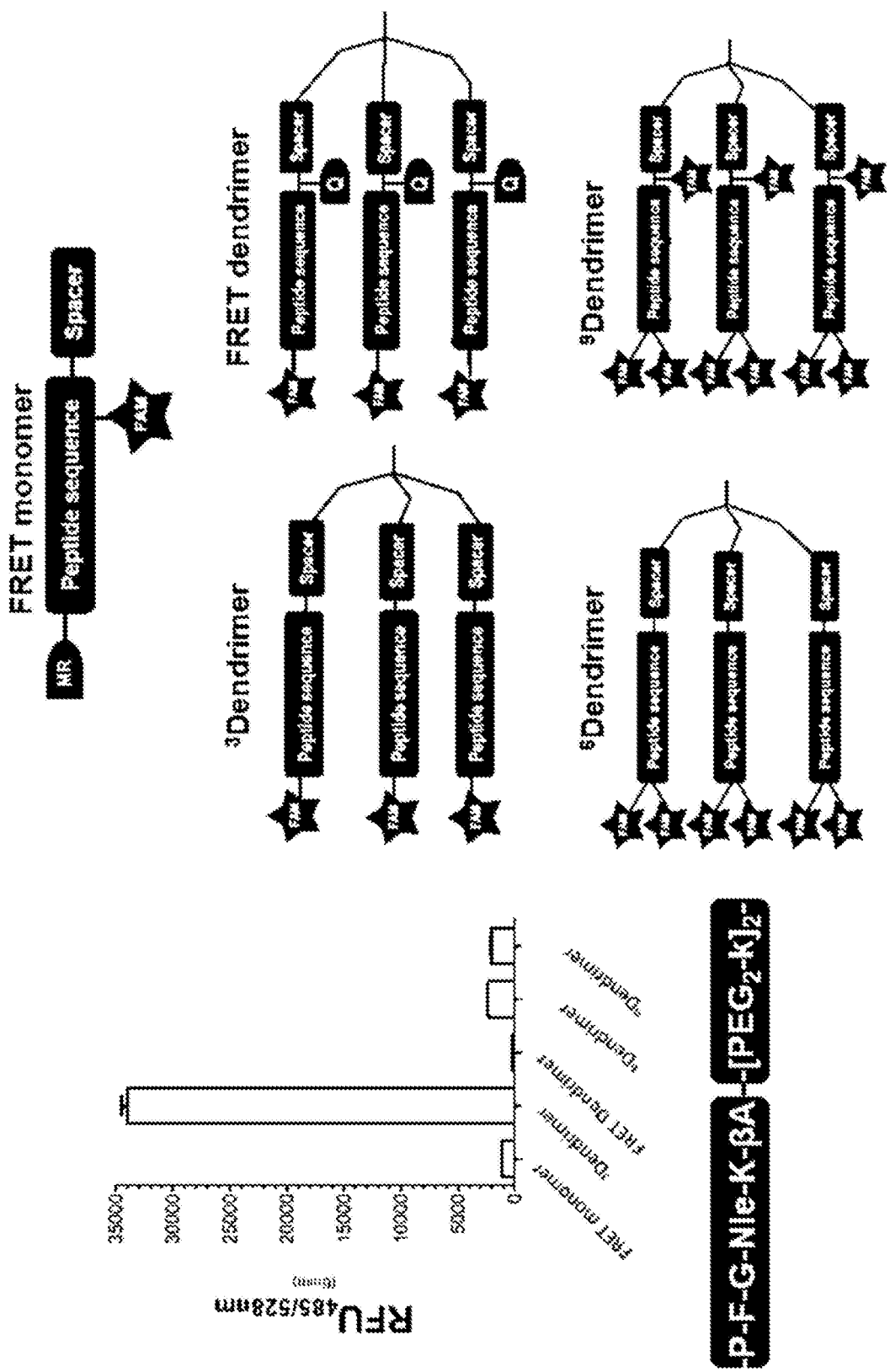
FIG. 6. Probe Background: Background fluorescence signal for MMP probes. Probes at 10 µM were incubated at 37° C. in MMP buffer and assessed in a fluorimeter (Synergy H1 Hybrid Reader, BioTek instruments Ltd) at excitation/emission 485/528 nm. Signal was shown as relative fluorescence units after 6 min. The scaffold structure and the number/position of fluorophores and quenchers has an important effect in the quenching efficiency and therefore in the fluorescent background signal.

Branched Probe:

Increase the signal-to-noise ratio by examining different probe scaffold designs, change of fluorophore positions, spacer length and location between the fluorophore-quencher or increasing the fluorophore (FAM) or quencher (MethylRed, BHQ-1/3, or QSY-21) number per probe element. FIG. 4 shows how a probe comprising three probe elements, or "branches" fluoresces in the presence of MMP-9 or MMP-13. FIG. 5 shows schematic illustrations of a number of different probe structures, including a linear probe ("FRET monomer"), branched probes comprising three probe elements ("3Dendrimer", "6Dendrimer" and "9Dendrimer", where the number indicates the number of fluorophores in total in the probe) and branched probes comprising three probe elements comprising fluorophores and quenchers ("FRET dendrimer").

SEQ ID NO.7 was implemented in multibranch probes (i.e. probes comprising a plurality of probe elements) to take advantage of the amplification nature of the assay. These probes were designed as self-quenched or FRET quenched systems. These probes consist of the MMP substrate with hydrophilic spacers and N-terminal fluorophores that are released after enzymatic cleavage (self-quenched), and probes with additional Methyl Red (FRET quenched). With all these compounds, the effect caused by spacer location, different number and position of the fluorophores (3, 6 or 9) and the absence or presence of Methyl Red moieties (3 or 6) was evaluated.

Comparison of the background signal showed very different results for the different architectures. As can be seen from FIG. 7, only the schematically illustrated 3Dendrimer showed any significant background fluorescence in the absence of MMP, indicating that the fluorophores of the majority of the probe structures were successfully quenched. While a substantial decrease in background signal was observed from self-quenched probes when going from 3 to 6 or 9 units of FAM, the maximum quenching efficiency was achieved with FRET Dendrimer probe (SVC-01-186).

Figure 7:
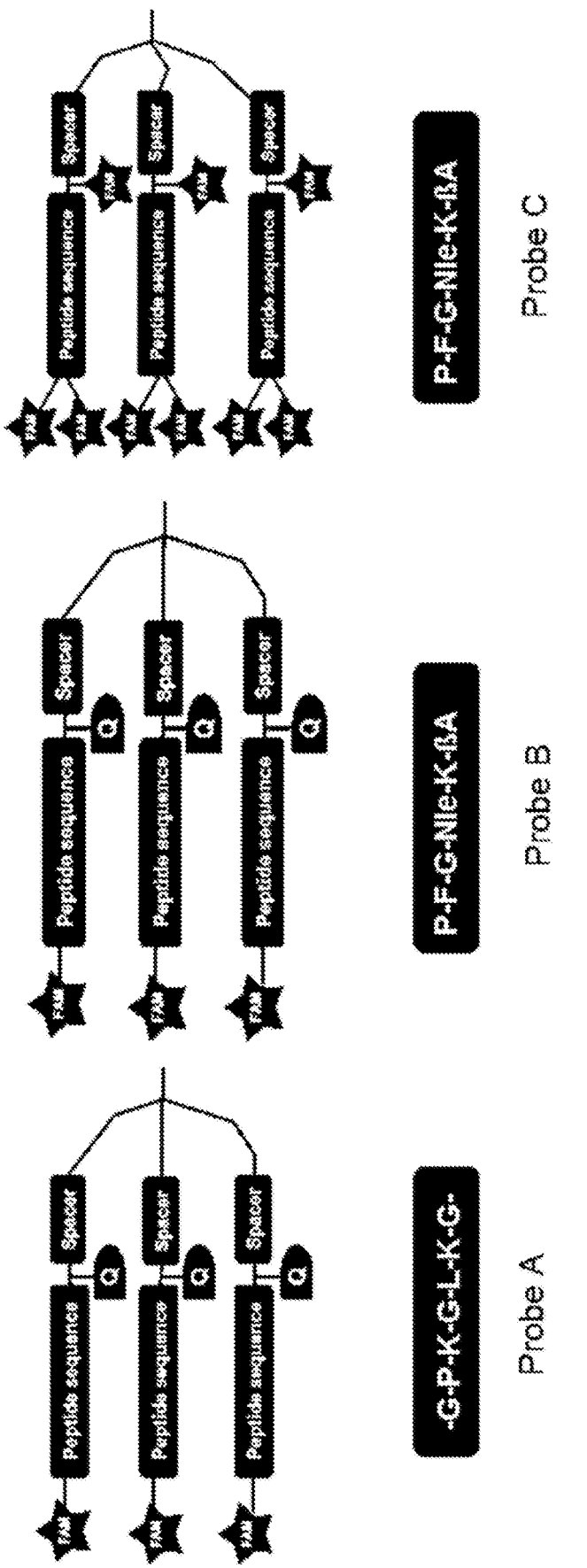
FIG. 7. Schematic illustrations of Probe A, Probe B and Probe C.

The different compounds were also evaluated according to the fold change in fluorescent signal in presence of MMP-9 and MMP-13, and the results are shown in Table 7. From this comparison, the FRET dendrimers comprising SEQ ID NO.1 and SEQ ID NO.7 (AMF-106 and SVC-186) together with the 9Dendrimer comprising SEQ ID NO.7 (SVC-196) were chosen for further evaluation. These dendrimers are shown in FIG. 7, probe A (AMF-106), probe B (SVC-186) and probe C (SVC-196).

TABLE 7

| Probe code | Probe sequence | Probe scaffold | MMP-9 (83 kDa) | MMP-13 (52 kDa) |
|---|---|---|---|---|
| AMF-111 | (-G-P-K-G-L-K-G-) | FRET monomer | 3.66 | 10.57 |
| TWB140 |  | 3Dendrimer | 1.06 | 1.47 |
| AMF-106 |  | FRET dendrimer | 11.20 | 34.52 |
| AMF-92 | (-P-F-G-Nle-K-βA-) | FRET monomer | 4.75 | 19.30 |
| SVC-188 |  | 3Dendrimer | 1.41 | 1.80 |
| SVC-186 |  | FRET dendrimer | 6.49 | 26.65 |
| SVC-189 |  | 6Dendrimer | 2.92 | 7.11 |
| SVC-196 |  | 9Dendrimer | 3.33 | 11.80 |
| SVC-195 |  | FRET 9Dendrimer | 4.84 | 9.00 |

We have assessed and validated the efficacy of FRET or self-quenched probes by including up to three fluorophores or two quenchers for each probe element and have also assessed this with a β-amino acid variant designed to enhance stability and specificity.

We have assessed a series of alternative quenchers, MethylRed, BHQ-1/3, or QSY-21, with the aim of producing a higher signal-to-noise ratio, which may enable lower levels of MMP detection at lower effective probe concentrations.

Improve the Specificity and Resistance to Proteolytic and Plasmin Degradation.

We have assessed a number of compounds including variants incorporating D-amino acids and β-amino acids at selected positions identified by MALDI analysis of the parent SVC-01-024 and TWB-140 compound as sites susceptible to plasmin degradation. Also, to reduce degradation without altering the amino acid constituents we have synthesised variants including PEG units at the amino and/or carboxy termini in order to block degradation from the ends of the peptide sequence.

Figure 9:
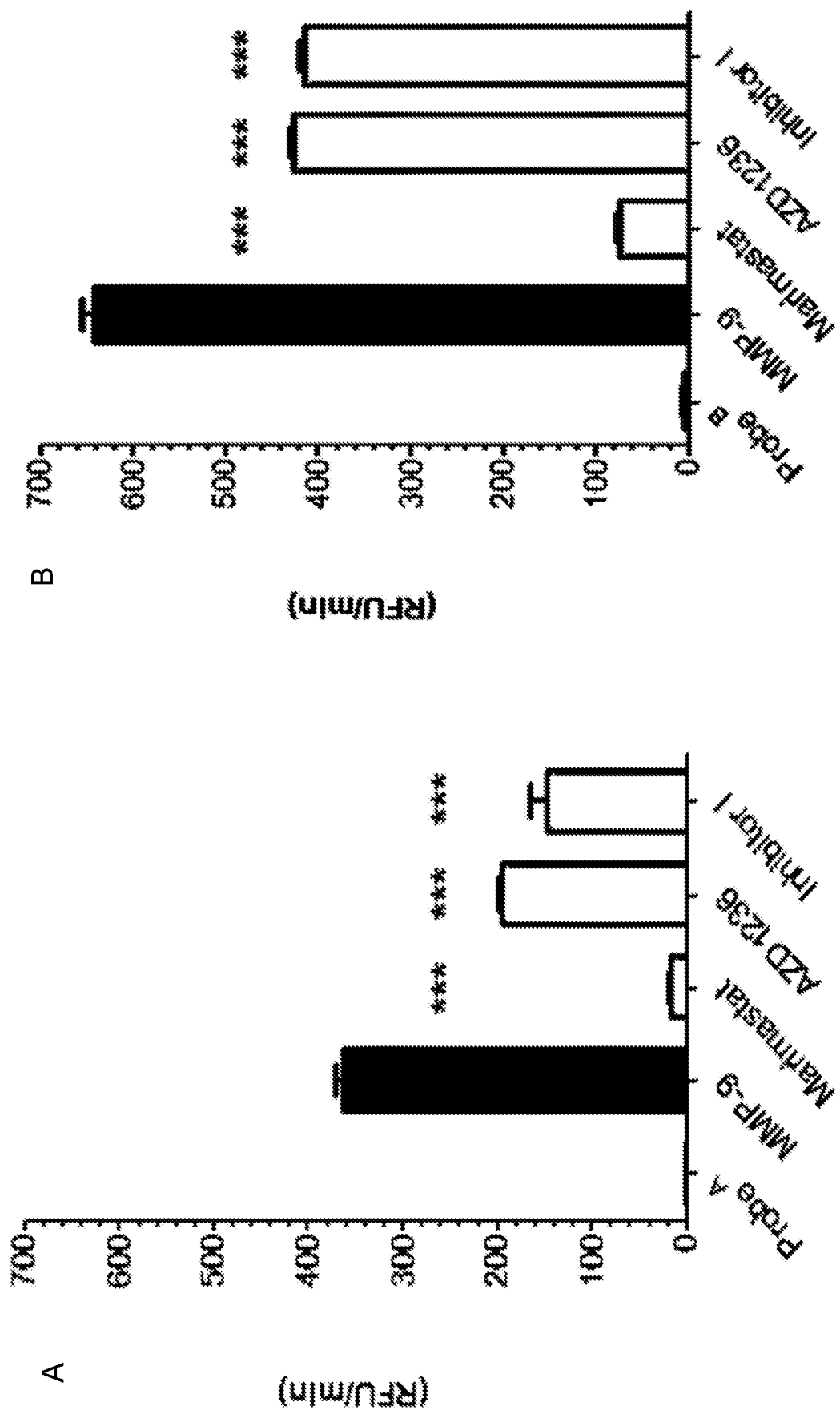
FIG. 9. Probe specificity by target inhibition for probes A and probe B. Data represents the fluorescence signal provided by the probe (1 µM) after 30 min using a multiwell plate fluorimeter at excitation/emission 485/528 nm. To validate the specificity and ability of molecular probe to detect the target enzyme, probe fluorescence (initiated by cleavage) was measured in the presence of enzyme with/without inhibitor. Inhibitors Marimastat (pan-MMP inhibitor), AZD1236 (MMP-2/9 inhibitor), Inhibitor I (MMP-9 inhibitor) were used at 200 nM.

Several inhibitors with IC$_{50}$s in the range 3-5 nM were tested in combination with the probes A and B. The fluorescent intensity was significantly reduced after incubation with Marimastat. The knock-down when the enzyme is previously incubated with known MMP inhibitors demonstrates that selective proteolytic activity by MMP is responsible for probe activation (FIG. 9).

Figure 10:
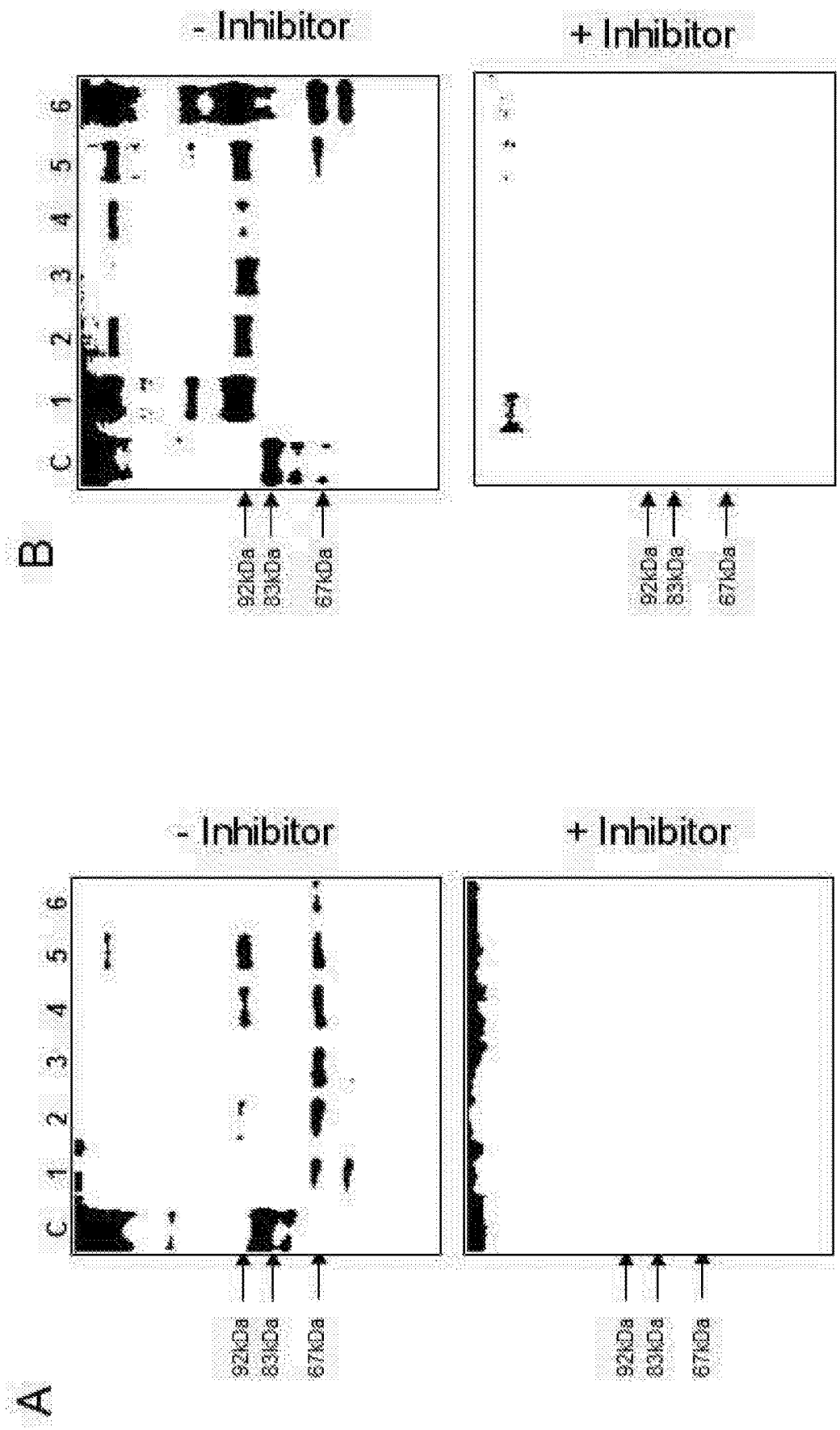
FIG. 10. Ex-vivo analysis of molecular probe detection of MMP-9 activity. Sheep zymography (A), Human zymography (B), in the presence or absence of an MMP-9 inhibitor.

An appropriate model to evaluate the utility of our probes was established by measuring the expression of MMP-9 in the samples of sheep and human lung tissue homogenates using gelatin zymography (FIG. 10). This model is discussed in more detail in the "Molecular probe response in an ex-vivo assay" section below.

Figure 11:
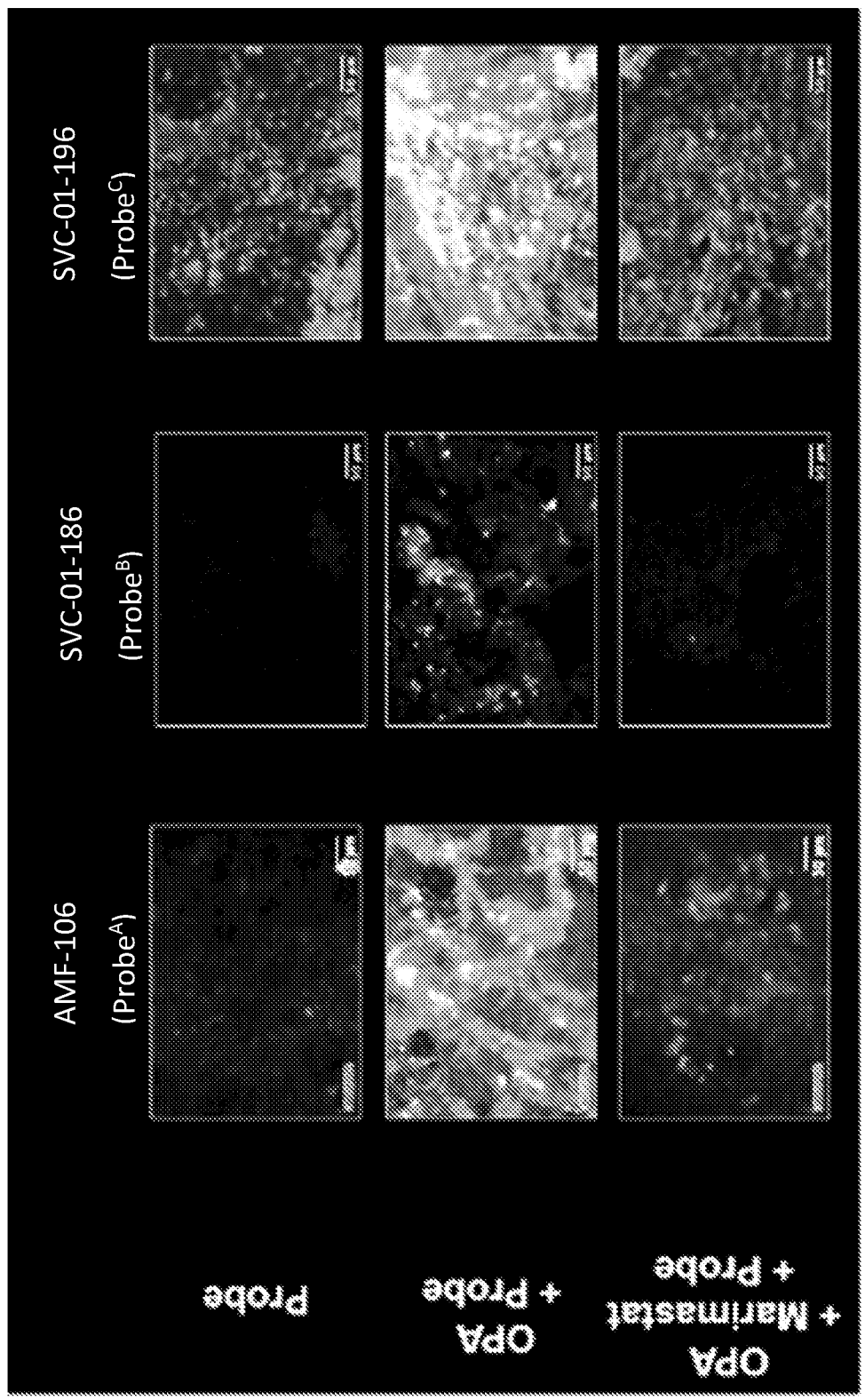
FIG. 11. Ex-vivo analysis of MMP-9 activity using molecular probes in sheep lung. Fluorescence data shown as increase from "normal segment" (%). Sheep fibrotic lung tissue biopsies were obtained from Ovine Pulmonary Adenocarcinoma—(OPA).
Figure 12:
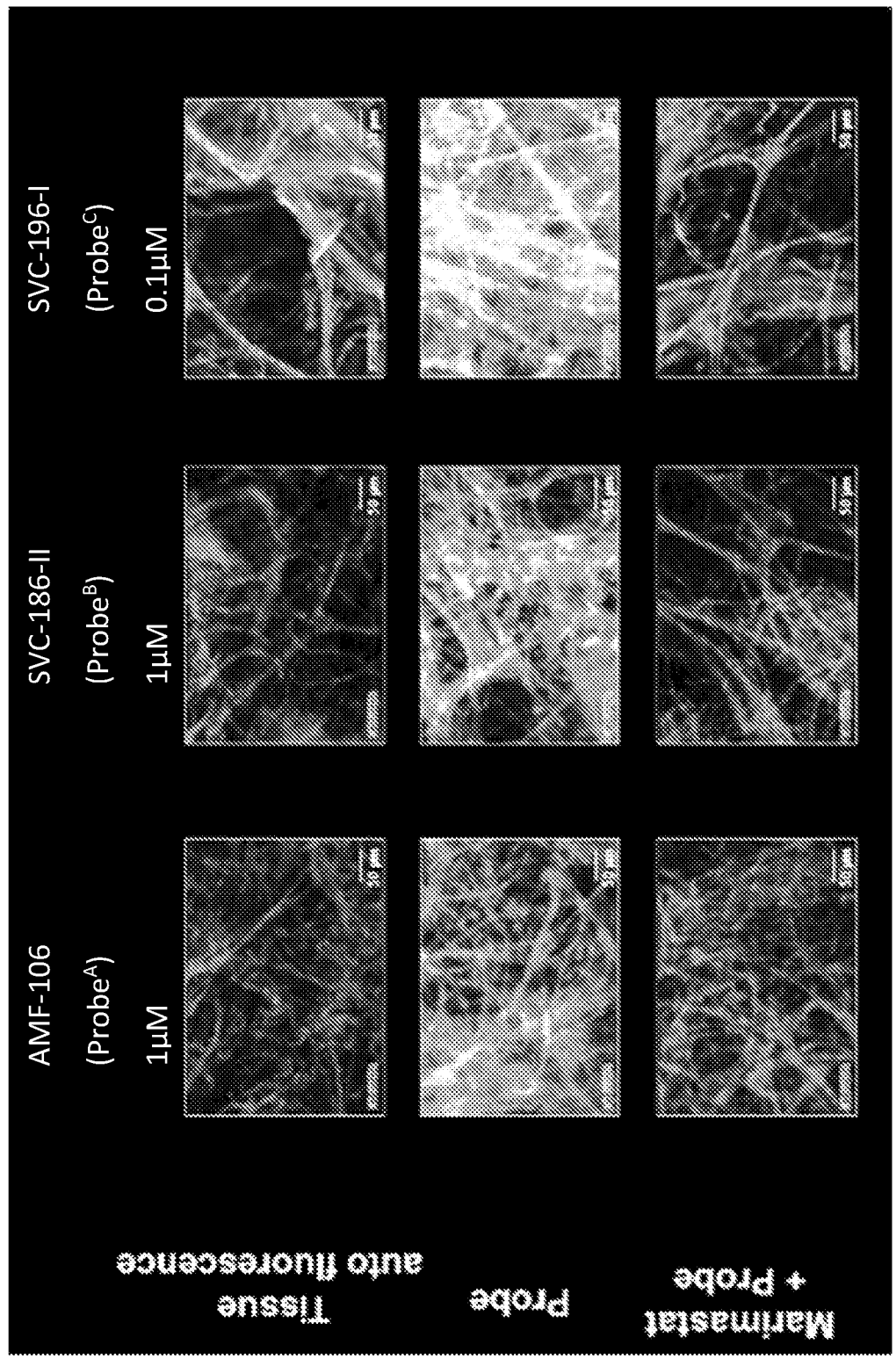
FIG. 12. Ex-vivo analysis of MMP-9 activity using molecular probes in human lung. Fluorescence data shown as increase from "normal segment" (%).

All compounds have undergone biological assessment. For stability we have assessed each compound in the presence of 0.9% NaCl (Saline) or pooled lavage fluid from patients with acute lung injury and analysed by matrix-assisted laser desorption/ionization (MALDI) or fourier transform mass spectrometry (FTMS). In vitro activation was assessed on benchtop confocal in the presence of compound with lung tissue samples. For the ex vivo and in vivo ovine lung (FIG. 11) and human lung tissue experiments (FIG. 12) each compound was assessed in a control lung segment (instilled with 2 ml PBS) or a fibrotic/cancer segment, the compound was administered to the segment of interest and this was imaged by probe based fCFM.

Assessment of the different MMP probe variants has illustrated the different mechanistic factors affecting the function of the probe in the lung environment, and specifically clarified the reasons why, out of all the MMP probe variants, only SVC-01-186 (probe B) is able to activate in the presence of MMP-2/9/13 in the lung and is stable in plasmin environment.

The alternative scaffolds were inferior to the design of SVC-01-186, SVC-01-196, and AMF-106 for this application. A probe variant (SVC-01-198) with 2 fluorophores near the C-terminus exhibited a much lower intensity upon activation by MMP and the presence of an additional quencher (SVC-01-187) did not further improved signal-to-noise ratio.

In Vitro Biological Studies: Specificity of Lead Molecular Probes

Figure 8:
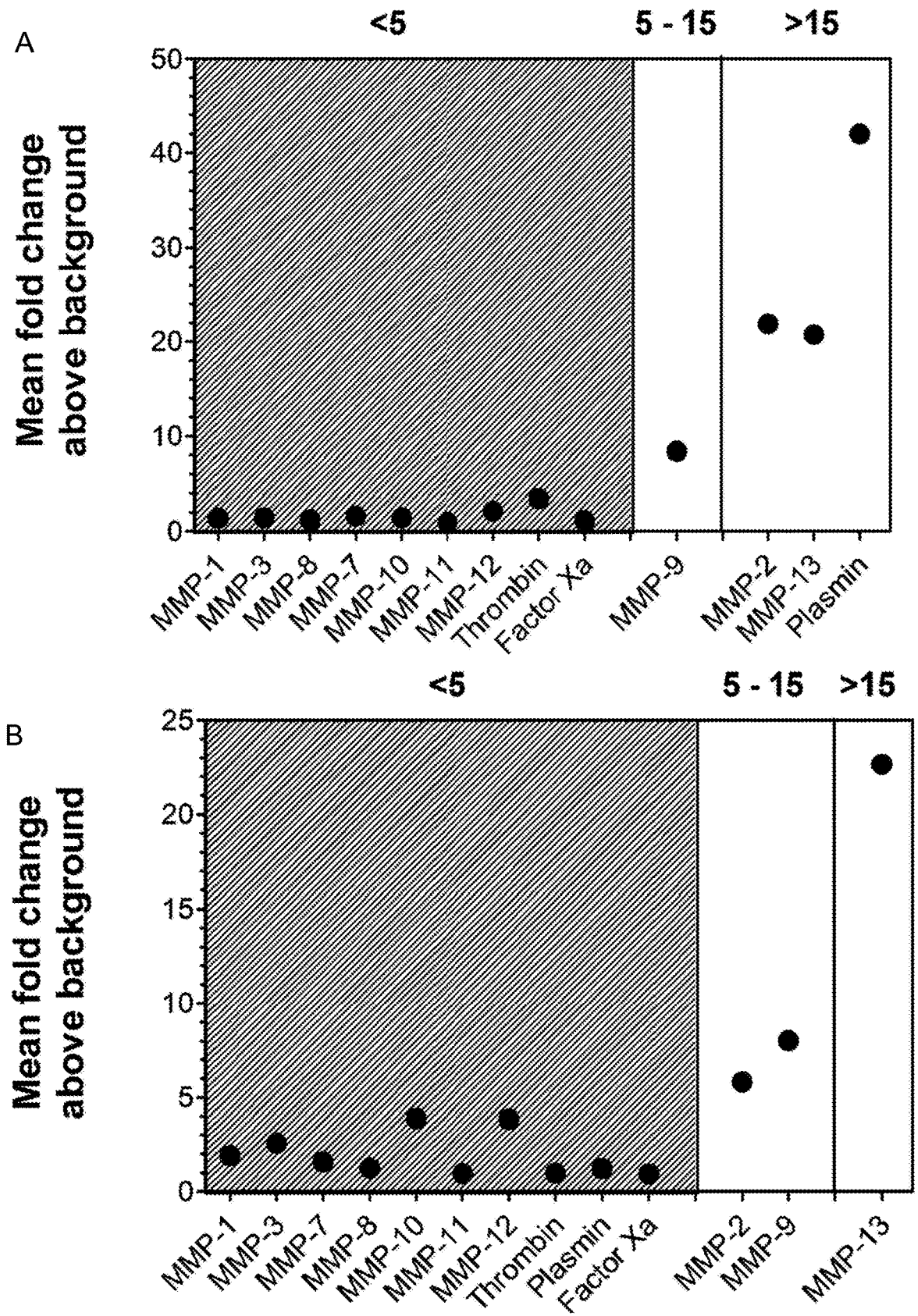
FIG. 8. Enzyme specificity of the FRET branched probes A, B and C. Data represents the average fold change in fluorescence over background signal provided by probe (10 µM) with exogenous enzymes using a multiwell plate fluorimeter (Synergy H1 Hybrid Reader, BioTek instruments Ltd) at excitation/emission 485/528 nm. Recombinant human catalytic domain MMPs-1, -2, -3, -7, -8, -9, -10, -11, -12, -13 were used at 30 nM. Recombinant human Thrombin, Plasmin and Factor Xa were used at 5 U/ml, 30 nM, 0.5 µM, respectively.
Figure 8:
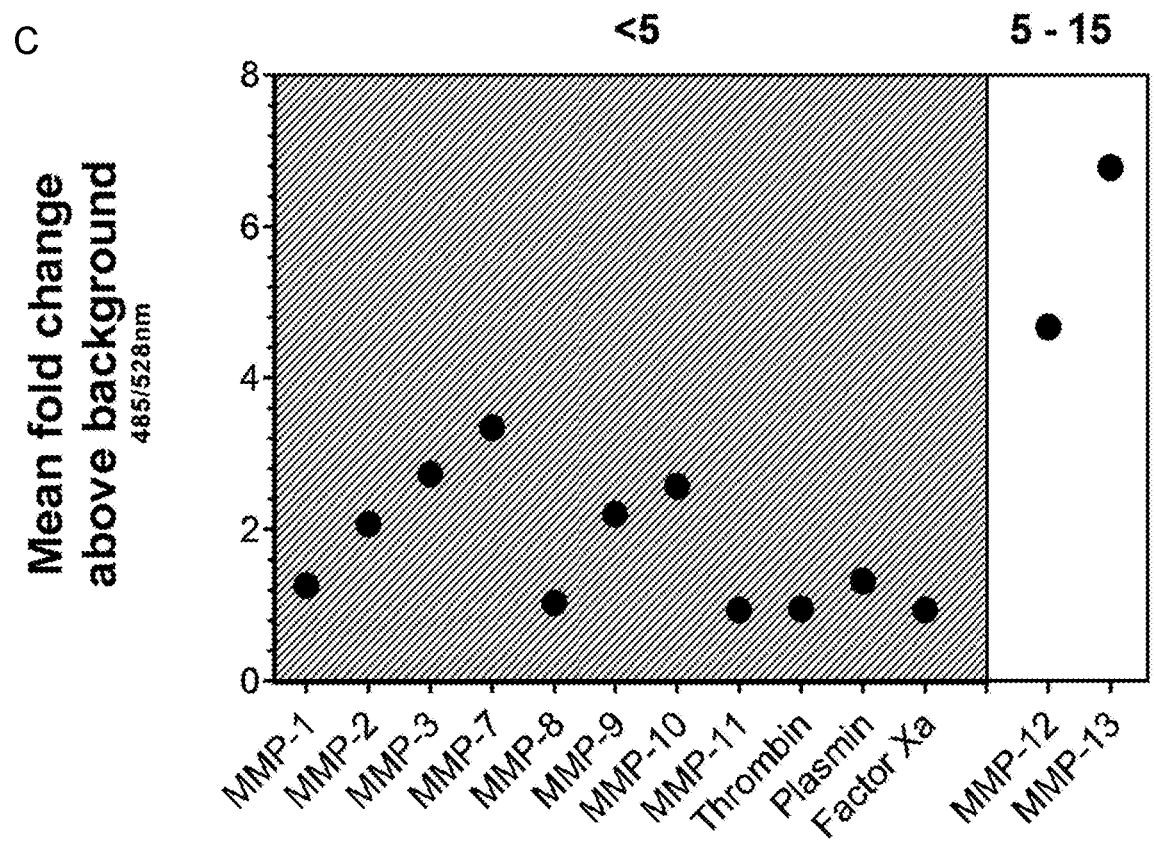

Three selected probes (A: AMF-106, B: SVC-186 B, and C: SVC-196) were evaluated in vitro in a new experiment including other members of the MMP family (MMPs-1, -2, -3, -7, -8, -9, -10, -11, -12, -13) as well as Thrombin, Plasmin and Factor Xa, and the results are shown in FIG. 8. Probe A (AMF-106) and B (SVC-01-186) showed better selectivity for MMP-2/9 compared with probe C that provided also lower signal-to-noise (fold change above the background) and poor selectivity. While probe A is susceptible to plasmin, probe B is plasmin resistant. The plasmin cleavage site was identified and attempts to make a resistant version replacing with D-aa in these positions were unsuccessful.

Enzyme kinetics of the molecular probe specificity to human MMP-2, MMP-9, MMP-13 and plasmin. The kinetic constants $K_M$ and $V_{max}$ were calculated for probe A and B (Table 8 below).

TABLE 8

| | Probe $^A$ | | | Probe $^B$ | | |
|---|---|---|---|---|---|---|
| | $V_{max}$ | $K_m$ | $V_{t=0}$ [10 µM] | $V_{max}$ | $K_m$ | $V_{t=0}$ [10 µM] |
| MMP-2 | 5.66 | 0.06 | 5.62 | 45.01 | 0.41 | 39.10 |
| MMP-9 | 27.10 | 0.53 | 27.75 | 43.97 | 0.59 | 39.61 |
| MMP-13 | 11.65 | 0.22 | 11.40 | 20.56 | 0.44 | 17.97 |
| Plasmin | 14.43 | 0.36 | 13.93 | 1.46 | 0.19 | 1.05 |

Validation of the Probe:

Several inhibitors with $IC_{50}$s in the range 3-5 nM were tested in combination with the probes A and B and the results shown in FIG. 9. AZD1236 and also hydroxamate-based MMP inhibitors such as MMP-9-inhibitor I or Marimastat were used. Marimastat is a potent broad-spectrum inhibitor of all the major MMPs and one of the most advanced MMP inhibitors in terms of preclinical and clinical development, with $IC_{50}$ values of 3 and 6 nM for MMP-9 and MMP-2 [*Pharmacol. Ther.* Vol. 75, No. 1, pp. 69-75, 1997]. This group of inhibitors contain a hydroxamate group that binds the zinc atom in the active site of the MMP enzyme.

The fluorescent intensity was significantly reduced after incubation with Marimastat. The knock-down when the enzyme is previously incubated with known MMP inhibitors demonstrates that selective proteolytic activity by MMP is responsible for probe activation.

Molecular Probe Response in an Ex-Vivo Assay

The expression of MMP-9 was analysed in several samples of sheep and human lung tissue homogenates using gelatin zymography (FIG. 10) in the presence or absence of inhibitor. After confirming the presence of variable amounts of MMP-9 in the different samples as previously predicted this homogenised lung tissue was considered an appropriate model to evaluate the utility of our probes.

Furthermore, the haemolytic activity in human blood and preliminary toxicity in animals was assessed for molecular probes, which confirmed the safety and non-toxicity of the compounds (FIG. 13).

Materials and Methods

General

Commercially available reagents were used without further purification. NMR spectra were recorded using Bruker AC spectrometers operating at 500 MHz for 1 hour. Chemical shifts are reported on the δ scale in ppm and are referenced to residual non-deuterated solvent resonances. Normal phase purifications by column chromatography were carried out on silica gel 60 (230-400 mesh). Analytical reverse-phase high-performance liquid chromatography (RP-HPLC) was performed on an HP1100 system equipped with a Discovery C18 reverse-phase column (5 cm×4.6 mm, 5 µm) with a flow rate of 1 mL/min and eluting with $H_2O/CH_3CN/HCOOH$ (95/5/0.1) to $H_2O/CH_3CN/HCOOH$ (5/95/0.1), over 6 min, holding at 95% ACN for 2 min, with detection at 254, 495 nm and by evaporative light scattering. Semi-preparative RP-HPLC was performed on an HP1100 system equipped with a Zorbax Eclipse XDB-C18 reverse-phase column (250×9.4 mm, 5 µm) with a flow rate 2.0 mL/min and eluting with 0.1% HCOOH in $H_2O$ (A) and 0.1% HCOOH in $CH_3CN$ (B), with a gradient of 5 to 95% B over 30 min and additional isocratic period of 5 min. Electrospray ionization mass spectrometry (ESI-MS) analyses were carried out on an Agilent Technologies LC/MSD Series 1100 quadrupole mass spectrometer (QMS) in an ESI mode. MALDI spectra were acquired on a Bruker Ultraflextreme MALDI TOF/TOF with a matrix solution of sinapic acid (10 mg/mL) in $H_2O/CH_3CN/TFA$ (50/50/0.1).

Methods of Synthesis of Probes

Synthesis of Linear MMP Probes ("FAM-PEG$_2$-G-P-K-G-L-K-G-K(MethylRed)-NH$_2$" and "FAM-PEG$_2$-P-F-G-Nle-K-βA-K(MR)-NH$_2$")

Figure 17:
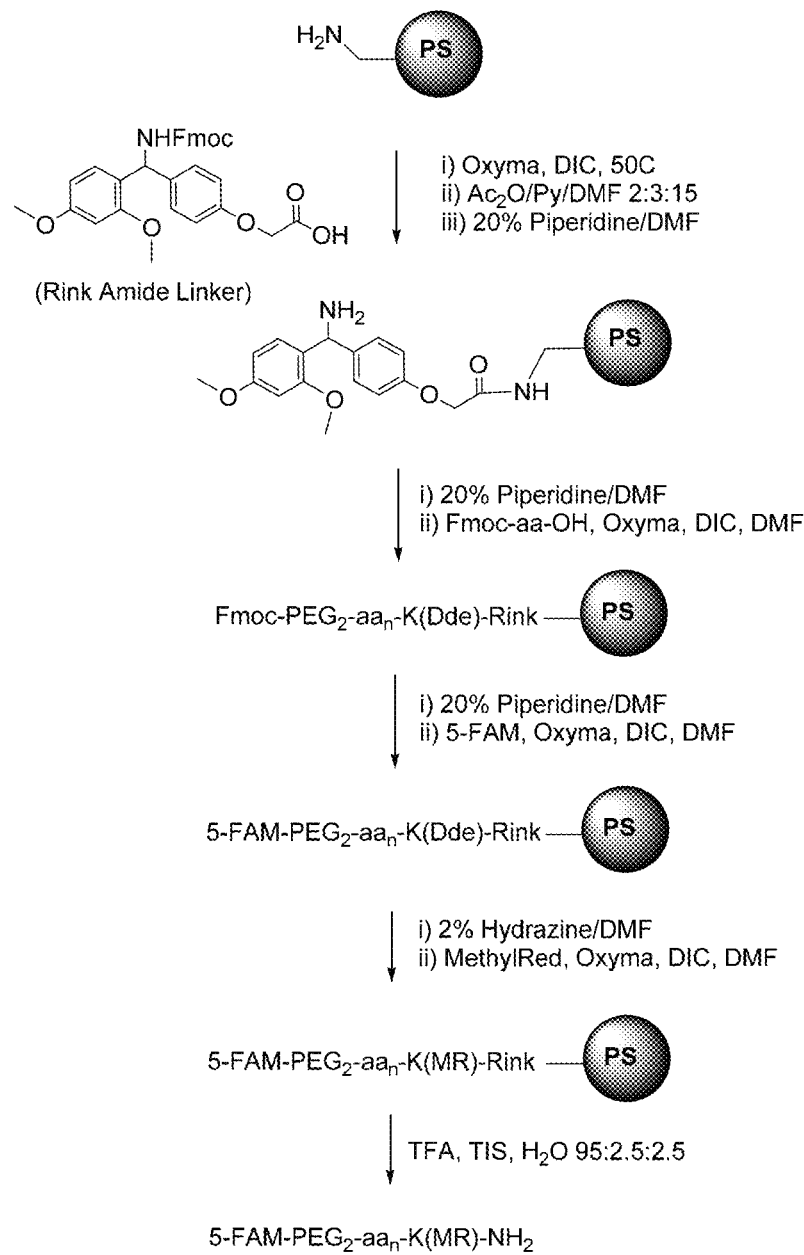
FIG. 17. Illustration of the synthesis of 1$^{st}$ generation Compound 1 and 2.

The synthesis of 1$^{st}$ generation Compound 1 and 2 is shown in FIG. 17.

Compound 1 [FAM-PEG$_2$-G-P-K-G-L-K-G-K(MethylRed)-NH$_2$ (SVC-01-24)] fragment was synthesised on solid-phase employing Fmoc-strategy, with standard amino acid coupling cycles with DIC and oxyma in peptide grade DMF at ~0.1 M reagent concentration. Fmoc deprotection steps were done in 20% piperidine in DMF (2×5 min). Between each step, the resin was washed with DMF, DCM and MeOH.

The resin was synthesized using a 4-[(2,4-dimethoxyphenyl)-(Fmoc-amino)methyl]phenoxyacetic acid (Rink amide linker) attached to aminomethyl PS resin (1.6 mmol/g, 1% DVB, 100-200 mesh). Thus, Fmoc-Rink-amide linker (2.6 g, 4.8 mmol) was dissolved in DMF (16 ml) and HOBt (0.7 g, 4.8 mmol) was added and the mixture was stirred for 10 min. DIC (0.7 ml, 4.8 mmol) was then added and the resulting mixture was stirred for further 5 min. The solution was added to aminomethyl polystyrene resin (1 g, 1.6 mmol/g) and shaken for 2 h. The resulting resin was washed with DMF (3×10 ml), DCM (3×10 ml) and MeOH (3×10 ml). After washing and Fmoc deprotection, the Fmoc-PEG$_2$-G-P-K-G-L-K-G-K(Dde) sequence was synthesised as described above using, Fmoc-Lys(Dde)-OH, Fmoc-Gly-OH, Fmoc-Lys(Boc)-OH, Fmoc-Leu-OH, Fmoc-Pro-OH and Fmoc-PEG$_2$-OH.

FAM and MethylRed Dye Coupling:

After Fmoc deprotection, 5-carboxyfluorescein (FAM) was coupled to the N-terminus as described above. After the sequence was completed, Dde protecting group was removed with 2% hydrazine in DMF (5×10 min) followed by the coupling of Methyl Red to the Lys side chain as described above. The coupling reactions were monitored by a ninhydrin test (E. Kaiser, R. L. Colescott, C. D. Bossinger and P. I. Cook, *Analytical Biochemistry*, 1970, 34, 595-598).

Sulfo-Cy5 Dye Coupling:

A solution containing sulfo-Cy5 (1 eq.) in anh (anhydrous) DMF (10 mg/ml) was activated with N,N,N',N'-Bis(tetramethylene)-O—(N-succinimidyl)uronium hexafluorophosphate (HSPyU) (1 eq.) and DIPEA (3 eq.) at 40° C. for 1 h. Once the activation is complete the solution is added to the resin together with DIPEA (3 eq) and shaken at room temperature (rt) overnight. The solution was drained and the resin washed with DMF until colourless wash solution, DCM (3×5 ml) and MeOH (3×5 ml).

Qsy21 Coupling:

N-terminal capping with QSY21-NHS ester (1 eq.) was done in anhDMF (0.1M) containing DIPEA (3 eq.) at rt for 12 h. The solution was drained and the resin washed with DMF until colourless wash solution, DCM (3×5 ml), MeOH (3×5 ml) and finally ether (3×5 ml).

Before cleavage, the resin was washed with 20% piperidine to remove any fluorescein phenol esters. After washing, the fragment was cleaved off the resin with TFA-TIS-H$_2$O (95:2.5:2.5) (90 min) and precipitated with cold ether to give SVC-01-24 (MALDI-ToF m/z: 1538.1988, >95% HPLC purity, $t_R$=6.357 min).

By following the above procedure, Compound 2 [FAM-PEG$_2$-P-F-G-Nle-K-βA-K(MR)-NH$_2$ (AMF-025)] was synthesised using Fmoc-Lys(Dde)-OH, Fmoc-β-Ala-OH, Fmoc-Lys(Boc)-OH, Fmoc-Nle-OH, Fmoc-Gly-OH, Fmoc-Phe-OH, Fmoc-Pro-OH, and Fmoc-PEG$_2$-OH followed by coupling of FAM and MethylRed. After washing, the fragment was cleaved off the resin with TFA-TIS-H$_2$O (95:2.5:2.5) (90 min) and precipitated with cold ether to give Compound 2 (MALDI-ToF m/z: 1514.6800; >95% HPLC purity, $t_R$=6.330 min).

Synthesis of Multi-Fluorophore Linear Probe Scaffold:

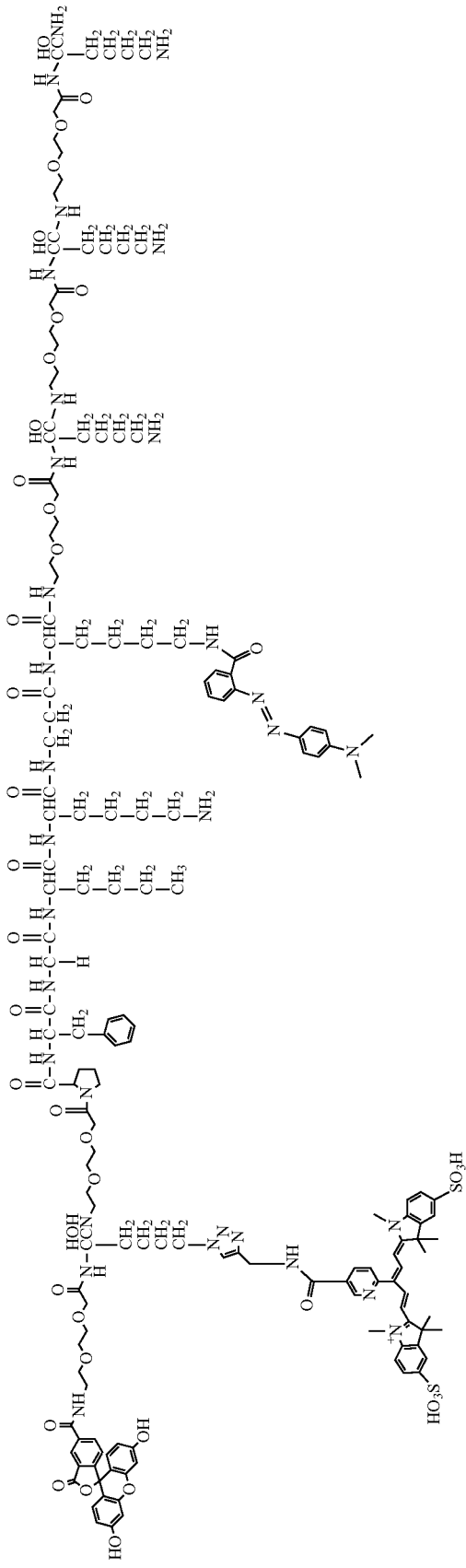

Figure 18:
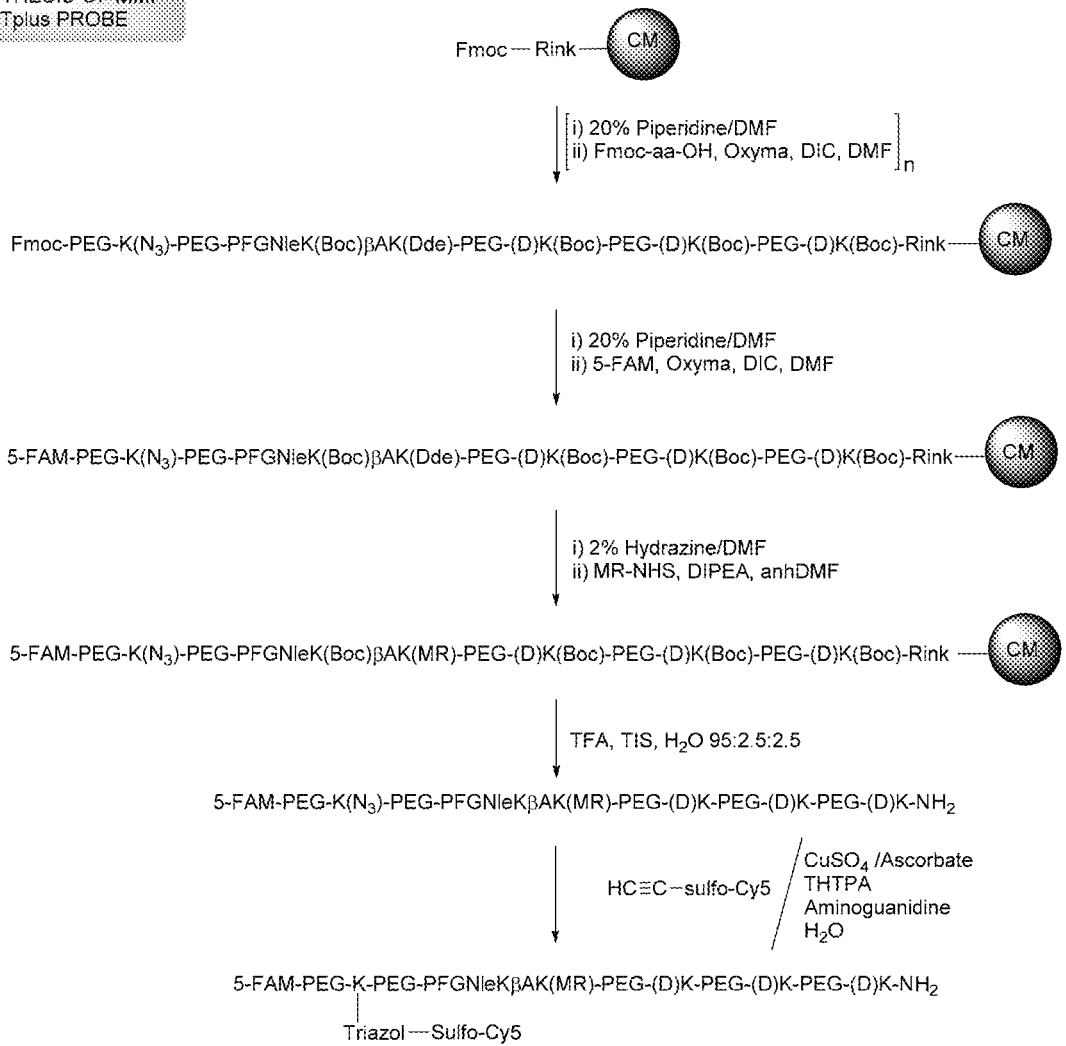
FIG. 18. Illustration of the synthesis of 2nd generation Compound 3 (AMF-210).

The synthesis of 2nd generation Compound 3 (AMF-210) is shown in FIG. 18.

Manual peptide synthesis was performed on Aminomethyl-ChemMatrix resin using Rink amide linker.

Coupling of Rink Amide Linker:

Fmoc-Rink linker (4-[(R,S)-a-[1-(9H-Fluoren-9-yl)-methoxy-formamido]-2,4-dimethoxybenzyl-phenoxyacetic acid) (0.54 g, 1.0 eq) was dissolved in DMF (10 mL) and Oxyma (0.14 g, 1.0 eq.) was added and the mixture was stirred for 10 min. Diisopropylcarbodiimide (DIC, 155 µL, 1.0 eq.) was then added and the solution stirred for 1 min before adding it to Aminomethyl-ChemMatrix resin (1.0 g, 1.0 mmol/g). The resulting mixture was stirred at 50° C. for 45 min and washed with DMF (3×10 mL), DCM (3×10 mL) and MeOH (3×10 mL). Finally the resin was treated with $Ac_2O$:Py:DMF (2:3:15) for 30 min at rt in order to cap any remaining free amino group and it was washed again with DMF (3×10 mL), DCM (3×10 mL) and MeOH (3×10 mL). Resin loading was calculated after that as ~0.58 mmol/g.

Fmoc Deprotection:

In general, to the resin pre-swollen in DCM was added 20% piperidine in DMF and stirred at rt (2×10 min). The solution was drained and the resin washed with DMF (3×10 mL), DCM (3×10 mL) and MeOH (3×10 mL). In the cases were Fmoc deprotection was done in Cy5 containing peptides, a solution of 2% DBU in DMF (2×10 min, rt) was used instead.

Aminoacid Coupling:

A solution of the appropriate D- or L-amino acid (3.0 eq per amine) and Oxyma (3.0 eq) in DMF (0.1M) was stirred for 10 min. DIC (3.0 eq) was added and stirred for 1 min. The pre-activated mixture was then added to the resin pre-swollen in DCM and the reaction heated at 50° C. for 30 min. The solution was drained and washed with DMF (3×10 mL), DCM (3×10 mL) and MeOH (3×10 mL). The completion of the coupling and deprotection reactions was monitored by Kaiser test or Chloranil test when secondary amines are involved. The side chain protecting group used was Boc for arginine, tryptophan and lysine. Fmoc-Lys(Dde)-OH was used as orthogonal reagent to introduce the dyes.

Coupling of Other Carboxylic Acids:

Coupling of {2-[2-(Fmoc-amino)ethoxy]ethoxy}acetic acid (PEG), 5-Carboxyfluorescein (FAM) and Fmoc-Lys ($N_3$)—OH was done following the same procedure described for Aminoacid coupling.

Dde Deprotection:

To the resin pre-swollen in DCM was added 2% hydrazine in DMF and stirred at rt (5×10 min). The solution was drained and the resin washed with DMF (3×10 mL), DCM (3×10 mL) and MeOH (3×10 mL).

MethylRed-NHS Coupling:

MethylRed-NHS ester (1 eq) coupling in solid phase was done in anhDMF (0.1M) containing DIPEA (3 eq) at rt for 12 h. The solution was drained and the resin washed with DMF until colourless wash solution, DCM (3×5 mL), MeOH (3×5 mL) and finally ether (3×5 mL).

Cleavage and Purification:

The resin pre-swollen in DCM was treated with a cleavage cocktail of TFA:triisopropylsilane (TIS):water (95:2.5:2.5) for 3 h at room temperature. The reaction solution was drained and the resin washed again with cleavage cocktail. The combined solution was precipitated against cold ether, centrifuged (×3) and purified by RP-HPLC on a $C_{18}$ semi-preparative column. The desired fraction containing the product were collected and lyophilized to afford compound AMF-209 that was characterized by MALDI and analytical HPLC: $t_R$=4.174 min, MALDI calc. for $C_{127}H_{187}N_{28}O_{33}$ $[M+H]^+$: 2634.056; found: 2634.031.

Synthesis of Sulfo-Cy5-Alkyne:

Sulfo-Cy5-Carboxylic acid (75 mg, 0.11 mmol) was dissolved in anhDMF (8 mL). HSPyU (46 mg, 0.11 mmol) and DIPEA (58 µL, 0.33 mmol) were added and the mixture stirred at 40° C. for 1 h. Propargylamine (30 mg, 0.55 mmol) was added together with DIPEA (58 µL, 0.33 mmol) and the reaction was stirred overnight. The solvent was removed under vacuum. Purification by column chromatography (10:1 $ACN-H_2O$) afforded the compound sulfo-Cy5-alkyne as a dark blue solid (55 mg, 70%). $^1$H-NMR (500 MHz, DMSO-$d_6$) δ: 9.28 (t, J=5.5 Hz, NH), 9.23 (d, J=2.3 Hz, 1H), 8.47 (s, 1H), 8.44 (s, 1H), 8.38 (dd, J=8.1, 2.3 Hz, 1H), 7.84 (s, 2H), 7.64 (m, 3H), 7.32 (d, J=8.3 Hz, 2H), 5.84 (m, 2H), 4.15 (dd, J=5.5, 2.5 Hz, 2H), 3.34 (s, 6H), 3.20 (t, J=2.5 Hz, 1H), 1.78 (s, 12H); $^{13}$C-NMR (125 MHz, DMSO-$d_6$) δ: 174.2, 164.2, 157.3, 152.2, 149.0, 145.6, 142.4, 140.4, 135.9, 127.6, 125.8, 125.2, 119.7, 110.2, 100.7, 80.9, 73.0, 49.0, 31.0, 28.4, 26.7; MS (ES)$^+$ m/z 701 [M]$^+$; HPLC $t_R$ 3.921 min (GE10).

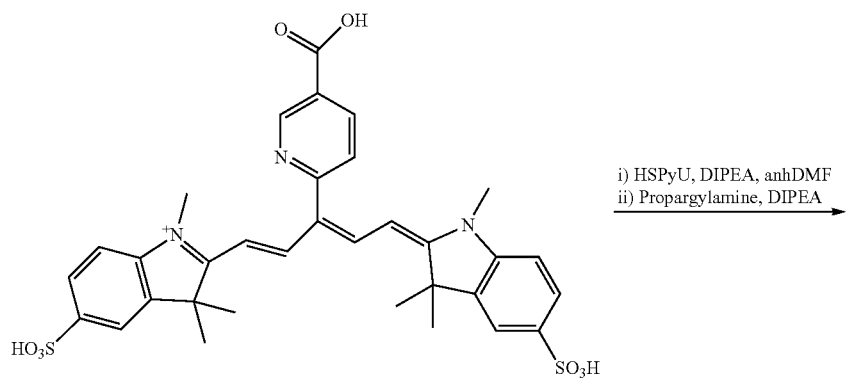

i) HSPyU, DIPEA, anhDMF
ii) Propargylamine, DIPEA

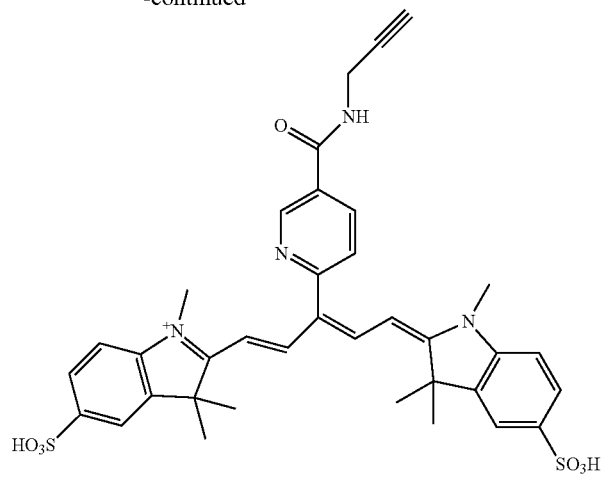

Labelling with Sulfo-Cy5-Alkyne:

Click reaction between sulfo-Cy5-alkyne (AMF-208) and azide-FRET peptide (AMF-209) was done in solution phase: in an eppendorf tube the following aqueous reagents were mixed: azide-peptide (AMF-209) (50 μL, 10 mM), sulfo-Cy5-alkyne (AMF-208) (50 μL, 30 mM), premixed $CuSO_4$ and THPTA (40 μL $CuSO_4$ 20 mM and 80 μL THPTA 50 mM), aminoguanidine hydrochloride (250 μL, 100 mM) and finally sodium ascorbate (250 μL, 100 mM). The click-chemistry reaction was allowed to proceed at 30° C. for 5 h, the reaction mixture was lyophilised and purified by HPLC to give the final FRETplus MMP-probe AMF-210, which was characterized by MALDI and analytical HPLC: AMF-210: HPLC $t_R$=3.921 min, MALDI calc. for $C_{163}H_{223}N_{32}O_{40}S_2[M]^+$: 3334.880; found: 3334.398.

Synthesis of Branched Dendrimer Scaffold:

The dendrimer scaffold was synthesised by following the prior art reported in WO 2012/136958 A2 (Aslam et al).

Synthesis of Monomer (V)

Multi-valent probe synthesis required the preparation of the monomer (V) which was synthesised in six steps (M. Ternon, J. J. Diaz-Mochon, A. Belsom, M. Bradley, *Tetrahedron*, 2004, 60, 8721) as shown in Scheme 1. Monomer (V) was prepared by the 1,4 addition of the hydroxy groups of 1,1,1-tris(hydroxymethyl)amino-methane onto acrylonitrile, followed by amino group protection (Boc). Reduction of the nitrile groups with $PtO_2/H_2$ gave (III) which was treated with DdeOH to give the tris-Dde protected amine (IV). Following removal of the Boc protecting group, the isocyanate (V) was prepared following the procedure of Knölker (H. J. Knölker, T. Braxmeier, G. Schlechtingen, *Angew. Chem. Int. Ed.*, 1995, 34, 2497).

Fmoc-Rink Amide ChemMatrix Resin (VI):

Peptide synthesis was performed on Aminomethyl-ChemMatrix resin using 4-[(2,4-Dimethoxyphenyl)-(Fmoc-amino)methyl]phenoxyacetic acid (Rink amide linker) by following the procedure. Thus, Fmoc-Rink-amide (0.54 g, 1.0 eq) was dissolved in DMF (10 mL) and Oxyma (0.14 g, 1.0 eq.) was added and the mixture was stirred for 10 min. Diisopropylcarbodiimide (DIC, 155 μL, 1.0 eq.) was then added and the solution stirred for 1 min before adding it to Aminomethyl-ChemMatrix resin (1.0 g, 1.0 mmol/g). The resulting mixture was stirred at 50° C. for 45 min and washed with DMF (3×10 mL), DCM (3×10 mL) and MeOH (3×10 mL). Finally the resin was treated with $Ac_2O$:Py:DMF (2:3:15) for 30 min at rt in order to cap any remaining free amino group and it was washed again with DMF (3×10 mL), DCM (3×10 mL) and MeOH (3×10 mL). Resin loading was calculated after that as ~0.58 mmol/g. The coupling reaction was monitored by ninhydrin test as discussed above.

The probes were synthesised on a ChemMatrix resin derivatized with an Fmoc-Rink Amide type linker (Scheme 1). The linker (VI) was loaded with monomer (V) to give the tri-branched scaffold (VII). The appropriate Fmoc-spacers (Pegylation), Fmoc-solubilizers (D-amino acids) and specific sequences were coupled sequentially followed by the attachment of FAM. Following the removal of the Dde groups (2% hydrazine in DMF) the MethylRed NHS ester (MR-NHS) was coupled and the resin was wash with 20% piperdine in DMF before the probe was cleaved from the resin using TFA/TIS/DCM (90/5/5).

Scheme 3 Synthesis of 3<sup>rd</sup> generation Compound 4-9.

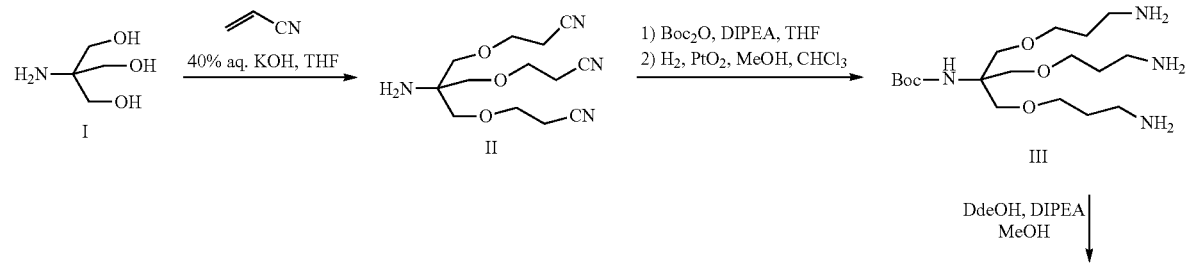

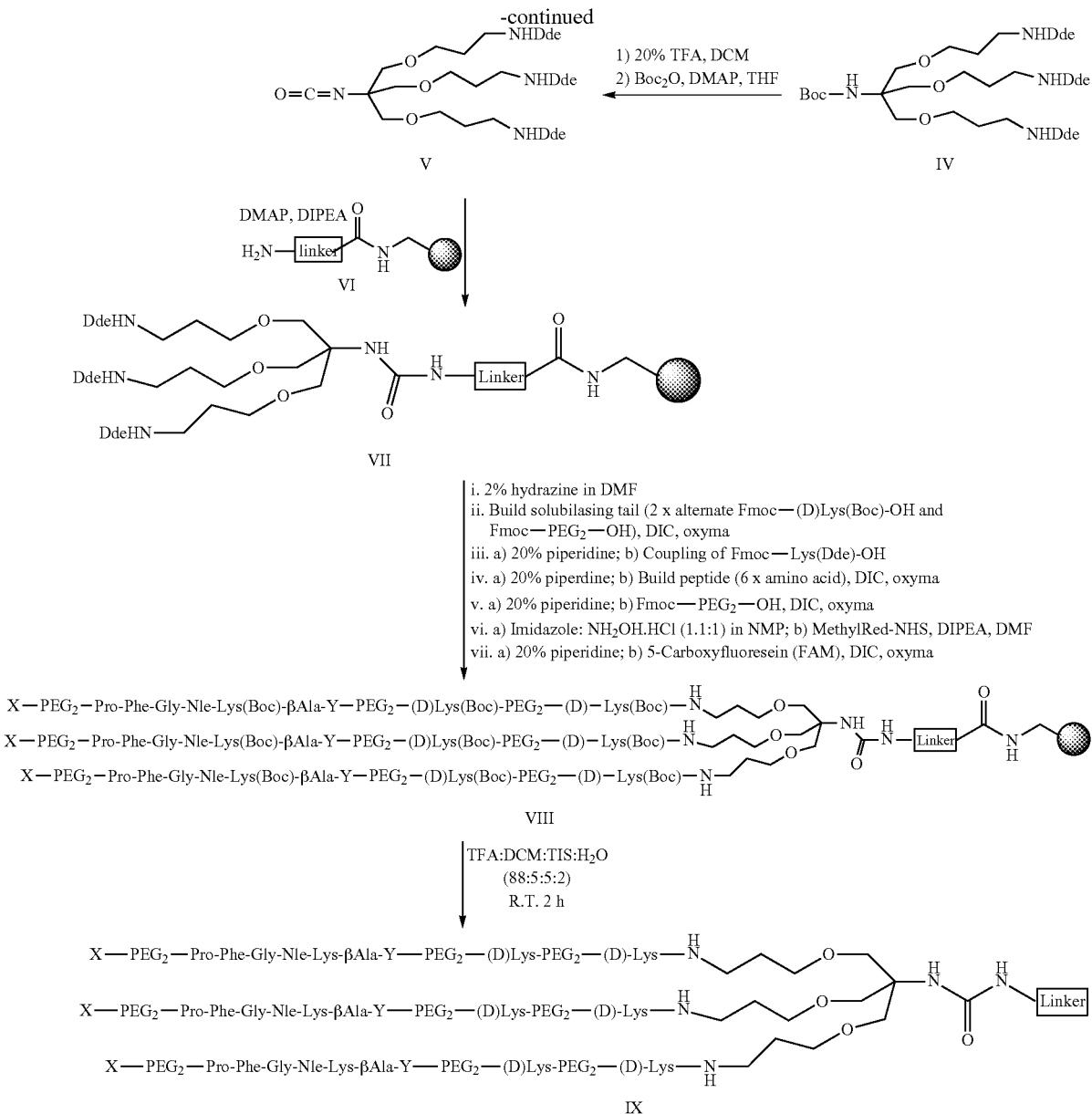

Compound 4: X = FAM; Y = 0; Linker = H
Compound 5: X = FAM; Y = K(MR); Linker = H
Compound 6: X = K(FAM)2; Y = K(FAM); Linker = H
Compound 7: X = FAM; Y = K(MR)2; Linker = H
Compound 8: X = FAM; Y = 0; Linker = K(MR)—PEG2—k—PEG2—K(Alkyne)—NH2
Compound 9: X = NBD; Y = K(MR); Linker = H Fmoc Rink-Amide linker Peptide synthesis was performed on Aminomethyl-ChemMatrix resin using Rink amide linker by following the procedure. Fmoc-Rink-amide (0.54 g, 1.0 eq) was dissolved in DMF (10 mL) and Oxyma (0.14 g, 1.0 eq.) was added and the mixture was stirred for 10 min. Diisopropylcarbodiimide (DIC, 155 µL, 1.0 eq.) was then added and the solution stirred for 1 min before adding it to Aminomethyl-ChemMatrix resin (1.0 g, 1.0 mmol/g). The resulting mixture was stirred at 50° C. for 45 min and washed with DMF (3×10 mL), DCM (3×10 mL) and MeOH (3×10 mL). Finally the resin was treated with Ac2O:Py:DMF (2:3:15) for 30 min at rt in order to cap any remaining free amino group and it was washed again with DMF (3×10 mL), DCM (3×10 mL) and MeOH (3×10 mL). Resin loading was calculated after that as ~0.58 mmol/g.

General Procedure for the Fmoc Deprotection

To the resin (pre-swollen in DCM) was added 20% piperidine in DMF (5 mL) and the reaction mixture was shaken for 10 min. The solution was drained and the resin was washed with DMF (3×10 mL), DCM (3×10 mL) and MeOH (3×10 mL). This procedure was repeated twice. The coupling reaction was monitored by the ninhydrin test as described above.

Isocyanate Coupling to Give (VII)

To resin (0.30 mmol), pre-swollen in DCM (10 mL), was added a solution of isocyanate (6) (920 g, 0.93 mmol), DIPEA (0.2 mL, 0.93 mmol) and DMAP (22 mg, 0.17 mmol) in a mixture of DCM/DMF (1:1, 5 mL) and the mixture was shaken overnight and the reaction monitored by ninhydrin test. The solution was drained and the resin was washed with DMF (3×20 mL), DCM (3×20 mL) and MeOH (3×20 mL) and ether (3×20 mL). (3×20 mL). The coupling reaction was monitored by the ninhydrin test as described above.

Pegylation ({2-[2-(Fmoc-amino)ethoxy]ethoxy}acetic acid or $PEG_2$-OH)

A solution of $PEG_2$-OH (3.0 eq per amine, 0.1M) and Oxyma (3.0 eq, 0.1M) in DMF was stirred for 10 min. DIC (3.0 eq, 0.1M) was added and stirred for 1 min. The pre-activated mixture was then added to the resin pre-swollen in DCM and the reaction heated at 50° C. for 30 min. The solution was drained and washed with DMF (3×10 mL), DCM (3×10 mL) and MeOH (3×10 mL).

Peptide Synthesis

Peptide Sequence: -P-F-G-Nle-K-βA-

A solution of the appropriate Fmoc-amino acid (3.0 mmol, 10 eq) [Fmoc-Lys(Dde)-OH, Fmoc-β-Ala-OH, Fmoc-Lys(Boc)-OH, Fmoc-Nle-OH, Fmoc-Gly-OH, Fmoc-Phe-OH, Fmoc-Pro-OH] and Oxyma (3.0 mmol, 10 eq) was added and the mixture was stirred for 5-10 min. DIC (3.0 mmol, 10 eq) was then added and the resulting mixture was stirred for a further 2 min. The solution was added to pre-swollen resin in DCM and the reaction mixture was mixed for 0.5 h at 60° C. The solution was drained and the resin washed DMF (3×20 mL), DCM (3×20 mL) and MeOH (3×20 mL). The coupling reactions were monitored by ninhydrin test as discussed above.

5-carboxyfluorescein (FAM) Labelling

A solution of FAM (3-10 eq) and oxyma (3-10 eq) in DMF (0.1 M) was stirred for 10-15 min followed by DIC (3-10 eq) and the resulting solution was stirred for further 1-2 min. This solution was added to the appropriate resin (1 eq), pre-swollen in DCM, and the reaction mixture was stirred at room temperature or 60° C. for 0.5-1 h. The solution was drained and the resin washed with DMF (×3), DCM (×3) and MeOH (×3). The coupling reactions were monitored by ninhydrin test. Before cleavage, the resin was washed with 20% piperidine to remove any fluorescein phenol esters.

Dde Deprotection

Selective Dde deprotection was done with a solution containing Imidazole (1.35 mmol) and Hydroxylamine hydrochloride (1.80 mmol) in NMP (5 mL). [Díaz-Mochón, J. J.; Bialy, L.; Bradley, M. *Org. Lett.* 2004, 6 (7), 1127-1129]. After complete dissolution 5 volumes of this solution were diluted with 1 volume of $CH_2Cl_2$ and the resin was treated with the final mixture for 3 h at room temperature. The solution was drained and the resin washed with DMF (3×10 mL), DCM (3×10 mL) and MeOH (3×10 mL).

MethylRed (MR) NHS Ester Labelling

A solution of MR-NHS ester (3-10 eq) and DIPEA (3-10 eq) in DMF (0.1 M) was added to the appropriate resin (1 eq), pre-swollen in DCM, and the reaction mixture was stirred at room temperature or 60° C. for 0.5-1 h. The solution was drained and the resin washed with DMF (×3), DCM (×3) and MeOH (×3). The coupling reactions were monitored by ninhydrin test as described above.

7-Nitrobenzofurazan (NBD) Coupling

To a solution of NBD-PEG-NHS (3.0 mmol, 10 eq) in DMF (3 mL) was added DIPEA (3.0 mmol, 10 eq). The resulting solution was added to resin (1 eq), pre-swollen in DCM, and the reaction mixture was shaken for 0.5 h. The solution was drained and the resin washed with DMF (×3), DCM (×3) and MeOH (×3). The coupling reaction was monitored by ninhydrin test as described above.

TFA Cleavage and Purification of Reporter Compound 4 (SVC-01-188)

The resin, pre-swollen in DCM, was treated with a cleavage cocktail of TFA TIS/DCM (90/5/5, 0.5 mL) for 1.5 h. The solution was drained and the resin was washed with the cleavage cocktail and added to ice-cold ether (7.5 mL). The precipitated solid (22 mg) was collected by centrifugation and the solvent removed by decantation and the precipitate was washed with cold ether (3×5 mL). The precipitate was then purified by preparative reverse phase HPLC and the desired fractions were pooled and lyophilized to afford products that were characterized by MALDI and analytical HPLC.

Compound 4
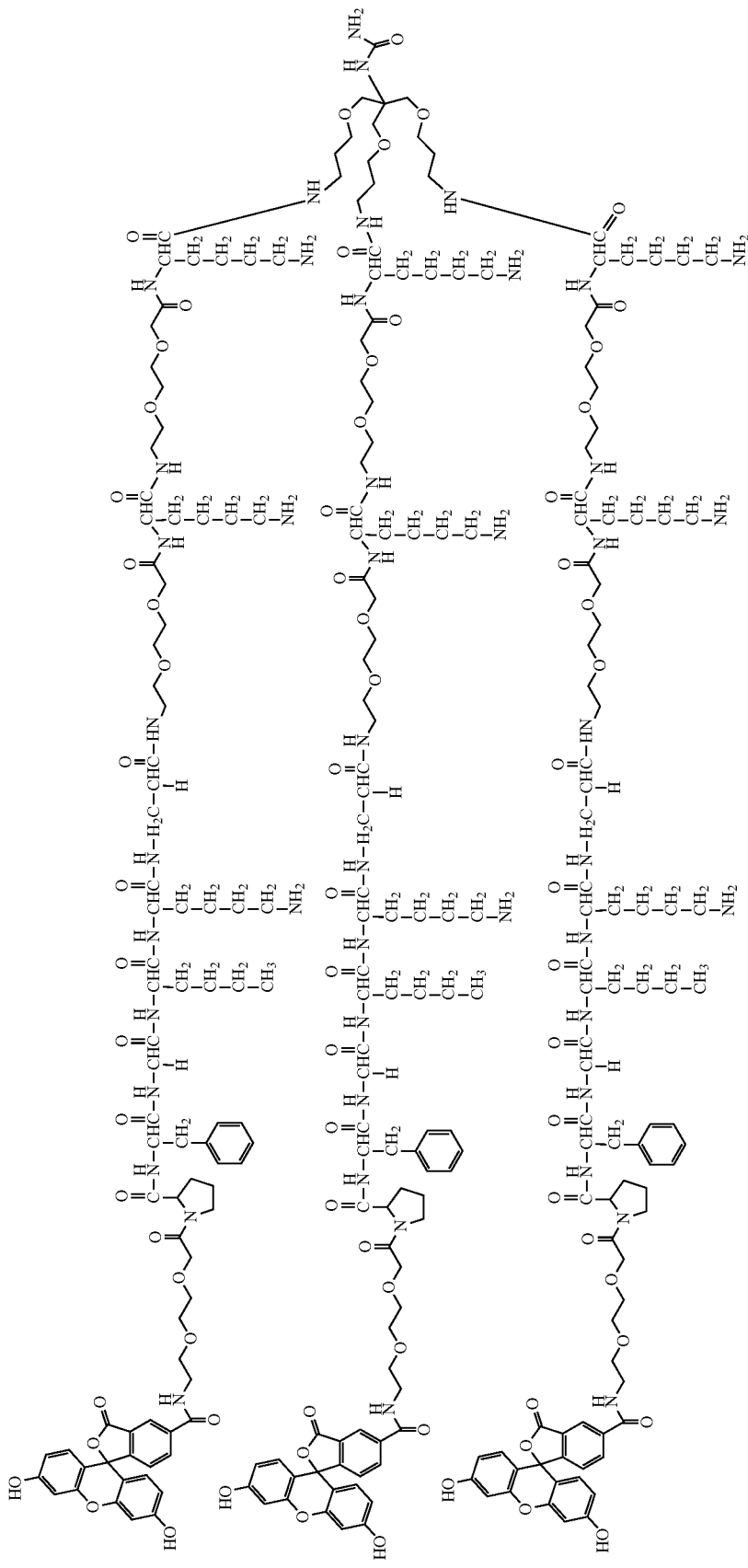
(SVC-01-188): HPLC $t_R$ = 3.366 min, MALDI calc. for $C_{260}H_{375}N_{47}O_{73}$ [M + 6H]$^+$: 888.8516; found: 888.8140 [M + 6H]$^+$.

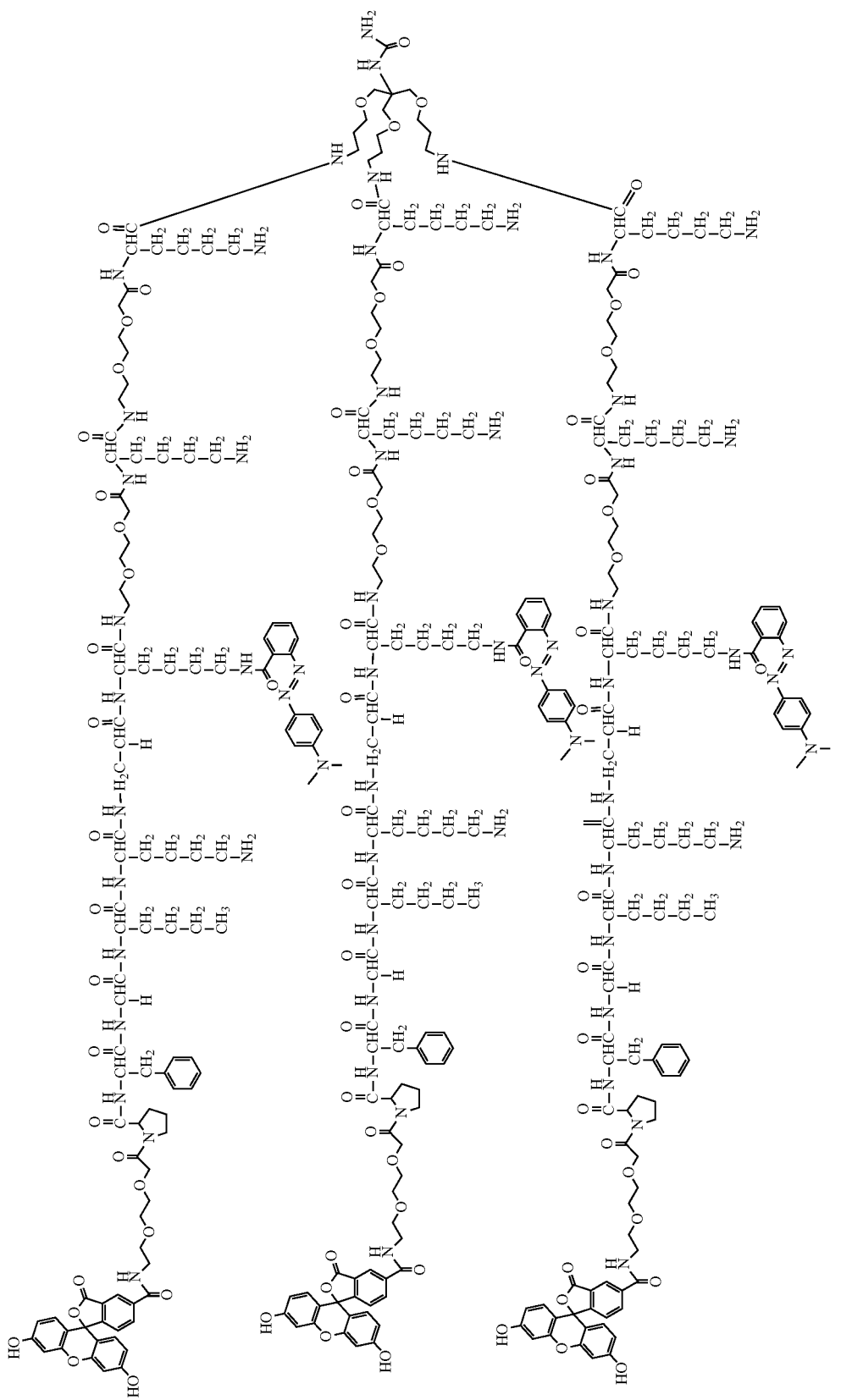

-continued
Compound 6
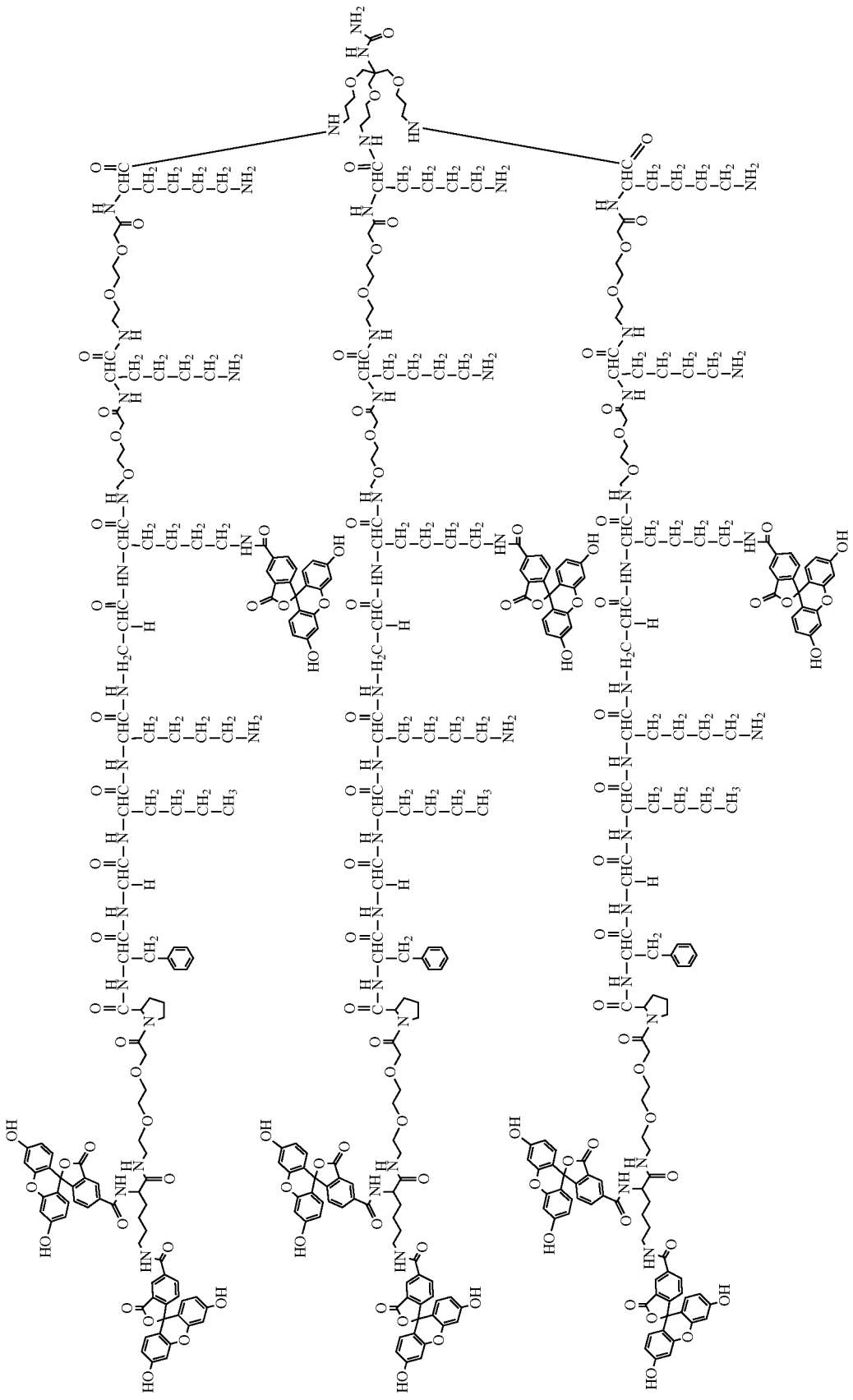
(SVC-01-196): HPLC $t_R$ = 3.884 min, MALDI calc. for $C_{422}H_{507}N_{59}O_{115}$ [M + H]$^+$: 8247.01; found: 8247.774 [M + H]$^+$

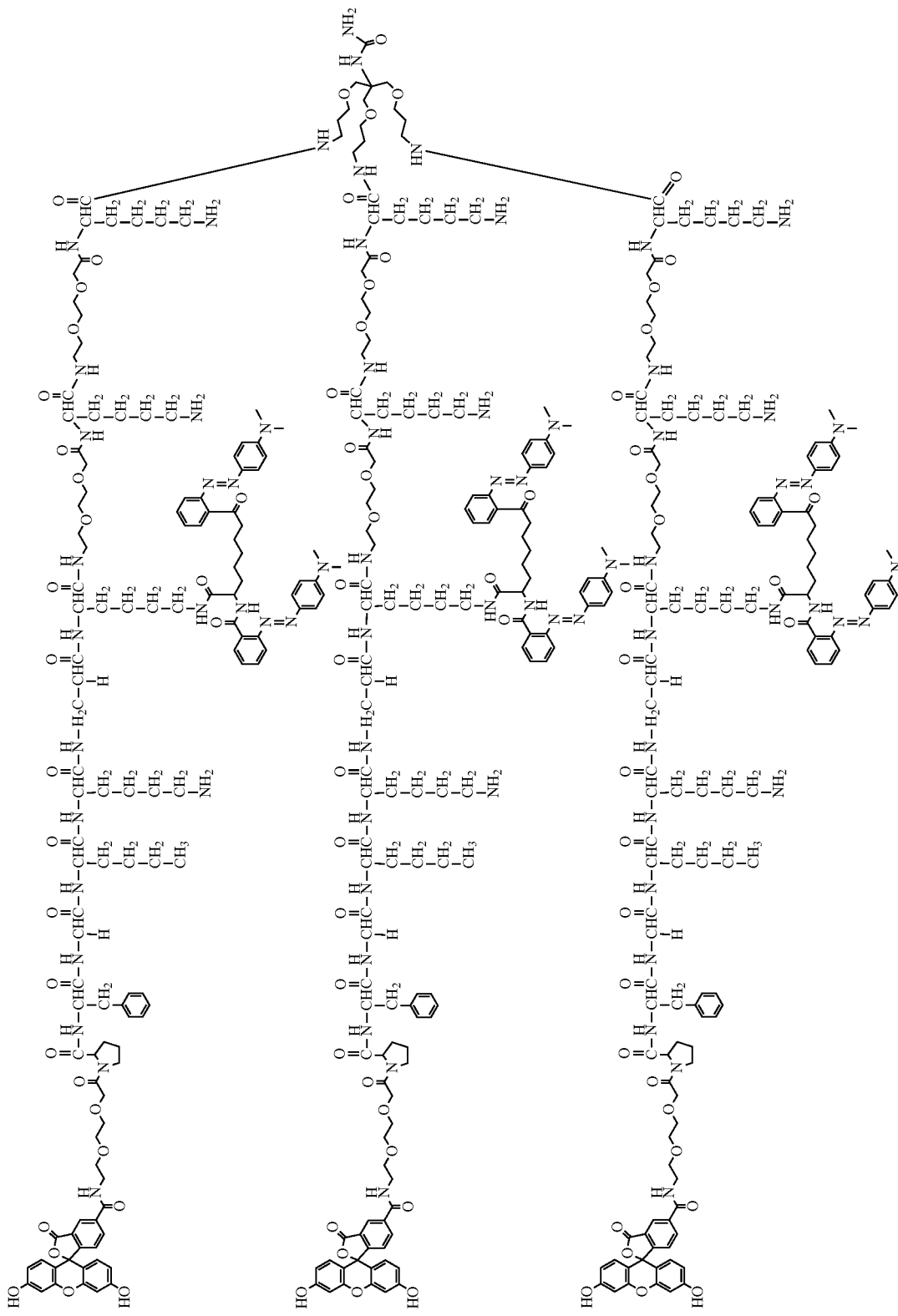

-continued
Compound 8
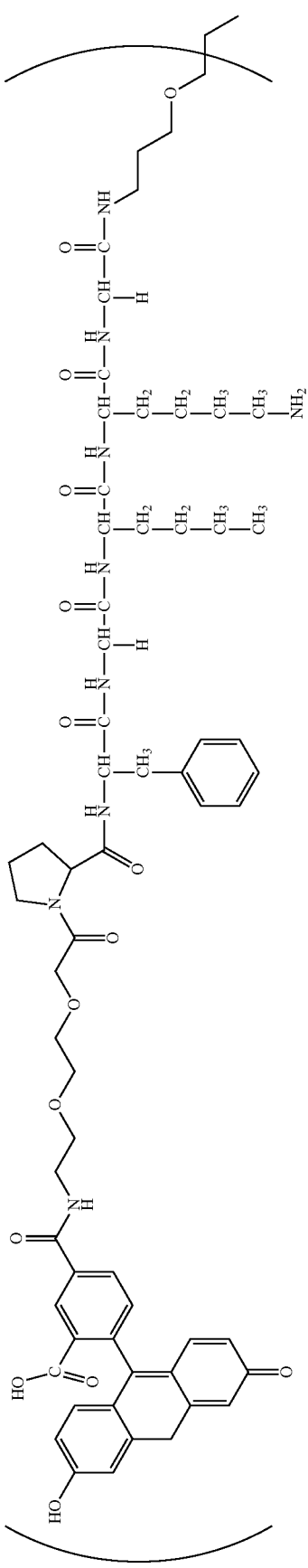
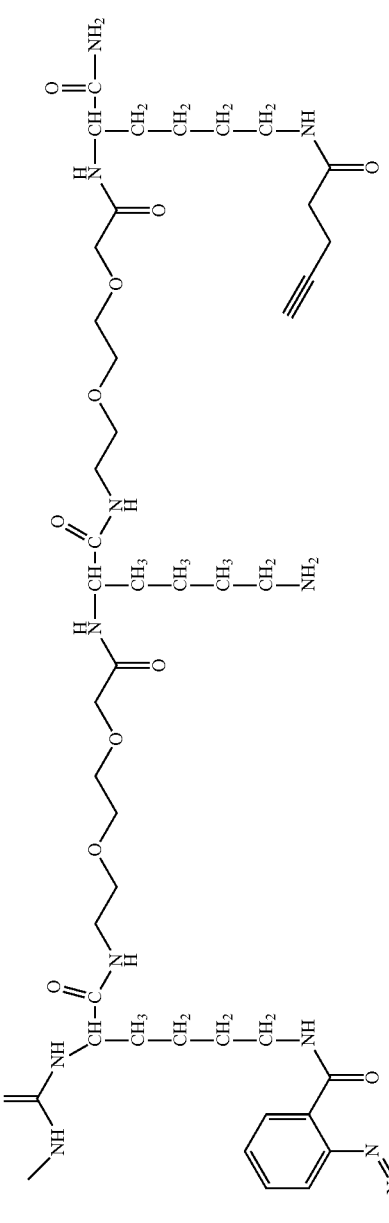
(AMF-212): HPCL $t_R$ = 4.958 min, MALDI calc. for $C_{238}H_{312}N_{40}O_{60}[M+H]^+$: 4694.341; found: 4694.50 $[M+H]^+$
Chmeical Formula: $C_{238}H_{312}N_{40}O_{60}$ Molecular Weight: 4693.3340

-continued
Compound 9
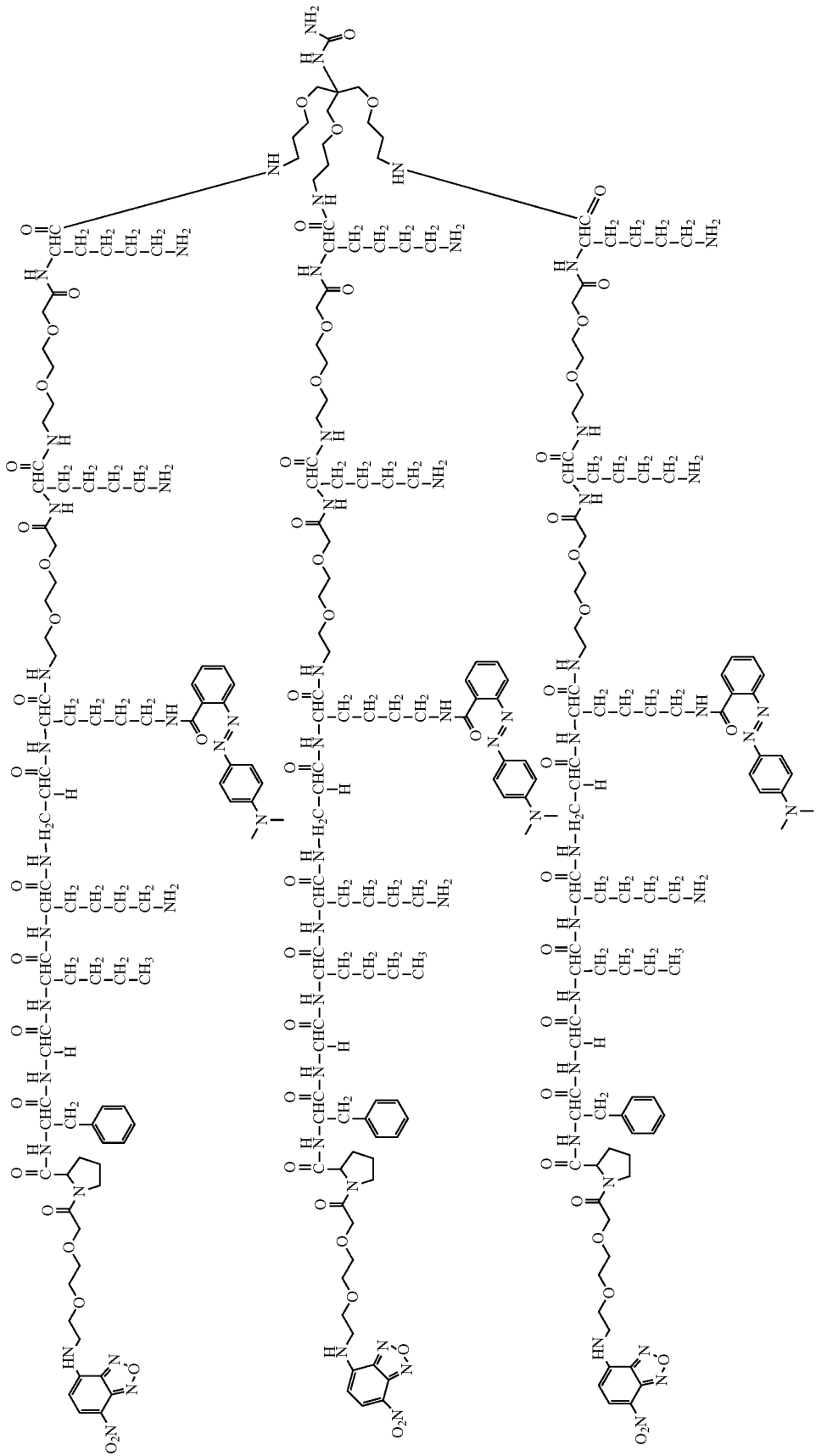
(SVC-02-030): HPLC $t_R$ = 6.229 min, MALDI calc. for $C_{279}H_{425}N_{71}O_{69}$ [M + 7H]$^+$: 840.6077; found: 840.3384.
Chemical Formula: $C_{279}H_{425}N_{71}O_{69}$
Exact Mass: 5874.1930
Molecular Weight: 5877.8970

MALDI-TOF:

Probe was added to saline or pooled BALF from patients with fibrosis and incubated for 30 minutes. A ZipTip (C-18, 0.2 μL) with 5 μL MeCN (with 0.1% TFA as an additive) followed by 20 μL of H2O was washed. The ZipTip was loaded with the sample, washed and eluted into 5 μL of 80% aq. MeCN (with 0.1% TFA as an additive). The sample was analysed by MALDI TOF/TOF (Bruker Ultraflextreme mass spectrometer).

Figure 15:
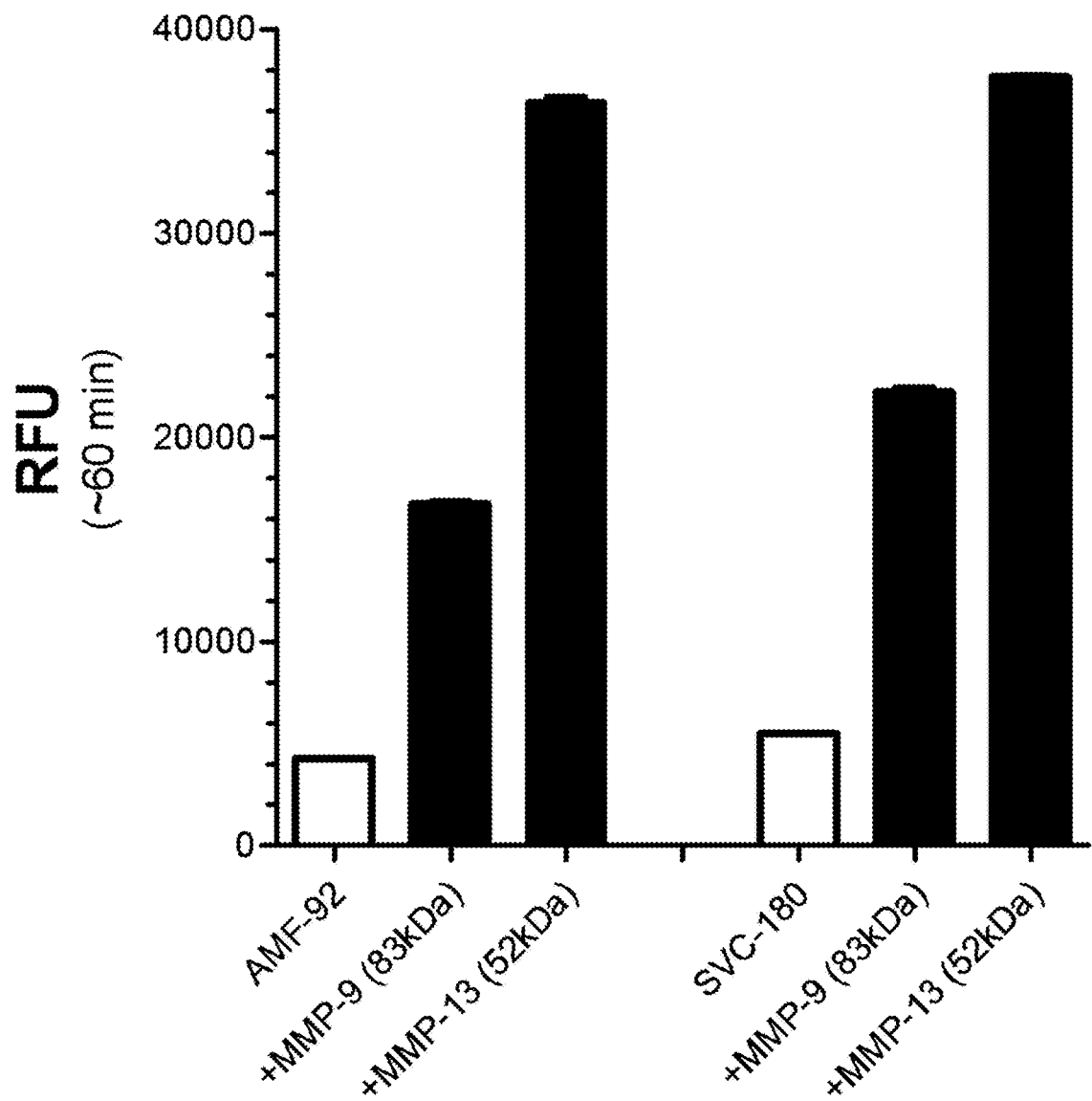
FIG. 15. Enzyme specificity of the polymerisable probe SVC-180 (SVC-01-180) in comparison with FRET monomer AMF-92.

Compound 10:

Polymerisable probe SVC-01-180 (SVC-180). The specificity of the polymerisable probe SVC-180 (SVC-01-180) was tested with MMP-9 and MMP-13 and compared with FRET monomer AMF-92. The results are shown in FIG. 15.

Figure 19:
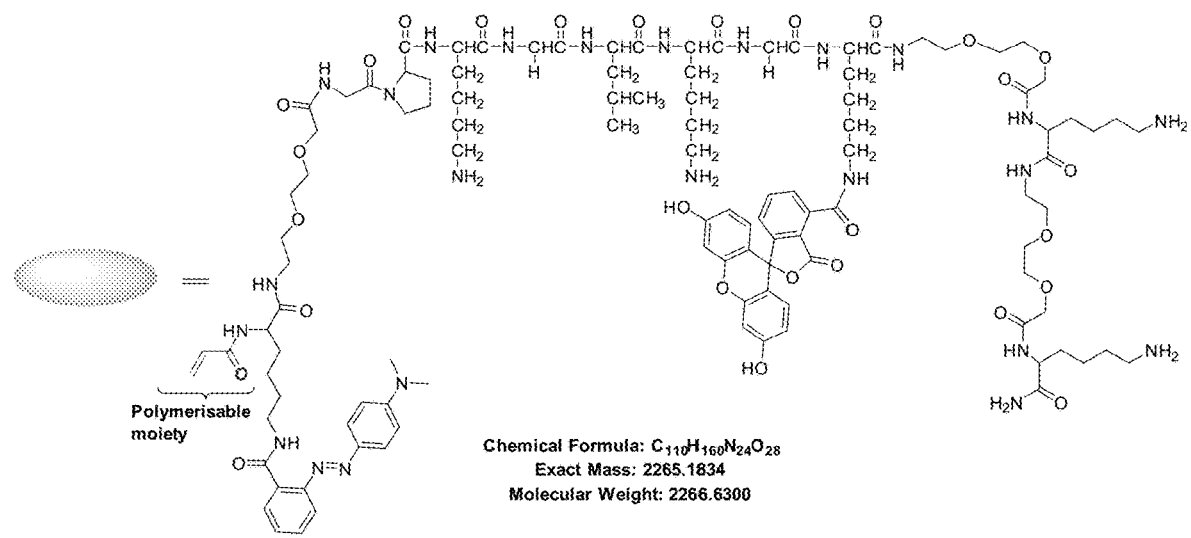
FIG. 19. Illustration of the structure of Compound 10.

By following the procedure for the synthesis of Compound 1, FAM was introduced on the probe by selective Dde group deprotection, followed by coupling of last Fmoc-Lys (Dde)-OH to finish the probe. MethylRed was introduced on N-terminus and finally the polymerisable acryloyl moiety was coupled to complete the synthesis of probe on solid support. After washing the resin with 20% piperidine in DMF followed by DCM, the fragment was cleaved off the resin with TFA-TIS-H$_2$O (95:2.5:2.5) (90 min) and precipitated with cold ether to give Compound 10 (MALDI-ToF m/z: 2265.7; >95% HPLC purity, $t_R$=4.178 min) the structure of which is shown in FIG. 19.

Acryloyl Coupling:

N-terminal capping with acryloyl-NHS ester (1 eq.) was done in anhDMF (0.1M) containing DIPEA (3 eq.) at rt for 12 h. The solution was drained and the resin washed with DMF (3×5 ml), DCM (3×5 ml), MeOH (3×5 ml) and finally ether (3×5 ml).

Figure 20:
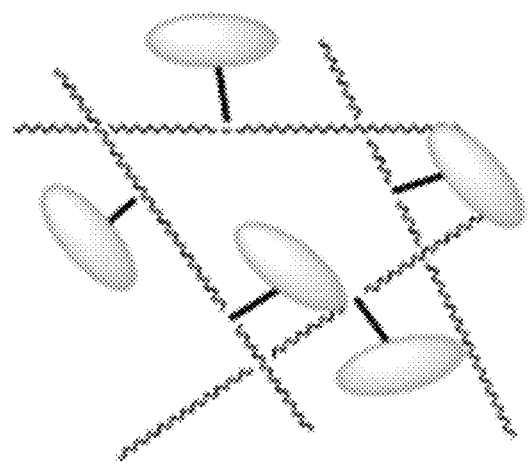
FIG. 20. Illustration of the hydrogel obtainable by the polymerisation of monomer compound 10.

Compound 11:

The polymerisable probe compound 10 (SVC-01-180) was polymerised in water to form a hydrogel. The hydrogel obtainable by the polymerisation of monomer compound 10 can be represented by the polymeric structure as shown in FIG. 20. The polymerisation can be carried out in the presence of a sugar to increase the porosity of the resulting hydrogel. Increasing the porosity improves the access of the enzyme to the polymerised probe.

Acrylamide Polymerisation:

A) Hydrogel monomer solution was prepared by mixing acrylamide (1.20 g) PEGDA 700 (100 μL), TMED (10 μL) in distilled water (3.20 mL) and degassed by purging with N$_2$ for 10 min;

B) Probe monomer solution was prepared by mixing polymerisabable probe (25 mg) in distilled water (1 mL) and degassed by purging with N$_2$ for 10 min;

C) The monomer solution (500 μL) and ammonium persulfate or potassium persulfate (10% in water, 60 μL), and distilled water (250 μL) were mixed with or without sugar/salt (50 μL, 50% in distilled water) and polymerisable probe solution (50 μL) for 1 min. The resulting solution (100 μL/well) was transferred to a 96 well plate and allowed to polymerise at 40° C. After 12 h, the excess of monomer solution was washed away with distilled water until the washings are clear (5×100 μL/well). The hydrogels were allowed to dry at 40° C. for 12 under vacuum protecting from direct light.

A control hydrogel was prepared without probe solution by following the above procedure.

Figure 16:
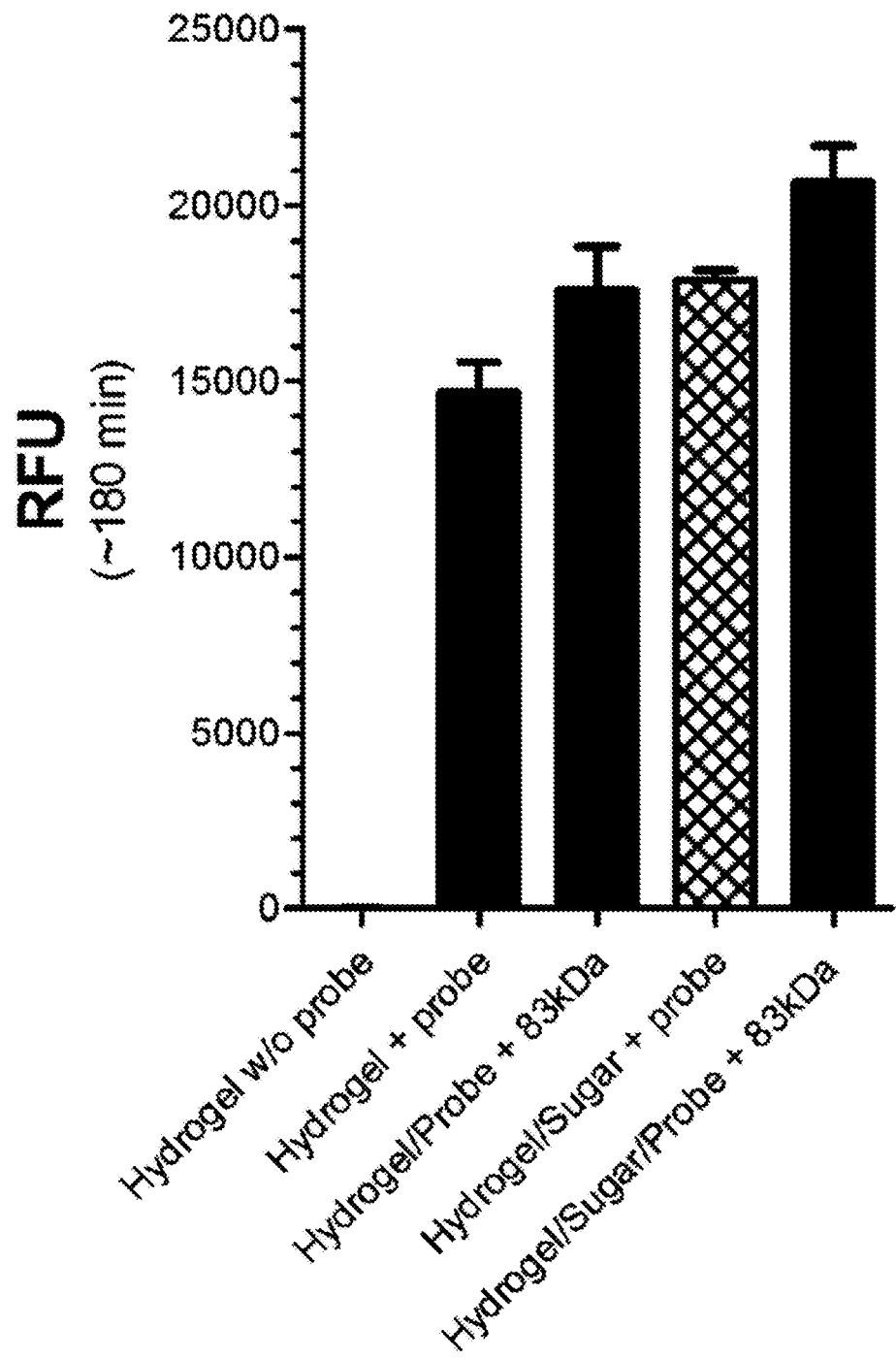
FIG. 16. Ex-vivo analysis of detection of MMP-9 activity by the polymerised hydrogel of probe SVC-180 (SVC-01-180).

The polymerised probe hydrogel was tested for cleavage by MMP-9 and the results are shown in FIG. 16. Since the probe is prepared already immobilised as hydrogel in the 96 well plate, the MMP-9 enzyme (39 and 83 kDa, 5-30 nm in buffer) was added to the wells and the fluorescence from cleaved fragment released in buffer was measured from the control and probe containing hydrogel wells using a plate reader.

Animals

Adult (25-35 g) specific pathogen-free BALB/c and CD1 wild type mice were used. All studies were done under UK Home Office license 60/4434.

Enzyme Assay

The enzyme assays were run in a 384-well format on a PCR opaque microplate (Thermo Scientific). All dilutions and reactions were prepared in MMP buffer (50 mM Tris, 10 mM CaCl$_2$, 0.15M NaCl, 0.05% Brij-35, pH 7). Proteolytic activity was determined by calculating the fold change in fluorescence over background signal provided by the corresponding dilution of the probe and/or inhibitors with exogenous enzymes using a-multiwell plate fluorimeter (Synergy H1 Hybrid Reader, BioTek instruments Ltd) at excitation/emission 485/528 nm. Recombinant human MMPs (Catalytic domain MMP-1, -2, -3, -7, -8, -9, -10, -11, -12, -13 (Enzo Life Sciences) and Full-length MMP-2, -9, -12 and -13 (Merck/Millipore)) were used at 30 nM. Pro-MMP-13 (R & D Systems) was activated by incubating with 1 mM 4-aminophenylmercunc acetate (APMA) for 2 hrs at 37° C. Human neutrophil elastase (Elastase Product Company, used at 2.5 ug/ml), neutrophil lysate (lysed human neutrophils), and recombinant human Thrombin (Sigma-Aldrich, used at 5 U/ml), Plasmin (Sigma-Aldrich, used at 30 nM) and Factor Xa (Sigma-Aldrich, used at 0.5 μM) were used to identify the lead molecular probe sequences. For inhibition assays, enzyme and inhibitor were pre-incubated for 1 hr at 37° C. before the addition of molecular probe. Inhibitors Marimastat (Toris Bioscience), AZD1236 (AstraZeneca), Inhibitor I (Sigma-Aldrich) and SB-3CT (Sigma-Aldrich) were used at 200 nM for in-vitro and 50 μM for ex-vivo assays, respectively.

Human and Ovine Tissue Supernatant

Human fibrotic lung tissue biopsies were obtained from Idiopathic Pulmonary Fibrosis-(IPF) patients at the Royal Infirmary, Edinburgh. Under sterile condition, the tissue was dissected and stored at −70° C. for further analysis. Sheep fibrotic lung tissue biopsies were obtained from an Ovine Pulmonary Adenocarcinoma—(OPA) animal at the Roslin Institute, Edinburgh. Under sterile condition, the tissue was dissected and stored at −70° C. for further analysis. For the preparation of tissue supernatant, frozen tissue was suspended in PBS and homogenised (Bio-Gen PRO200 homogeniser, Pro-Scientific) on ice. Samples were centrifuged at 13000 rpm for 15 min at 4° C. and the debris-free supernatant collected. Total protein concentrations were determined using at Pierce™ BCA kit (Thermo Scientific). The samples were aliquoted and stored at −20° C. or −70° C. until further analysis.

Gelatin Zymography

To assess the MMP activity in human and ovine tissue, gelatin zymography (Novex®, Life technologies) was performed. Total protein concentrations of tissue supernatants were standardised (1 μg/μl, Human and 1.5 μg/μl Ovine) and 20 μl of supernatant mixed with 20 μl of 2× Tris-Glycine SDS sample buffer without boiling. 15 μl of mixed samples were then electrophoresed for 90 min, 150V at 4° C. on 10% Tris-Glycine gel containing 0.1% gelatin. After electrophoresis, the gel was washed with deionised water at room temperature to remove SDS. The gel was suspended in 1× Renaturing Buffer for 90 min at 4° C. before being developed (1× Developing buffer) overnight at 37° C. in Developing Buffer with or without inhibitor (50 μM Marimastat, pan-MMP inhibitor). The gel was washed, fixed and stained with the Colloidal Blue Staining Kit (Novex®, Life technologies) for 3 hrs at room temperature, and destained with deionised water at room temperature. Areas of protease activity appear as a clear band against a dark background.

Haemolytic Toxicity Assay

The haemolytic activities of the molecular probes were evaluated in human red blood cells using a previously reported method (Lequin et al., 2006; Lequin, O. et al. Dermaseptin S., Biochemistry 45, 468-480 (2006)). Fresh human red blood cells were incubated with molecular probe (10 µM final concentration) at 37° C. for 45 min. After centrifugation (350 g for 10 min), the supernatant absorbance was measured at 350 nm. In addition, control samples for 0 and 100% haemolysis were incubated with 0.9% (w/v) NaCl (negative control) or Triton-X-100 (positive control), respectively. Percent haemolysis was calculated according to the following eq: Haemolysis (%)=(Probe/Positive control)×100. Each measurement was taken in duplicate. The $HC_{50}$ was defined as the mean probe concentration that produced 50% haemolysis.

Statistical Analysis

The statistical values are expressed as mean standard error of the mean (SEM). The statistical analyses were performed using Microsoft Excel, and the datasets were tested using Student's t-test. Indications of significance correspond to $p<0.05$ (*) and $p<0.01$ (**).

The invention claimed is:

1. An optical probe comprising at least one fluorophore connected to at least one quencher by an enzyme cleavable peptide sequence; the at least one fluorophore being substantially fluorescently quenched by the at least one quencher when connected to the enzyme cleavable peptide sequence; wherein the at least one fluorophore is separated from the at least one quencher when the enzyme cleavable peptide sequence of at least one probe element is cleaved; wherein the enzyme cleavable peptide sequence is an amino acid sequence of SEQ ID NO:7 and is selectively cleavable by one or more matrix metalloproteinase (MMP).

2. The probe according to claim 1, wherein the at least one quencher is the same type of fluorophore as the at least one fluorophore, and the at least one quencher and the at least one fluorophore self-quench.

3. The probe of claim 1, wherein the at least one quencher is a different type of fluorophore to the at least one fluorophore, and is a fluorescent quencher.

4. The probe of claim 1, wherein the at least one quencher is a dark quencher.

5. The probe according to any claim 1, wherein the at least one fluorophore is a fluorescein, a cyanine fluorophore, a rhodamine, a fluorescent protein, or 7-nitrobenz-2-oxa-1,3-diazole (NBD).

6. The probe according to claim 1, wherein the at least one fluorophore and the at least one quencher form a FRET pair and are selected from (fluorophore/quencher): Cy3/Cy5, Cy3/QSY21, Cy5/QSY21, Cy5/BHQ-3, fluorescein/tetramethylrhodamine, fluorescein/methyl red, NBD/methyl red, cyan fluorescent protein (CFP)/yellow fluorescent protein (YFP), and carboxy fluorescein/methyl red.

7. The probe according to claim 1, wherein the at least one fluorophore is connected to the enzyme cleavable peptide sequence by a spacer.

8. The probe according to claim 7, wherein the spacer is selected from 6-aminohexanoic acid (Ahx) and polyethyleneglycol (PEG).

9. The probe according to claim 1, wherein the unit of the at least one fluorophore connected to the enzyme cleavable peptide sequence corresponds to a probe element and wherein the probe comprises a plurality of probe elements; each of the plurality of probe elements comprising at least one fluorophore connected to an enzyme cleavable peptide sequence.

10. The probe according to claim 9, wherein the probe comprises a core, and the plurality of probe elements are connected to the core.

11. The probe according to claim 10, wherein each probe element within the plurality of probe elements is independently connected indirectly to the core via a linker.

12. The probe according to claim 11, wherein the linker is selected from the group consisting of: [-(lysine)-(PEG$_2$)-]$_{1-2}$, [-(PEG-k)-]$_{1-3}$, and [-(PEG-k)$_{0-2}$-NH—(CH$_2$)$_3$—O—CH$_2$—].

13. The probe according to claim 11, wherein the linker comprises a D-amino acid.

14. The probe according to claim 9, wherein the at least one fluorophore of each probe element within the plurality of probe elements self-quenches, such that the at least one fluorophore of a first probe element substantially fluorescently quenches the at least one fluorophore of a second probe element.

15. The probe according to claim 10, wherein the core comprises the at least one quencher.

16. The probe according to claim 9, wherein each of the plurality of probe elements comprise at least one quencher.

17. The probe according to claim 9, wherein one or more of the plurality of probe elements comprises at least two fluorophores.

18. The probe according to claim 9, wherein the probe comprises at least three probe elements.

19. The probe according to claim 1, wherein the probe comprises at least one reporter fluorophore that is not substantially fluorescently quenched, and wherein the at least one reporter fluorophore fluoresces at a wavelength that is different to the wavelength of light at which the at least one fluorophore fluoresces.

20. A method of detecting MMP in a target zone, the method comprising the steps:
 a. providing a probe according to claim 1;
 b. applying the probe to the target zone;
 c. illuminating the target area with an appropriate wavelength of light to excite the at least one fluorophore of the probe; and
 d. determining the fluorescence intensity of the at least one fluorophore,
wherein significant fluorescence of the at least one fluorophore of the probe is indicative of the presence of MMP in the target zone.

21. The method according to claim 20, wherein the target zone is a portion of tissue of an animal.

22. The method according to claim 21, wherein the tissue type is heart, lung, liver, connective tissue, skin, or intestine.

23. The method according to claim 20, wherein the presence of MMP in the target zone is indicative of active fibroproliferation within the target zone.

24. The method according to claim 20, wherein the target zone is a joint of a subject.

25. The method according to claim 24, wherein the presence of MMP in the target zone is indicative of active arthritis in the target zone.

26. The method according to claim 20, wherein the MMP is MMP-2, and/or MMP-9 and/or MMP-13.

27. The method according to claim 26, wherein the MMP is MMP-9 and/or MMP-13.

28. The method according to claim 20, wherein the presence of MMP in the target zone is indicative of cancer within the target zone.

29. A method of assessing a portion of tissue; the method comprising the steps of:
 a. applying a probe according to claim 1 to the portion of tissue;
 b. illuminating the portion of tissue with an appropriate wavelength of light to excite fluorophores of the probe; and
 c) determining the fluorescence intensity of probe,
wherein significant fluorescence of the probe is indicative of the presence of MMP in the portion of tissue, and the presence of MMP in the portion of tissue is indicative of a disease in which MMP is expressed or overexpressed.

30. The method of claim 29, wherein the disease is active fibroproliferation, cirrhosis, cancer or arthritis.

* * * * *